US008699019B2

(12) United States Patent
Wang et al.

(10) Patent No.: US 8,699,019 B2
(45) Date of Patent: Apr. 15, 2014

(54) ASSURING FOOD SAFETY USING NANO-STRUCTURE BASED SPECTRAL SENSING

(75) Inventors: Hong Wang, Cupertino, CA (US); Xun Guo, Sacramento, CA (US); Chunwei Liu, Beijing (CN); Hao Zhou, Jiangsu (CN); Ning Ma, Jiangsu (CN); Xue Zhong, Jiangsu (CN)

(73) Assignee: OptoTrace (Suzhou) Technologies, Inc., Suzhou (CN)

( * ) Notice: Subject to any disclaimer, the term of this patent is extended or adjusted under 35 U.S.C. 154(b) by 123 days.

(21) Appl. No.: 13/442,835

(22) Filed: Apr. 9, 2012

(65) Prior Publication Data

US 2013/0017298 A1 Jan. 17, 2013

Related U.S. Application Data

(60) Provisional application No. 61/507,592, filed on Jul. 13, 2011.

(51) Int. Cl.
*G01J 3/44* (2006.01)

(52) U.S. Cl.
USPC ............................................. 356/301

(58) Field of Classification Search
USPC ............................ 356/300–334; 426/231–233
See application file for complete search history.

(56) References Cited

U.S. PATENT DOCUMENTS

| | | | |
|---|---|---|---|
| 4,933,274 A | 6/1990 | Sanford | |
| 4,968,516 A * | 11/1990 | Thompson | .................... 426/233 |
| 5,017,007 A | 5/1991 | Milne | |
| 5,244,788 A | 9/1993 | Hubscher | |
| 5,527,712 A | 6/1996 | Sheehy | |
| 5,864,397 A | 1/1999 | Vo-Dinh | |
| 6,361,861 B2 | 3/2002 | Gao | |
| 6,406,777 B1 | 6/2002 | Boss | |
| 6,614,523 B1 | 9/2003 | Boss | |
| 8,241,861 B1 * | 8/2012 | Heinecke et al. | ............. 435/7.21 |
| 2001/0051355 A1 * | 12/2001 | Tryland et al. | .................. 435/34 |
| 2002/0123050 A1 | 9/2002 | Poponin | |
| 2003/0059820 A1 | 3/2003 | Vo-Dinh | |
| 2003/0175472 A1 | 9/2003 | Den | |
| 2004/0012778 A1 * | 1/2004 | Li et al. | ......................... 356/301 |

(Continued)

OTHER PUBLICATIONS

Bell, J.R., et al., "Standards to ensure the authenticity of edible oils and fats", Food, Nutrition and Agriculture, Food and Agriculture Organization of the United Nations, 1994.*

(Continued)

*Primary Examiner* — Gregory J Toatley
*Assistant Examiner* — Dominic J Bologna
(74) *Attorney, Agent, or Firm* — SV Patent Service

(57) ABSTRACT

A method for inspecting an edible oil includes obtaining a first Raman spectrum from an edible oil sample, discovering an unhealthy, unsanitary, unsafe, or adulterated content in the edible oil sample in part by the intensity level of the fluorescence background in the first Raman spectrum, introducing the edible oil sample to nano-scale surface structures to allow molecules of the edible oil sample to be adsorbed to the nano-scale surface structures, illuminating the edible oil sample and the nano-scale surface structures by a laser beam, obtaining a second Raman spectrum from light scattered by molecules of the edible oil sample adsorbed to the nano-scale surface structures, and identifying the unhealthy, unsanitary, or unsafe content in the edible oil sample using one or more first spectral signatures in the second Raman spectrum.

28 Claims, 41 Drawing Sheets

(56) References Cited

U.S. PATENT DOCUMENTS

| | | |
|---|---|---|
| 2004/0106203 A1 | 6/2004 | Stasiak |
| 2005/0136552 A1 | 6/2005 | Buechler |
| 2007/0008523 A1* | 1/2007 | Kaye et al. .................... 356/300 |
| 2009/0046284 A1* | 2/2009 | Wang et al. .................... 356/301 |
| 2010/0114514 A1* | 5/2010 | Wang et al. .................... 702/82 |
| 2010/0240870 A1* | 9/2010 | Su et al. ........................ 530/363 |
| 2011/0134423 A1* | 6/2011 | Yu et al. ........................ 356/311 |

OTHER PUBLICATIONS

Farhad, et al., 2009, Determination of Ratio of Unsaturated to Total Fatty Acids in Edible Oils by Laser Raman Spectroscopy, Journal of Applied Sciences, vol. 9, pp. 1538-1543.*

* cited by examiner

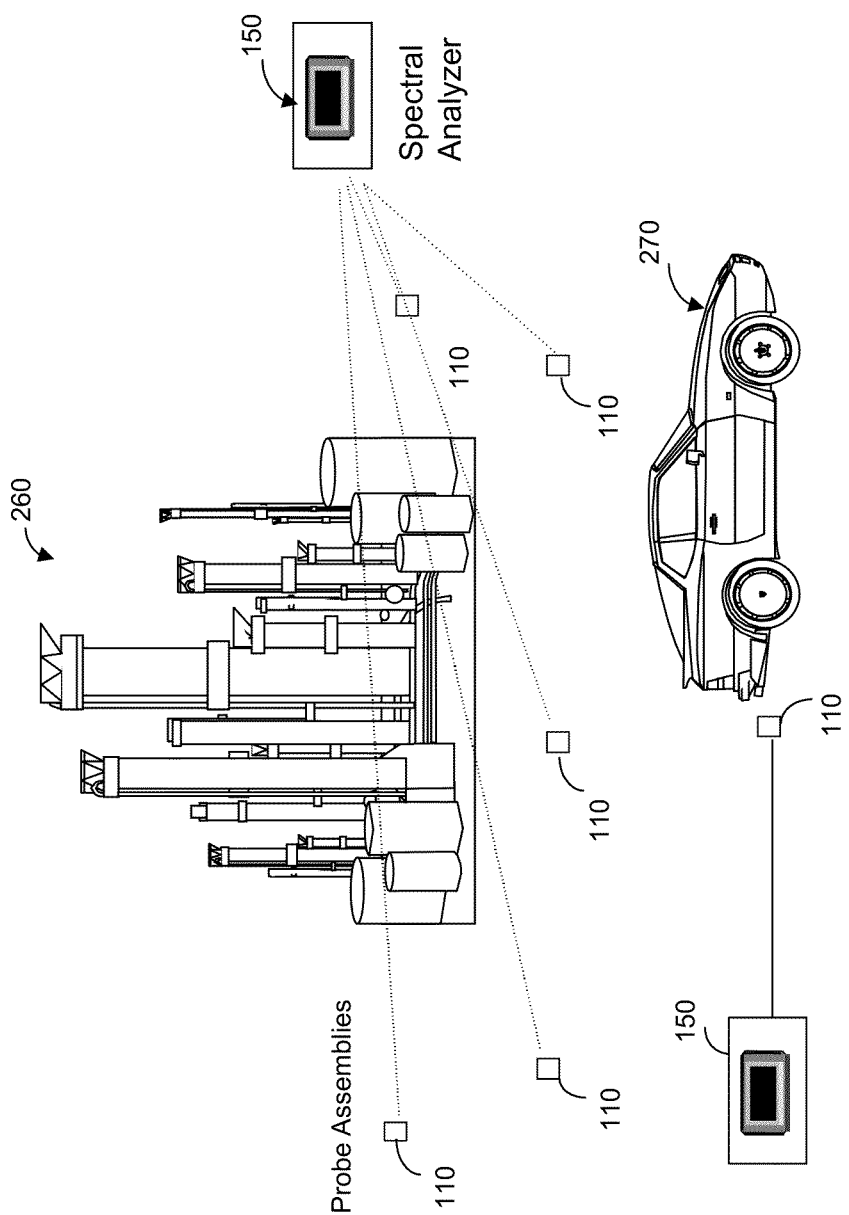

SECTION A-A

ASSURING FOOD SAFETY USING NANO-STRUCTURE BASED SPECTRAL SENSING

The present application claims priority to U.S. Provisional Patent Application 61/507,592, entitled "Analyzing chemical and biological substances using nano-structure based spectral sensing" filed Jul. 13, 2011. The disclosures of the above patent applications are incorporated herein by reference.

BACKGROUND OF THE INVENTION

The present invention generally relates to detection of chemical, biological, radioactive, and other substances by a light scattering probe and a chemical sensor.

Light scattering techniques such as Raman spectroscopy are known to be capable of identifying chemicals and biological agents. A major limitation associated with Raman spectroscopy is that the Raman scattering signals from chemicals and biological agents tend to be very weak. Although many attempts have been made to increase Raman scattering intensity, such efforts have not yielded practical and economical detectors based on Raman spectroscopy. As a result, Raman scattering so far only has very limited applications in sensing chemicals and biological agents.

A specific need for high sensitivity spectral sensing has arisen recently in the area of food safety. Many of the food products that are contaminated with or illegitimately mixed with harmful substances which may not have colors or smells that can be easily detected in the field such as grocery stores and food distribution centers. Although sophisticated analyses can be conducted in central chemical labs, but the testing methods are too costly and have too long a turn-around times to be feasible for food inspection and safety monitoring in high volume and high throughput commercial food industry.

A need therefore exists for effective and practical Raman spectroscopy based detectors for trace amount of chemical, biological, radioactive, and other substances.

SUMMARY OF THE INVENTION

The present application discloses spectral sensing systems and methods that can detect harmful substances in food products cost effectively with fast turn-around time. The food inspection can be conducted using portable devices at the grocery stores, food distribution vehicles, and food distribution centers. An advantage of the disclosed systems and methods is that food products containing unsafe, unhealthy, and harmful products that cannot be recognized with naked eyes, which can now be conveniently detected in the field. As a result, food monitoring and safety can be significantly enhanced. The disclosed methods are applicable to a wide range of food products, for example, edible oils.

In one general aspect, the present invention relates to a method for inspecting an edible oil. The method includes obtaining a first Raman spectrum from an edible oil sample; discovering an unhealthy, unsanitary, unsafe, or adulterated content in the edible oil sample in part by the intensity level of the fluorescence background in the first Raman spectrum; introducing the edible oil sample to nano-scale surface structures to allow molecules of the edible oil sample to be adsorbed to the nano-scale surface structures; illuminating the edible oil sample and the nano-scale surface structures by a laser beam; obtaining a second Raman spectrum from light scattered by molecules of the edible oil sample adsorbed to the nano-scale surface structures; and identifying the unhealthy, unsanitary, or unsafe content in the edible oil sample using one or more first spectral signatures in the second Raman spectrum.

Implementations of the system may include one or more of the following. The step of discovering can include determining the existence of unhealthy, unsanitary, or unsafe content in the edible oil sample if the fluorescence background in the first Raman spectrum is above a threshold level. The spectral background in the first Raman spectrum is measured in the spectral range from $250\,cm^{-1}$ to $600\,cm^{-1}$. The threshold level can be within a range between about 8,000 and about 30,000. The unhealthy, unsanitary, or unsafe content can include one or more of a waste edible oil, swill oil, oils refined from animal skin of pigs, cows, veal, chickens, or, oils refined from animal visceral, or repeatedly reused edible oil. The plurality of unhealthy, unsanitary, or unsafe content can include one or more of an edible oil that fried French fries, an edible oil that fried lamb, pork, or chick, or edible oil that is mixed with pork fat. The adulterated content in the edible oil sample can include palm oil. The method can further include: establishing a plurality of spectral signatures in surface enhanced Raman spectra for a plurality of edible oils and identifying a specific unhealthy, unsanitary, or unsafe content in at least one of the plurality of edible oils using the plurality of spectral signatures. The plurality of spectral signatures can be located at or around $620\,cm^{-1}$, $730\,cm^{-1}$, or $960\,cm^{-1}$. The method can further include determining a concentration of the unhealthy, unsanitary, unsafe, or adulterated content in the edible oil sample using the one or more first spectral signatures. The method can further include establishing a second spectral signature in surface enhanced Raman spectra for a fresh edible oil; and identifying the edible oil sample as the fresh edible oil using the second spectral signature in the first Raman spectrum. The fresh edible oil can include corn oil, peanut oil, a light vegetable seed oil, rapeseed oil, dark vegetable seed oil, sunflower oil, palm oil, olive oil, grapeseed oil, safflower oil, cotton seed oil, coconut oil, sesame oil, tea oil, and soybean oil. The second spectral signature can be located at or around $1,500\,cm^{-1}$, which is for a light vegetable seed oil or rapeseed oil. The second spectral signature can be located at around $1,162\,cm^{-1}$, which is for peanut oil. The step of identifying can include subtracting a background from the second Raman spectrum to obtain a background-subtracted Raman spectrum; and identifying the unhealthy, unsanitary, unsafe, or adulterated content using the one or more first spectral signatures in the second Raman spectrum and in the background-subtracted Raman spectrum. The step of identifying can further include identifying the unhealthy, unsanitary, unsafe, or adulterated content in the edible oil sample if the ratio is above 3. The unhealthy, unsanitary, unsafe, or adulterated content can be identified in the edible oil sample if the ratio is above 4. The unhealthy, unsanitary, unsafe, or adulterated content can be identified in the edible oil sample if the ratio is above 5. The method can further include qualifying the edible oil sample as a fresh edible oil if the ratio is below a threshold value. The method can further include introducing the edible oil sample to the nano particles in a solution, or on a nano-structured surface, wherein the nano-scale surface structures are provide by nano particles. The nano particles can include a magnetic or ferromagnetic material. The method can further include applying an electrical field, a magnetic field, or an electro-magnetic field to the sample solution during at least a portion of the step of collecting.

In another general aspect, the present invention relates to a method for inspecting an edible oil that includes obtaining a Raman spectrum from an edible oil sample; subtracting a background from the Raman spectrum to obtain a background-subtracted Raman spectrum; identifying a first Raman signature in the Raman spectrum; identifying a second Raman signature in the Raman spectrum; calculating a first ratio of the intensities of the first Raman signature and the second Raman signature in the background-subtracted Raman spectrum; and identifying an adulterated content in the edible oil sample using the first ratio.

Implementations of the system may include one or more of the following. The first Raman signature can be at around 1262 cm$^{-1}$, and wherein the second Raman signature is at around 1300 cm$^{-1}$. The method can further include obtaining an advertised content for the edible oil sample from a product label for the edible oil sample; obtaining a second ratio of the intensities of the first Raman signature and the second Raman signature in a background-subtracted Raman spectrum for the advertised content; and identifying the adulterated content in the edible oil sample by comparing the first ratio and the second ratio. The second ratio can be smaller than the first ratio. The adulterated content can be identified in the edible oil sample if the first ratio differs from the second ratio by a predetermined value. The adulterated content includes palm oil.

BRIEF DESCRIPTION OF THE DRAWINGS

The following drawings, which are incorporated in and from a part of the specification, illustrate embodiments of the present invention and, together with the description, serve to explain the principles of the invention.

FIG. 5 is a schematic diagram showing environmental monitoring using a Raman scattering probe.

DETAILED DESCRIPTION OF THE INVENTION

Figure 1:
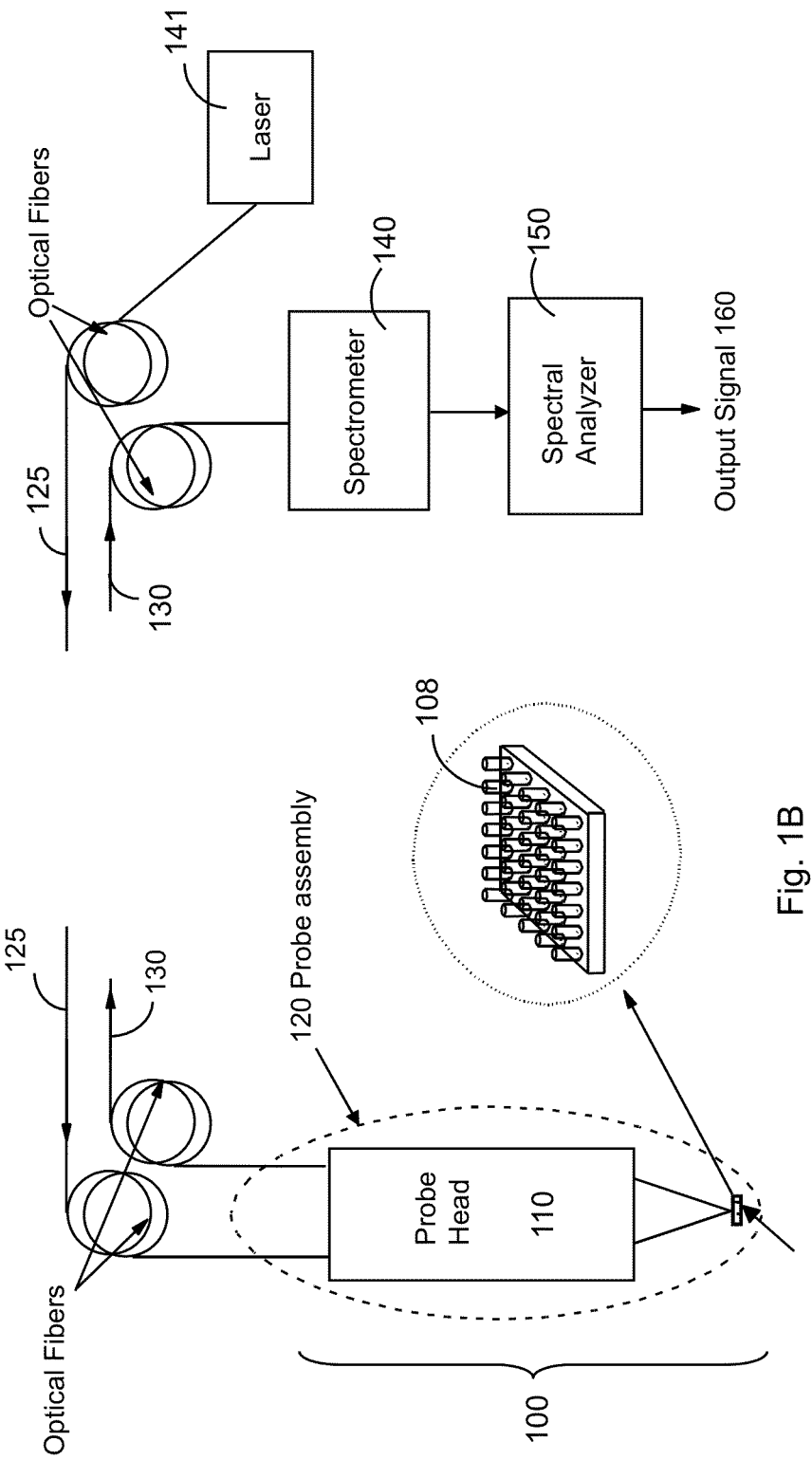
FIGS. 1A-1C illustrate an exemplified system for detection of chemical and biological substances using a Raman Scattering probe.

FIGS. 1A-1C respectively illustrate a system for detecting trace chemical or biological substances using surface-enhance Raman scattering. Referring to FIG. 1A, a light scattering probe 100 includes a probe head 110, and a sensor 105 positioned adjacent to the probe head 110. The sensor 105 includes a nano surface structure. For example, the nano surface structure can include a plurality of nano rods 108 (shown FIG. 1B), a plurality of nano holes, a cluster of nano particles in solution, or other surface structures having dimensions at nanometer scale. In some embodiments, as described below, a nano structured surface structures can be prepared by coating the surface of the sensor 105 of a solution containing a colloidal suspension of nano particles. The solution can be subsequently evaporated to deposit the nano particles on the surface. In the present specification, the term "nano particle" refers to a particle having at least in one dimension with a size smaller than 1,000 nm.

In some embodiments, a sample fluid can be introduced to the nano rods 108 in the sensor 105. The sample fluid can include a body fluid obtained from a patient or an illicit drug user for disease diagnosis and drug use determination, or a fluid of gas phase. Examples of the body fluid include blood, saliva, urine, serum, tear, sweat, stomach fluid, hydrothorax, ascites, CSF, sperm, and a secrete body fluid. The sample fluid can also comprise a food sample for detecting harmful or illegal additives in a food product to ensure food safety. Examples of food products include dairy products such as milk, milk powder, baby formula, cheese, yogurt, ice cream, milk-containing food products such as milk-containing candies, cake and cookies, and protein-containing food products. The probe head 110 and the sensor 105 can be enclosed in a probe assembly 120. The probe assembly 120 can be depressurized by a vacuum pump to reduce the contamination of the sensing surfaces by foreign substances.

A laser beam emitted by a laser 141 is guided by an optical fiber 125, as shown in FIG. 1C, to the probed head and to illuminate the nano surface structure on the sensor 105 (FIG. 1A). The light scattered by the sample solution on the nano-surface of the sensor 105 is collected by the probe head 110 and guided to a spectrometer 140 by an optical fiber 130. A Raman spectrum of the scattered light is obtained by a spectral analyzer 150 using the output of the spectrometer 140. One or more spectral signatures in the Raman spectrum are identified and compared with predetermined spectral signatures for various molecules. An output signal 160 indicates identification of a targeted molecule, for example, a harmful materials in food or water, dangerous materials (explosive or flammable materials), or disease related molecules, when a threshold of certain molecules under detection is exceeded. In the present specification, the term "spectral signature" refers to one or more spectral peaks, one or more spectral valleys, and other spectral shapes such as relative peak height, peak line width, and peak shape which can be used to characterize one or more molecular bonds in a biological, medical, or chemical substance.

In some embodiment, the sensor 105 can include various nano structures on sensors as disclosed in the commonly assigned pending U.S. patent application Ser. No. 12/014, 800, titled "Optical sensing system on a micro-array structure", filed Jan. 26, 2008, the content of which is incorporated herein by reference. The optical sensing system that includes an optical sensor that includes a substrate having an upper surface and a plurality of tapered walls on the substrate, wherein at least one of the tapered walls is aligned along an longitudinal direction, wherein the plurality of tapered walls comprise sloped surfaces oriented at oblique angles relative to the upper surface, wherein the sloped surfaces are configured to adsorb molecules of a chemical sample; a light source configured to emit an incident light beam to impinge the plurality of tapered walls adsorbed with molecules of the chemical sample; and a detector that can collect light scattered by the plurality of tapered walls to allow a determination of the sample chemical.

The sensor 105 can also include a substrate having an upper surface and a plurality of tapered walls on the substrate, wherein the plurality of tapered walls comprise sloped surfaces oriented at oblique angles relative to the upper surface of the substrate, wherein at least two adjacent tapered walls define therein an air gap having a width that varies as a function of a distance from the upper surface; a light source configured to emit an incident light beam to impinge the plurality of tapered walls adsorbed with molecules of a chemical sample; and a detector that can collect light scattered by the plurality of tapered walls to allow a determination of the sample chemical.

In some embodiment, the sensor 105 can include multi-layer nano structures such as multi-layer nano rods and multi-layer nano holes as disclosed in the commonly assigned pending U.S. patent application Ser. No. 11/754,912, titled "Light scattering device having multi-layer micro structure", filed May 29, 2007, nano particle clusters or groups, or multi-layer nano particles in a solution, the content of which is incorporated herein by reference. The nano surface structure can include a silicon substrate; an adhesion layer on the silicon substrate; a bias layer on the adhesion layer; and one or more structure layers on the adhesion layer. The one or more structure layers can include different material compositions and a plurality of holes through at least two of the two or more of structure layers. The widths of the plurality of holes can be in the range of 0.5-1,000 nm. The nano surface structure can also include a silicon substrate; an adhesion layer on the silicon substrate; a bias layer on the adhesion layer; and a plurality of columns on the bias layer. At least one of the plurality of columns or holes can include two or more structure layers having different material compositions and have widths in the range of in the range of 0.5-1,000 nm.

Figure 2:
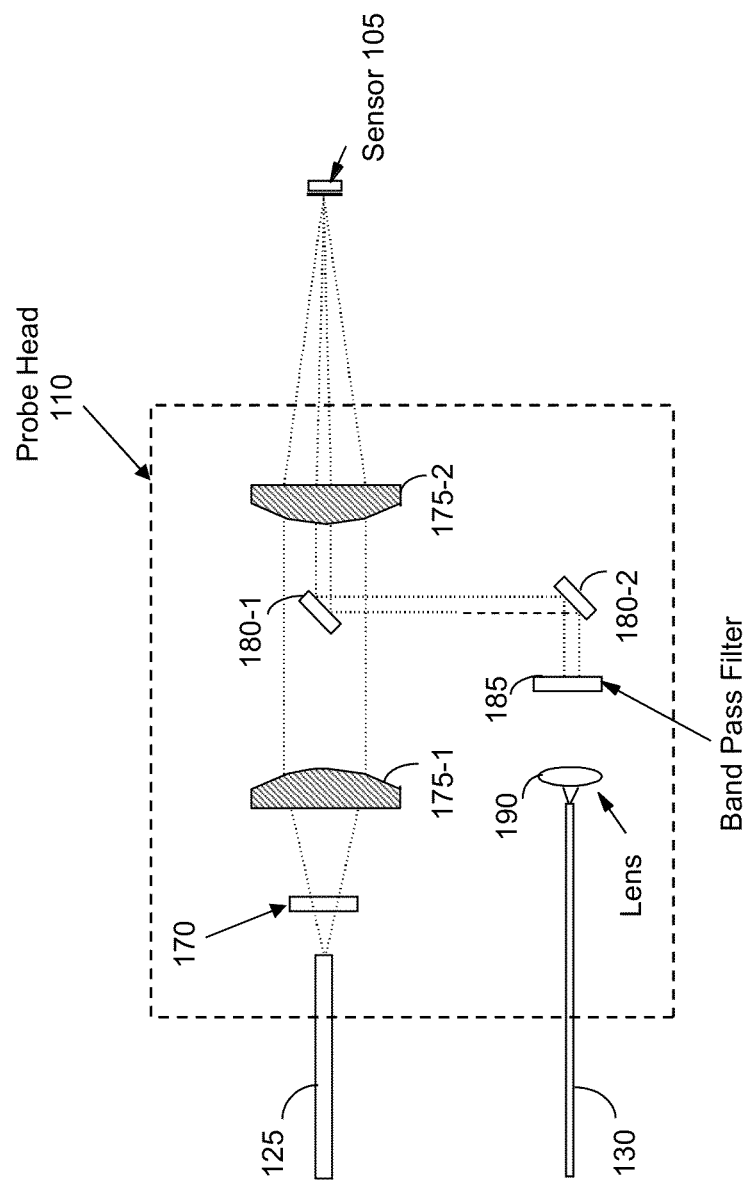
FIG. 2 illustrates an exemplified probe head for a Raman scattering probe compatible with FIGS. 1A-1C.

Referring to FIG. 2, the probe head 110 receives a laser beam from an input optical fiber 125. The laser beam passes through a band ejection filter 170 and lenses 175-1 and 175-2 to project onto the sensor 105. A scattering light from the sensor 105 is directed by a group of mirrors 180-1 and 180-2 to pass through another band-pass filter 185 and further collimated by a collimating lens 190 to enter the collection optical fiber 130.

The trace chemicals or biological agents to be detected can be provided in the form of a gas, a liquid, a solid, a sol gel, or an aerosol. The molecules are adsorbed onto the nano surface or nano particles of the sensor 105. Such adsorbed molecules have much larger scattering cross section under laser beam illustration than that they are in free form in a gas, a liquid, a solid, a sol gel, or an aerosol. When a laser beam illuminates the adsorbed molecules, Raman scattering spectrum of the molecules can be obtained. Targeted chemicals or biological agents can be identified using predetermined Raman spectral signatures for the molecules.

Figure 3A:
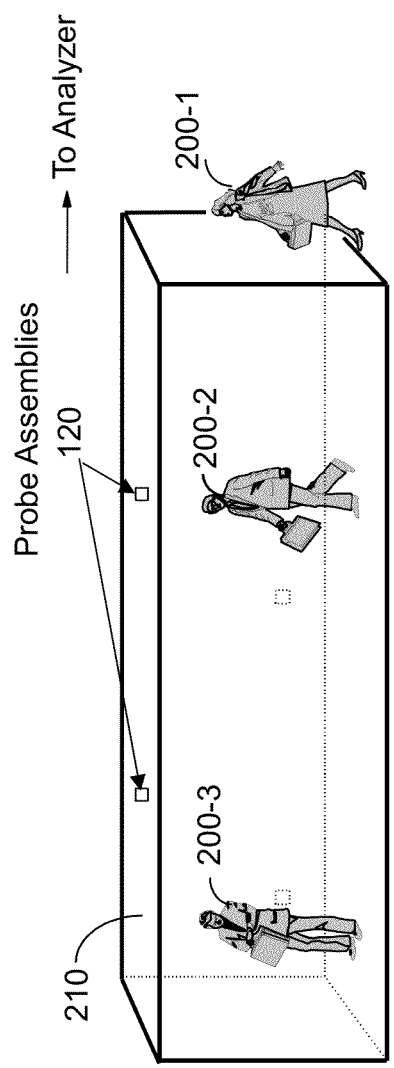
FIGS. 3A and 3B are schematic diagrams respectively showing inspections of passengers and luggage using a Raman scattering probe at an airport.

FIG. 3A shows an exemplified application of Surface-Enhance Raman Scattering in the area of transportation safety. Passengers 200-1, 200-2, and 200-3 walking through a passageway tunnel 210 are screened. One or more probe assemblies 120 with embedded sensor 105 are placed in the passageway tunnel 210. The probe assemblies 120 can be connected by fibers to a spectral analyzer 150 in a nearby or remote office. In each probe assembly 120, a probe head and a sensor are packaged together. The probe head is aligned to point to the sensing surface of a sensor 105. The passageway tunnel 210 can be forced ventilated and under little negative pressure and/or little higher temperature to increase evaporation of harmful materials. If a passenger (e.g., the passenger 200-2) carries an explosive material, a harmful chemical, a chemical weapon, a flammable liquid, a bio-chemical weapon, a nuclear weapon or a narcotic drug, a trace amount of such materials will volatilize into air such that molecules of the material can be adsorbed onto the surface of a sensor through a specially designed sample collection system (a detailed example is disclosed in the above referenced and commonly assigned U.S. Pat. No. 7,384,792). The Raman Spectra can be recorded and compared with the spectral signatures of known substances stored at a database at a central office. As soon as the harmful materials are detected, an alarm signal will be triggered. Appropriate security responses will be activated.

Figure 3B:
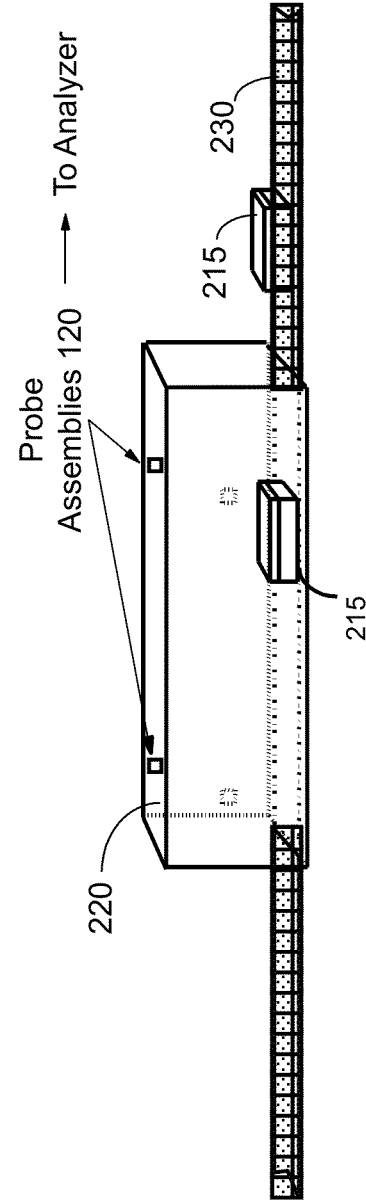

Referring to FIG. 3B, cargos 215 for freight transportation are carried by a conveyer 230 to pass through cargo screening channel 220. Probe assemblies 120 each embedded with a sensor 105 are placed around the cargo screen channel 220. The probe assemblies 120 can be connected with fibers to the spectral analyzer 150 in office near or far away from it. The probe assembly 120 is aligned to the surface of a sensor 105 and they are packaged together to detect any explosives, chemical or biochemical weapon, or harmful chemicals enclosed in the luggage 215. This configuration can be implemented in other applications such as checked-in luggage for passenger air travel, mail stations, railway stations, subway stations, custom inspection areas, traffic control zones, ship or submarine, airplanes, schools, hotels, restaurants, shopping centers, recreation centers, buildings, and other public places, etc. This configuration can be easily implemented to detect gun powders and other explosives, flammable materials including liquids, or other hazardous materials.

Wired Sensor Network

Figure 4A:
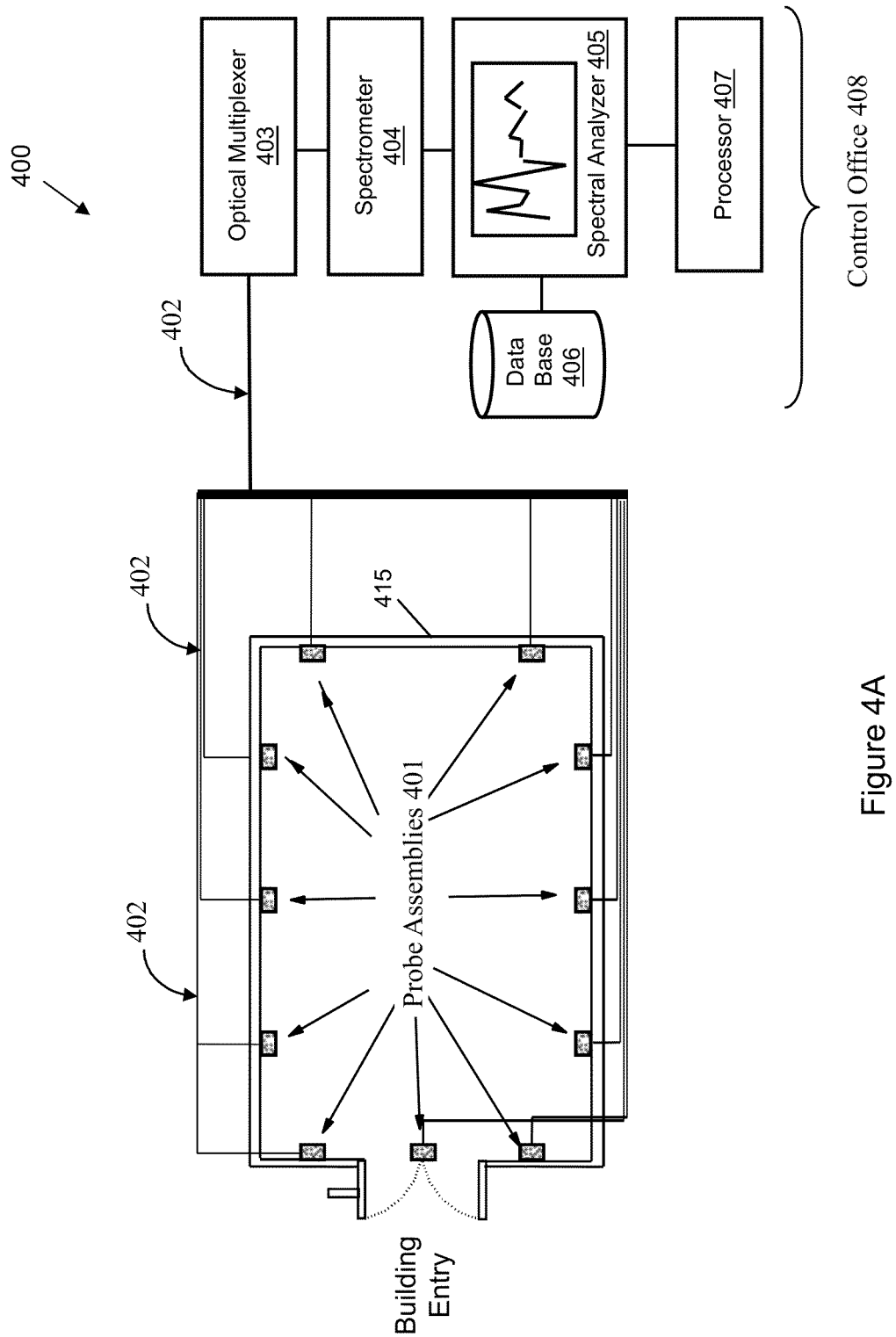
FIG. 4A is a schematic diagram for a network of wired-line connected Raman scattering probes for monitoring the safety of a building.

Referring to FIG. 4A, a sensor-network system 400 is used in safety monitoring of a public building such as airport, railway, bus stations, ballpark buildings, Federal buildings, auditoriums, theaters, courthouses, shopping mall, other public buildings, or a people gathering place. A plurality of probe assemblies 401 are installed at various locations in a public building 415 or others protected areas. Each probe assembly 401 includes a probe head and a sensor (not separately shown in FIG. 4A). The probe head can be implemented similar to the probe head 110 (FIG. 1A) but can include a laser device. The sensor is compatible with the sensor 105 (FIG. 1B) that includes a nano surface structure on the surface. The sensor can also be a liquid solution that is configured to receive reagent to be detected. The solution can also include nano particles configured to adsorb the molecules of the reagents. The probe assemblies 401 are applied to monitor many different molecular substances to provide earlier detection of any dangerous or harmful chemicals enter into the monitor areas. The optical signals collected by the probe assemblies 401 can be fed in multiple channels via optical fibers 402 to an optical multiplexer 403 at a control office 408. The optical signals are analyzed by a spectrometer 404 to produce spectral signals, which are analyzed by a spectral analyzer 405. Spectral signatures are identified in the spectral data by the processor 407 using pre-stored spectral signatures in a database 406. Particular examples of hazardous material monitoring include, but not limited to detection of explosive materials including liquids, chemical or biochemical weapons including anthrax, flammable liquid materials, drugs, and so on.

Wireless Sensor Network

Figure 4B:
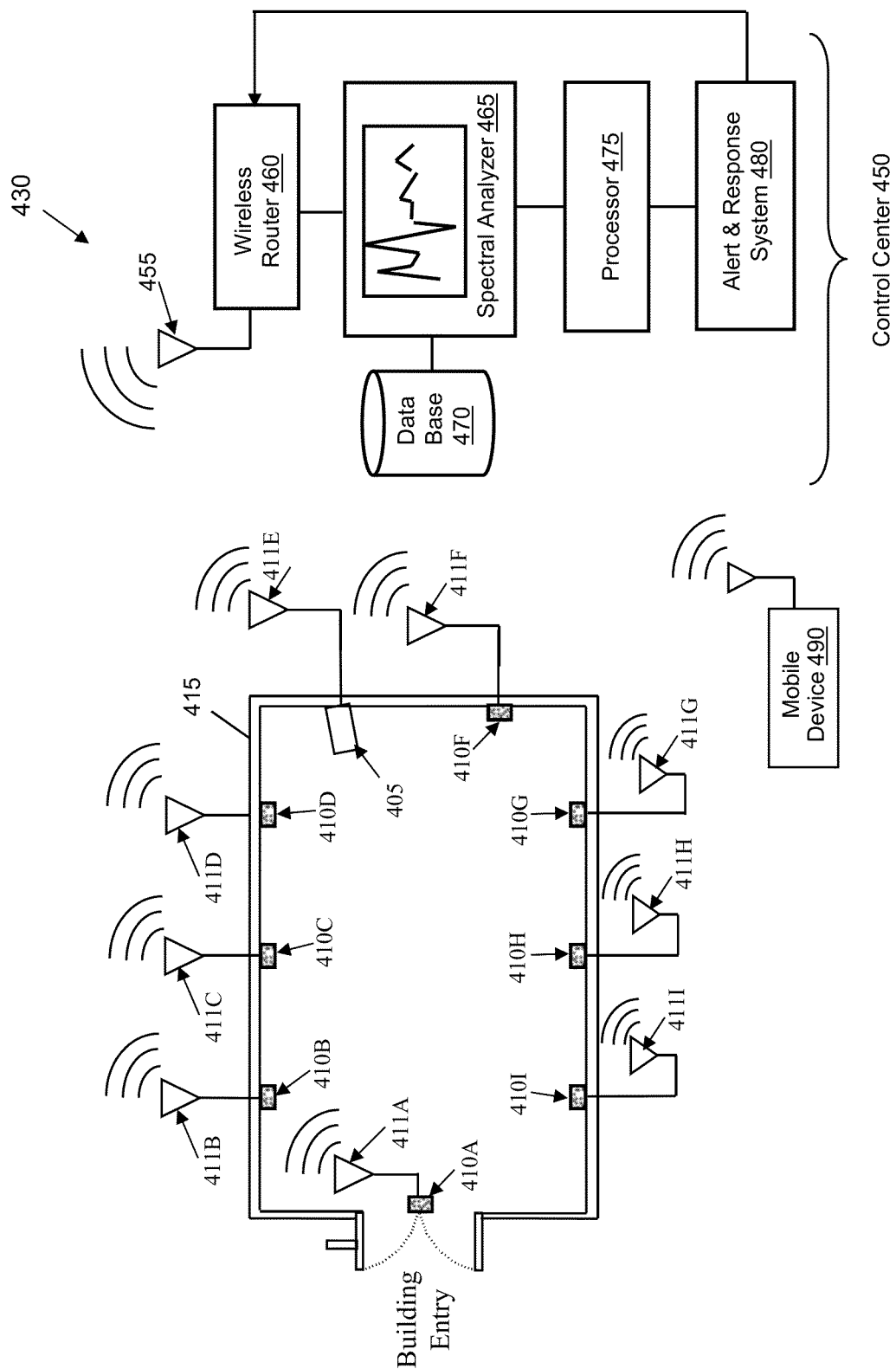
FIG. 4B is a schematic diagram for a network of wireless connected Raman scattering probes for monitoring the safety of a building.

In some embodiments, a sensor-network system 430 is shown in FIG. 4B. A building 415 includes a building entry and a plurality of walls. Probe assemblies 410A-410I are installed at various locations in the building 415. The probe assemblies 410A-410I are respectively coupled to antenna 411A-411I which can transmit locally detected spectral information to a control center 450.

Figure 4C:
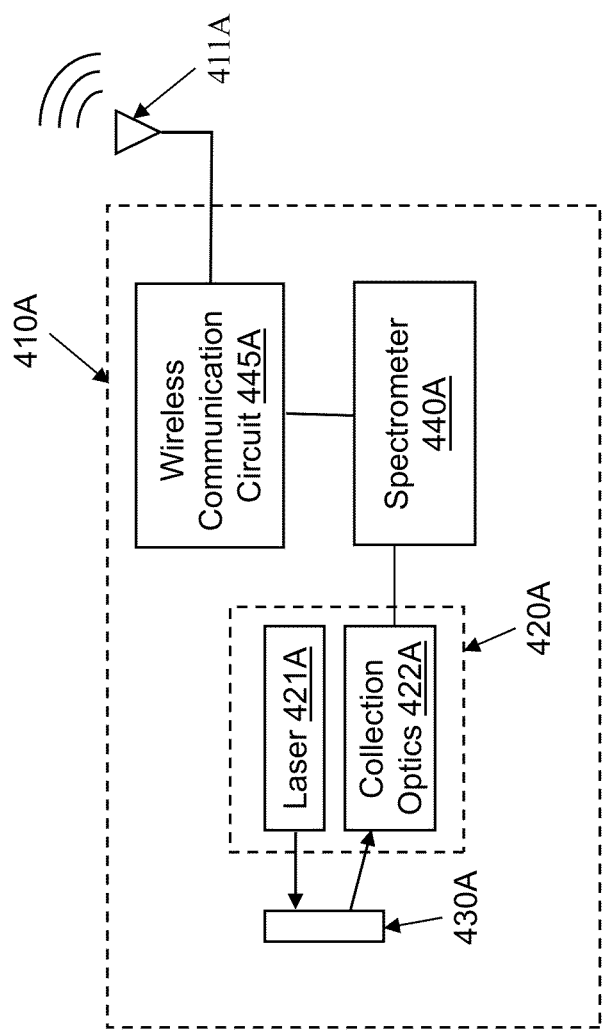
FIG. 4C illustrates an exemplified configuration for a probe assembly capable of wireless communication with a control center.

Each probe assembly 410A, as shown in FIG. 4C, includes a probe head 420A and a sensor 430A positioned adjacent to the probe head 420A. The sensor 430A can collect substances in the ambient environment. In some embodiments, the sensor 430A includes a nano-structured surface that can adsorb molecules of the substance collected in the ambient environment. The probe head 420A includes a compact laser 421A (e.g., a semiconductor laser) that is configured to illuminate a laser beam on the sample molecules in or adsorbed on the sensor 430A. The probe head 420A further includes collection optics 422A that can collect light scattered from the sample molecules in or adsorbed on the sensor 430A, wherein the scattered light comprises information about molecules of the sample molecules. The sensor 430A is compatible with the sensor 105 (FIG. 1B) that includes a nano structure on the surface. The sample molecules can be adsorbed on the nano surface structures to scatter the incident laser light. The sensor 430A can also include a liquid solution that is configured to receive reagent to be detected (e.g., see FIG. 7 below). The solution can also include nano particles configured to adsorb the molecules of the reagents.

The probe head 420A also includes a compact spectrometer 440A that is configured to produce a spectrum of the scattered light collected by the probe head 420A. The spectral data is output from the spectrometer 440A to a wireless communication circuit 445A. The wireless communication circuit 445A can include an RF transceiver, one or more amplifiers, and impedance matching circuit. The wireless communication circuit 445A is configured to transmit the spectral data detected by probe assembly 410A to the control center 450 (FIG. 4B).

The control center 450, referring back to FIG. 4B, includes a wireless router 460 coupled with an antenna 455 configured to receive the wireless signals from the antenna 411A-411I and produce electronic signals comprising spectral data extracted from the wireless signals. The control center 450 can be located within a short range (e.g., within a couple of miles) from the source location (e.g., the building 415) to allow wireless signals comprising the spectral data to be communicated in a wireless protocol such as Bluetooth, WiMax, WiBro, WiFi, WLAN, 802.16, and others. The control center 450 can also be located at a long distance from the source location, wherein the wireless signals comprising the spectral data can be communicated using wireless communications standards and protocols such as Global System for Mobile communications (GSM), Universal Mobile Telecommunications Service (UMTS), and Code Division Multiple Access (CDMA). GSM can include GPRS, EDGE and CSD. UMTS can include Wideband Code Division Multiple Access (WCDMA), High-Speed Packet Access (HSPA), High-Speed Downlink Packet Access (HSDPA), UMTS-TDD, and Long Term Evolution (LTE). CDMA can include CDMA2000 and Ultra Mobile Broadband (UMB).

A spectral analyzer 465 at the control center 450 is configured to receive the electronic signals comprising the spectral data from the wireless router 460. A spectrum such as Raman spectrum is obtained and analyzed by the spectral analyzer 465. As described in more detail below, different chemical or biological substances often carry unique spectral signatures. These spectral signatures can be predetermined using a known chemical or biological substances and a sensor similar to the ones installed in the probe assemblies 410A-410I. The spectral signatures can be stored in a database 470. The spectral analyzer 465 can use the spectral signatures stored in the database 470 as reference to identify spectral signatures in the spectral data. A processor 475 can compute and determine substances captured by the plurality of probe assemblies 410A-410I at different times at different locations of the building 415. If a hazardous substance is identified from the spectral data obtained by one or more probe assemblies 410A-410I, the processor 470 can immediately send a report to an alert and response system 480. The hazardous substance can, for example, include explosives and flammable materials, poisonous gas and other harmful chemicals, and contagious virus and bacteria. The alert and response system 480 is configured to send warning notification signal to the wireless router 460, which can in turn transmit wireless signals to mobile devices 490 and other wireless devices to alert security and other responsible personnel to take proper response actions. The mobile device 490 can include a laptop personal computer, a personal digital assistant (PDA), a mobile internet device (MID), a cellular phone, a smart phone, or a wireless server or router. An application example is to remotely or stand-off monitor a vehicle passing a inspection station on a road, which the sensor in the station is electrically shielded in order not to trig any explosive materials in a nearby vehicle. The inspection action can include to wirelessly control a robotic arm with the probe to collect air phase sample in a vehicle to test, a analyzer can be connected with the probe with either wired (such as optic fibers and cables, etc.), or a wireless way.

Figure 4D:
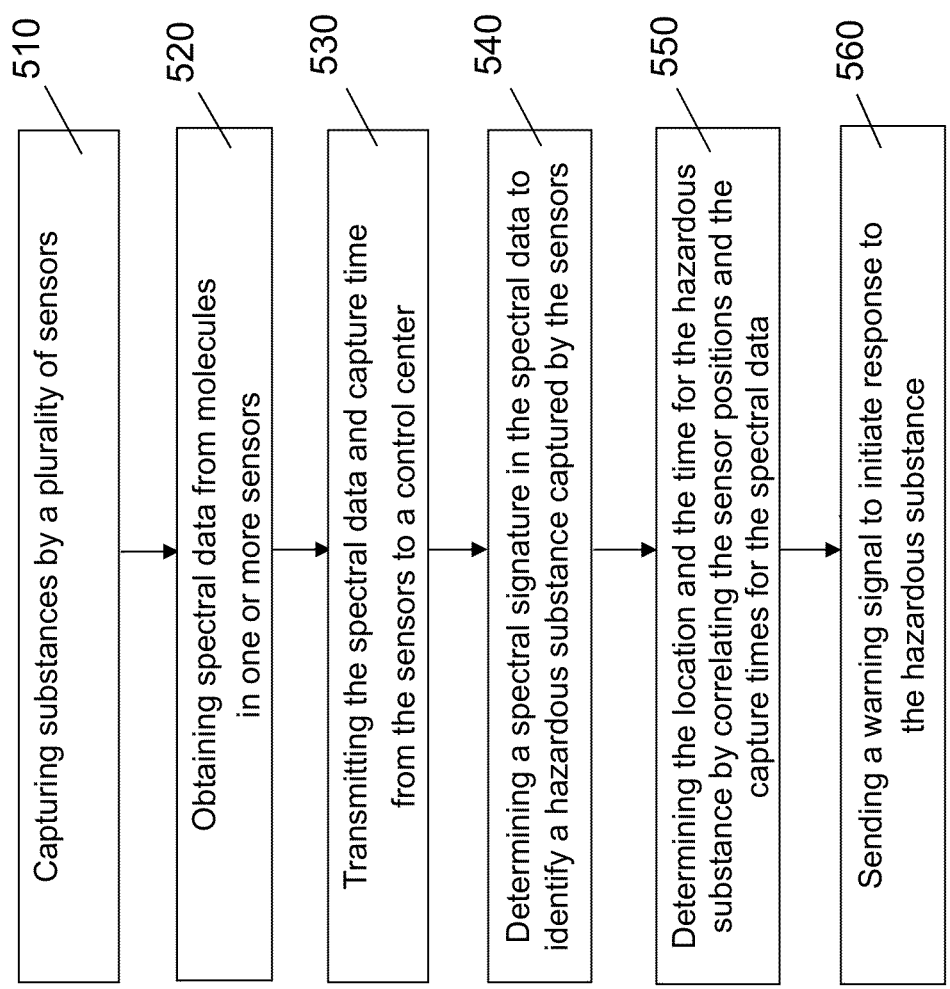
FIG. 4D is an exemplified flowchart for identifying the time and the location of the source of a hazardous substance.

In some embodiments, referring to FIG. 4D, a network of probe assemblies are installed at predetermined positions in a building, an airport, a custom, a conveyance system for cargo or luggage, a health advisor's office, a check station on a road, a harbor, in a vehicle, a ship, a submarine, an airplane, a train, a subway, a building, an industrial site, a resort area, a shopping mall, a research Lab, a school, or a water source, a people gathering place, etc., as described above in relation to FIGS. 3B-4C. Each probe assembly includes a sensor and a probe head configured to emit a laser beam and collect scattered light from the molecules in the sensor. The sensor can have a nano structured surface configured to adsorb the molecules. The probe assembly also includes a spectrometer for producing spectral data such as Raman spectrum from the scattered light. The network of sensors can periodically capture substances (step 510) from each sensor's environment. For sensors having nano-structured surfaces, molecules of the captured substance are adsorbed on the nano structured surfaces on the sensors. Spectral data are next obtained from the molecules adsorbed to the nano structured surfaces in one or more sensors (step 520). Alternately, the molecules to be detected can be captured in a sample solution, and/or adsorbed to nano particles suspended in the sample solution. As described above, a laser beam is emitted by a laser in the probe assembly to illuminate the molecules adsorbed on the nano structured surfaces on a sensor or in a sample solution. Light scattered by the molecules is collected by the probe assembly. The spectral data is obtained from the scattered light by a spectrometer in the probe assembly. An example for the spectral data is Raman spectrum. The nano structured surface on the sensor provides surface enhancement to the signal intensity in the Raman spectrum. The substance capture and associated spectral data can be periodically conducted, for example, at 1 min, 10 min, 15 min, or hours of intervals. In some embodiments, spectral data can be produced in response to a command received from a control center.

The spectral data is next transmitted from the sensors to a control center (step 530). The substance capture time can also be transmitted in conjunction with the spectral data. The spectral data transmission can be via a wired data lines (as shown in FIG. 4A) or a wireless communication network (as shown in FIGS. 4B and 4C). The data center can include a spectral analyzer and a data base storing spectral signatures of predetermined know hazardous substances. The spectral analyzer is used to determine if a spectral signature exists in the spectral data received from the sensors. A hazardous substance can be identified if a spectral signature for a known hazardous substance is found in the spectral data (step 540).

The hazardous substance may be identified by more than one sensor in the network of sensors. The identifications of the hazardous substance can occur at different times by different sensors. For example, as a passenger 200-2 walks through the passageway 210 (FIG. 3A), different sensors in the network may pick up the hazardous material at different times and at different location. A processor (475, FIG. 4B) at the control center can determine the location and time for the hazardous substance by correlating the sensor positions and the capture times for the spectral data (step 550). The location for a stationary hazardous material can be determined by interpolating the positions of the sensors. The location dependence of the hazardous substance detected at different sensors can be used as weighting factors to determine the exact location of the hazardous material, which can be expressed in a two-dimensional (2D) coordinate or a three-dimensional (3D) coordinate. The capture times of the hazardous substance by different sensors at different locations can be used by the processor at the control center to determine a spatial-time profile (that is locations as a function of time) for the hazardous material. The position of the future locations of the hazardous can therefore be predicted by the processor.

In some embodiments, the spectral data collected by the sensors can be used in conjunction with image data captured from the scene near the spectral sensors. For example, a video camera 405 at a location near the spectral sensor where the hazardous substance is identified can capture a suspected person or package. The image of the suspected person or package can be stored and reported in association of the location of the hazardous substance to prepare for an appropriate response.

A warning signal is next sent to an alert response system which can initiate response to the hazardous substance (step 560). The warning signal can be in the form of emails, text messages, and voice phone call, etc. The level of urgency can be categorized by different risk levels such as green (safe), blue, yellow, orange, red (the most risky). The warning signal can include the current and/or anticipated position of the hazardous substance as well as the suspected exterior appearance for the carrier or the package for the hazardous substance. Appropriate personnel can be alerted. Security personnel can be dispatched to the location of the hazardous substance. An evacuation can be initiated.

FIG. 5 is schematic diagram of applying the disclosed sensors to monitor harmful chemicals released into the environment. The probe assemblies 120 are distributed around potential pollution source, e.g., a factory 260 or around highway where great number of automobiles 270 pass through. The probes assemblies 120 can be distributed around the monitored areas and transmit scattered light to a central spectrum analyzer 150, which can determine the contents and concentration of substance released into the environment. The monitoring sample can be, but not limited, soil, water, lake, river, seashore, well, plants, air, aerosol, etc. This application can be extended to car exhausted gas detection and monitoring by placing the probe assembly at the outlet of a car exhaust.

Some Applications of Nano-Structure Based Spectral Sensing

In some embodiments, compact Raman sensor having wireless communication capability can be used inside human body. For example, a system-on-chip Raman system can include on-chip mini-laser source, semiconductor or MEMS device based mini-spectrometer, wireless module, mini-probe, etc. One exemplified application is disease diagnosis of digest system. For example, a patient can swallow a tablet sized Raman spectral sensing system after his/her digest system got cleaned. Raman spectral scans can be taken at predetermined time intervals. The spectral data is then transferred by a wireless module to a wireless receiver outside of the human body. A computer can analyze the spectral data by searching and matching existing data in a database, which can lead to identification of a disease. In another exemplified application, a needle-shaped minimally invasive probe head can bring mini-Raman sensor into diagnosis area inside a human body. Raman spectral data can be transferred through optic fiber, or wireless module. Such applications can include but not limit to diagnosis of cancers (such as breast cancer, colon cancer, esophageal cancer, lung cancer, liver cancer, bladder cancer, pancreas cancer, kidney cancer, ovarian cancer, oral cancer, neck and brain cancer, skin cancer, and stomach cancer), Alzheimer's disease, Parkinson disease, etc. An exemplified cancer marker for SERS is humane epidermal growth factor (HER2), CA-125, or CA-549. An example for a SERS marker for lung cancer is carcinoembryonic antigen (CEA), or A-549.

The disclosed Raman spectral sensing systems and methods are suitable for biotechnology and biomedical applications, such as biometric identity verification by testing samples of tissues or body fluids of a human or an animal, A549 cell of lung cancer, DNA, RNA and proteins, and biomarkers include CEA, CA-125, CA 19-9, CA-549, PSA, AFP, A549, DNA sequencing, DNA sorting, etc.

The disclosed Raman spectral sensing systems and methods are suitable for drug screening. The samples for drug screening can be obtained by human body fluid test, or/and breath test. The disclosed Raman spectral sensing systems and methods are also suitable for forensic applications. The samples can be in the forms of liquid phase, such as human body fluid or animal body fluid, for example, saliva, urine, blood, serum, or powders. Related applications also include false signature recognition; human identification and screening by DNA profiling; identify microscopic paint fragments, fiber identification, etc.

The disclosed Raman spectral sensing systems and methods are suitable for security applications such as detections of hazardous materials, chemical weapons, biological agents, explosive materials (in the forms of powders, solids, liquids, aerosol, or gases), flammable materials including liquids, solids and powders, narcotic drugs, and radioactive materials.

The disclosed Raman spectral sensing systems and methods are suitable for food safety inspection and environmental monitoring. Harmful chemicals and biological agents in the forms of gas, liquid, powder, gel, aerosol, or solid phases can be monitored in food, fruits, beverages and water. The harmful chemicals can include residue pesticides (e.g., methamidophos, cypermethrin, deltamethrin, malachite green, etc.), dioxins, illegal artificial additives (e.g., sudan I, sudan II, sudan III, sudan IV, melamine, Rhodanmine B, sulfide (e.g., NaS), art green, etc.), heavy metals in water including but not limited to Pd, Cd, Hg, As, Cr, or Cu metals and those metal containing compounds, cyanides (e.g., KCN, NaCN), chlorates, sulfates. Food and drug processing by-products (e.g., acrylamide formed from potato chips from processing temperature over 120° C., melamine form from biochemical drug manufacturing process, etc.) can be monitored to detect harmful chemicals such as acrylamide and melamine using the disclosed Raman spectral sensing techniques. Foods inspections include but not limit to potato chips, French fries, fried potato, potato crisps, cookies, crackers, cereal products, crisp bread, bread, coffee, prepared toast, roasted nuts, biscuits, chocolates, popcorn, and aquatic products including fish, etc. drug investigation include but not limit to biochemical drug raw materials, semi-finished products, or products containing NH2 group and/or aromatic group.

The disclosed Raman spectral sensing systems and methods are suitable for identifying and monitoring food packaging processing and preparation materials, which includes identifying and screening polyvinyl chloride (PVC), phthalate contained materials, and polystyrene (PS), used as the microwave food wrap, kitchen film, food packaging, food and liquid container, and processing and preparation materials.

The disclosed Raman spectral sensing systems and methods are suitable for identifying counterfeit merchandizes such as medicines, drugs, Chinese medicine, milk-based powders, edible oil, wines, tea, cigarette, gemstones, currency bills, false signature through inks, art pieces, gasoline, etc.

The disclosed Raman spectral sensing systems and methods are suitable for industrial quality control and production safety monitoring. Other areas of applications include process control for product quality, process and production safety at gas and wet chemical process lines, which can include petroleum refinery plant, chemical engineering manufacturing plant, semiconductor wet chemical process line in clean room, airline and space shuttle, boat, ship, submarine, a chemical related process line or application site, etc.

The disclosed Raman spectral sensing systems and sensor networks can be applied to medical clinic offices, surgery operation rooms, shopping centers, resort area, buildings, customs, road check station, harbors, airports, vehicles, boats, ship, submarine, airplanes, space shuttles, industrial process sites, R&D research labs, quality control offices, education institutes, labs offices, and water sources such as surface water, wells, ground waters, and so on.

Figure 6A:
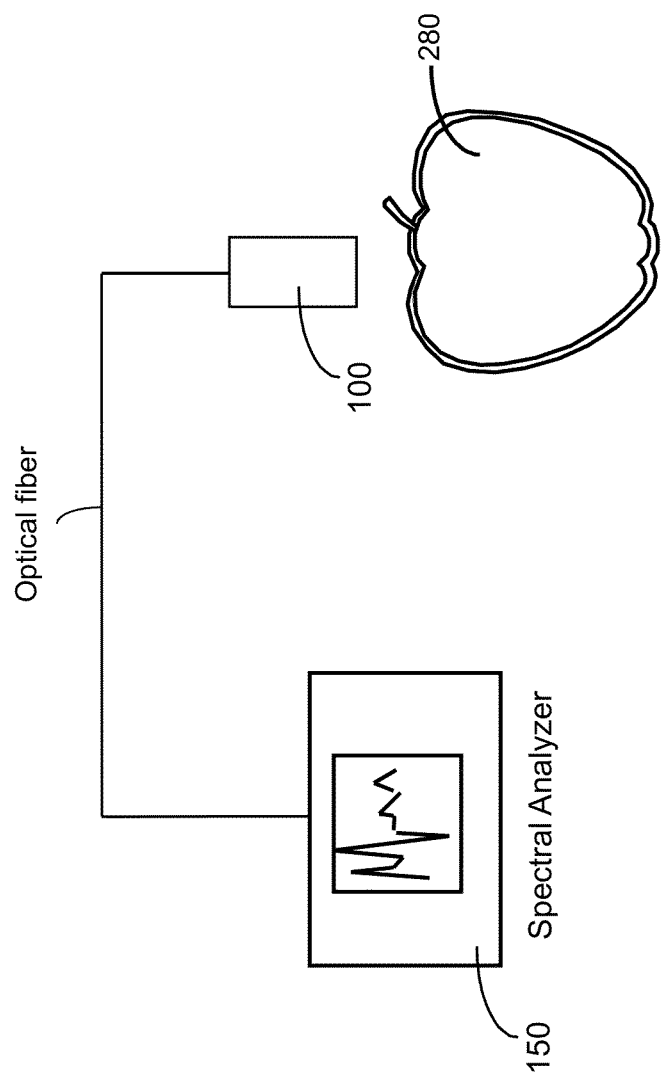
FIG. 6A is a schematic diagram for food safety inspection using a Raman scattering probe.

FIG. 6A is schematic diagram of applying the technology of Surface-Enhance Raman Scattering using a sensor to monitor substances for inspecting quality and safety of foods. A light scattering probe 100 is placed close to a food item 280, i.e., edible oil, an apple or different fruits, vegetables or other food items that could be contaminated through transportations, food processing, or even food growth process. The molecules of residue pesticide, veterinary drug, hormone, fertilizer, illegal food additive, migrated from or on a food packaging material, or other contaminations are drawn into the light scattering probe 100. The molecules of the harmful substances can be adsorbed to nano structured surfaces such as nano particles in a colloidal solution or a microchip containing a nano surface structure. As described in more detail below, the spectral sensing techniques can include Surface-Enhance Raman spectroscopy, normal Raman spectroscopy, Fluorescence spectroscopy, etc.

Figure 6B:
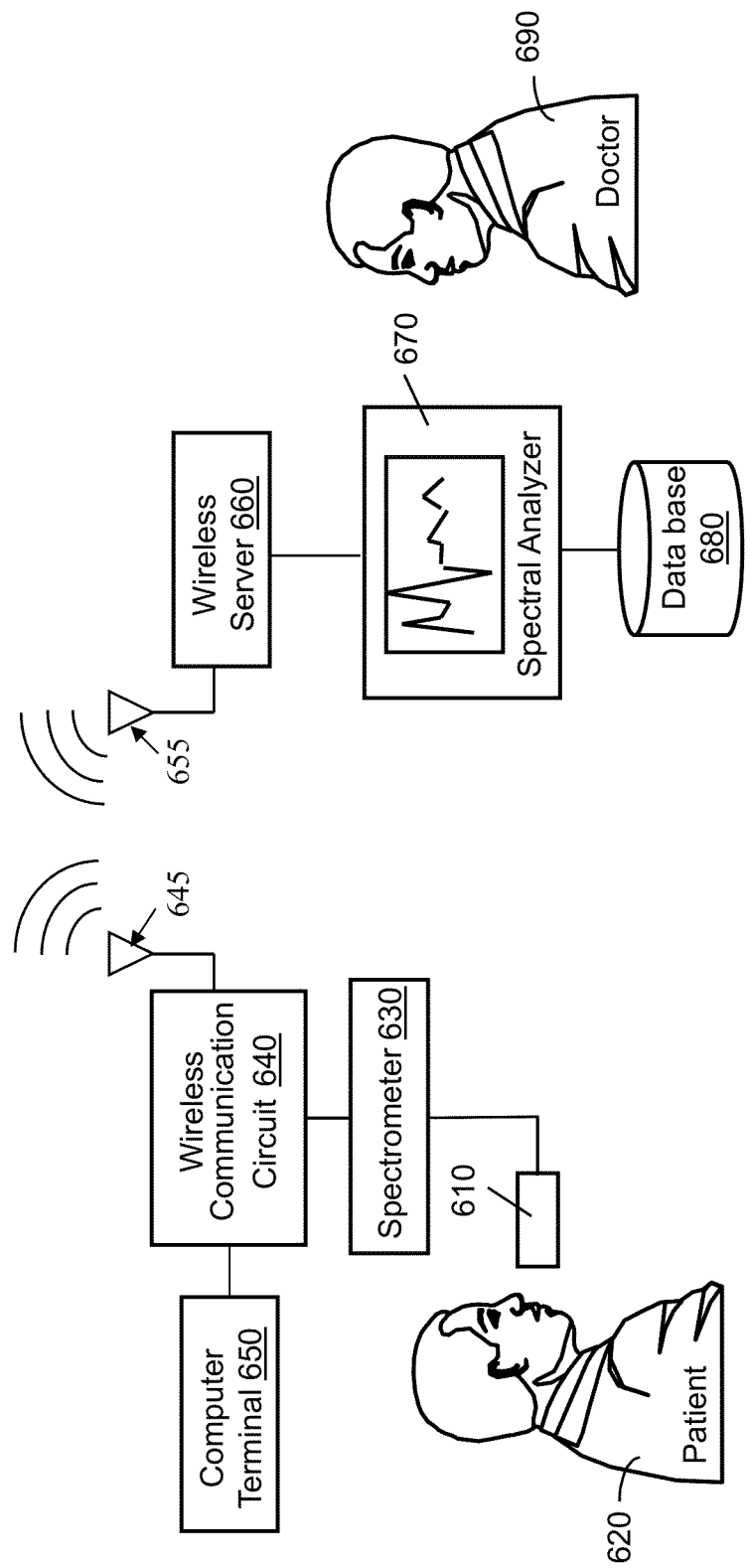
FIG. 6B illustrates an exemplified system for remote disease diagnosis and biomedical detection using a Raman scattering probe.

FIG. 6B shows an application of disclosed Raman spectral technique to monitor substances for early disease detection and diagnosis. A doctor can remotely monitor and diagnose a patient at home or hospital. The probe assembly 610 is placed near a patient 620 for carrying out a physical examination, a check-up from recuperation from a sickness, or for disease diagnosis. Human breathed air can carry special chemicals such as alkenes and benzene derivatives. If a person under screening has a disease such as cancers including but not limited to lung cancer, breast cancer, liver cancer, pancreas cancer, ovarian cancer, etc., the disclosed Raman sensing systems and methods can fingerprint those chemicals in breath test to identify some special diseases such as cancers. The patient blows the outpoured breath-air to the probe assembly 610. The sensor in probe assembly receives the inlet air for generating a scattered light corresponding to the molecules contained in the airflow from a patient or a breath air sample provider. Spectral data of the scattered light is produced by a spectrometer 630. A wireless communication circuit 640 can convert the spectral data into an RF signals which can be transmitted in a wireless signal by an antenna 645. The wireless signal can also include information (e.g., patient's name, identification, etc.) about the patient 620. A computer terminal 650 coupled to the wireless communication circuit 640 can display information received from a doctor's office and allows the patient to input information to be transmitted to the doctor's office. Similar application can be done by testing a person or animal's body fluid.

An antenna 655 at a doctor or a health advisor's office receives the wireless signal or wireless signal from a plurality of patients at a distance. A wireless server 660 can down convert the wireless signal and extract the spectral data and other information about the patient or input by the patient. The spectral data is analyzed by a spectral analyzer 670 using spectral signatures stored in a data base 680. The spectral signatures can indicate a plurality of predetermined diseases. The determination of a spectral signal in the spectral data may indicate the patient is carrying the associated disease or has not fully recovered from a previously diagnosed sickness. The signal strength can indicate the severity of the disease suffered by the patient. A doctor 690 can also make a determination about the nature and severity of the disease by visually inspecting the spectral data. The described systems and methods are suitable for early disease diagnosis which disease includes, but not limited to lung cancer, breast cancer, stomach cancer, Liver cirrhosis, failing kidney, ulcer cancer, etc. In case of testing human body fluids, the fluid is dropped on a sensor manually or automatically, or Raman sensing device can be designed to connect to toilet for easy sample collection as smart toilet to timely monitor abnormal signals for disease and drug detection. This application also includes identifying and sorting protein, DNA and RNA. All testing samples in above applications can be placed in contact with a sensor to enhance the sensitivity and intensity of Raman scattering detections. The disclosed trace chemical detection using Raman light scattering can also be applied to other areas, including but not limited to identify cancers, HIV, Alzheimer's disease, Parkinson disease, non-invasively test glucose to monitor diabetes, non-invasive test and evaluate level of carotenoids to monitor antioxidant status for early cancer screening purpose, illicit drug, and so on.

Figure 6C:
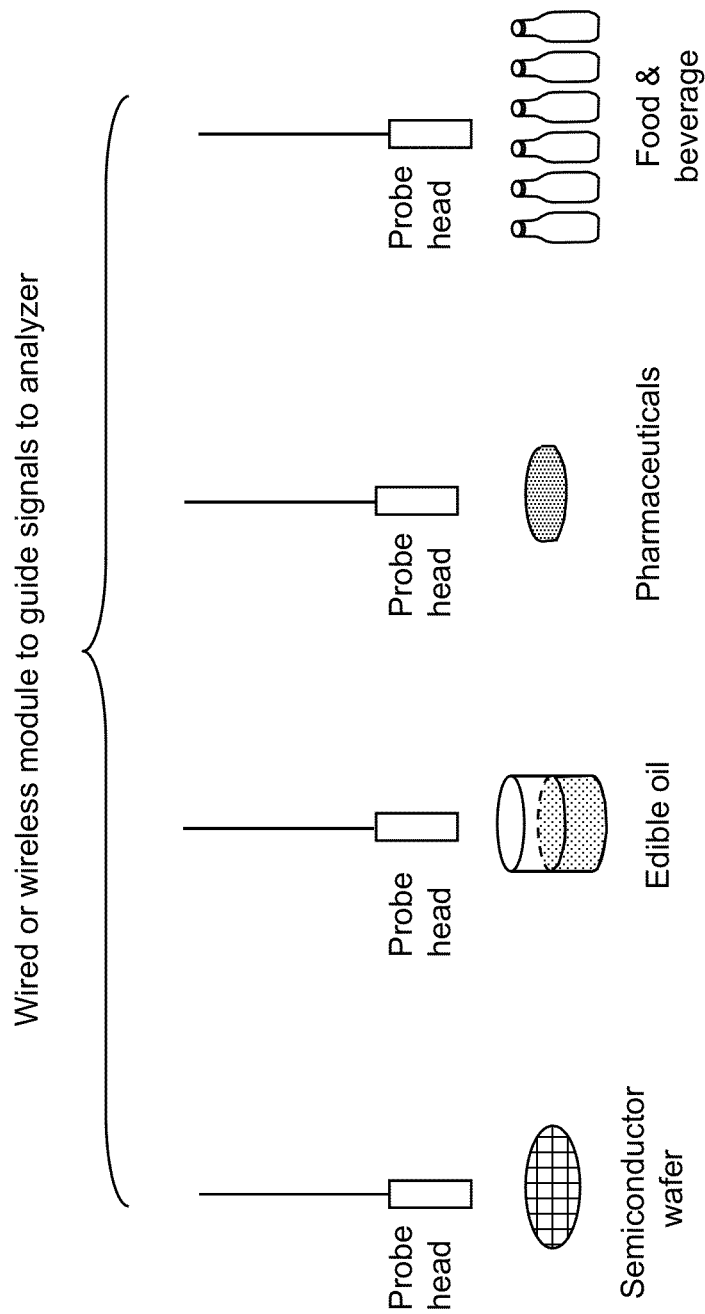
FIG. 6C is a schematic diagram showing quality control and food inspection using a plurality of Raman scattering probes in a multi-channel sensing system.

FIG. 6C is schematic diagram of Raman scattering application in industrial quality control, safety assurance, or food safety in distribution and retail channels. The applications can include in-line monitoring of chemical concentrations in a plurality of wet chemical process line, remotely or stand-alone monitoring of sealed chemical tanks, remote trace chemical detection, semiconductor wafer defect evaluation, and monitoring of the food, fruit and vegetable storage, etc. For example, the food products can include edible oil sampled at different locations. The spectral signals collected by probe heads at a plurality of locations can be fed by optical fibers in multiple channels to a spectral analyzer at a central office, wherein the spectral data are analyzed. The spectral signatures in the spectral data can lead to the identification of harmful substances in the food, drug, a chemical related product, etc.

Figure 6D:
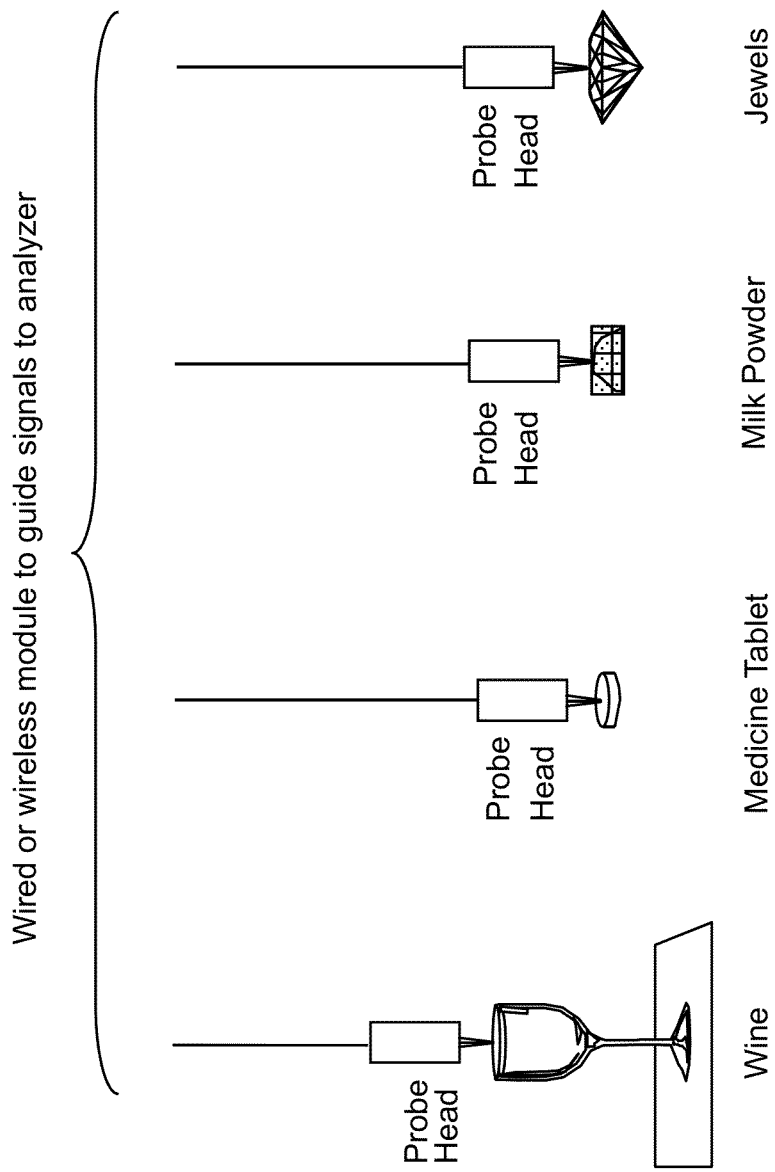
FIG. 6D is a schematic diagram showing detection of counterfeit merchandise, inspection of safety and quality for food and beverages, and drug authentication using a plurality of Raman scattering probes in a multi-channel sensing system.

FIG. 6D is schematic diagram of a multi-channel Raman scattering sensing system that can identify and screen materials for counterfeit merchandise and food safety screening. The applications may include operations such as food, drug and medicine screening, which may or may not involve a nano structured sensor module. The excitation laser beams in the probe heads can directly impinge on samples under test. The scattering light from the tested materials are collected by the probe heads. The Raman spectra of the scattered lights show spectral signatures that can provide indications whether there are illegal additives added to the commercial merchandises. The potential counterfeit merchandise such as milk-based powder, wine, and medical tablets may be placed under the Raman detector as materials under investigation and screen. The spectral signals can be collected from different samples and fed by optical fibers in multiple channels to a spectral analyzer at a central office, wherein the spectral data are analyzed. The applications can be extended to authenticated signatures and currency bills by detecting false signature and false bills by generating Raman scattering spectrum of the signature and dollar bills and compare these spectra with measurements obtained from authenticated signature and dollar bills.

Spectral Sensing Using Nano-Particles

Figure 7:
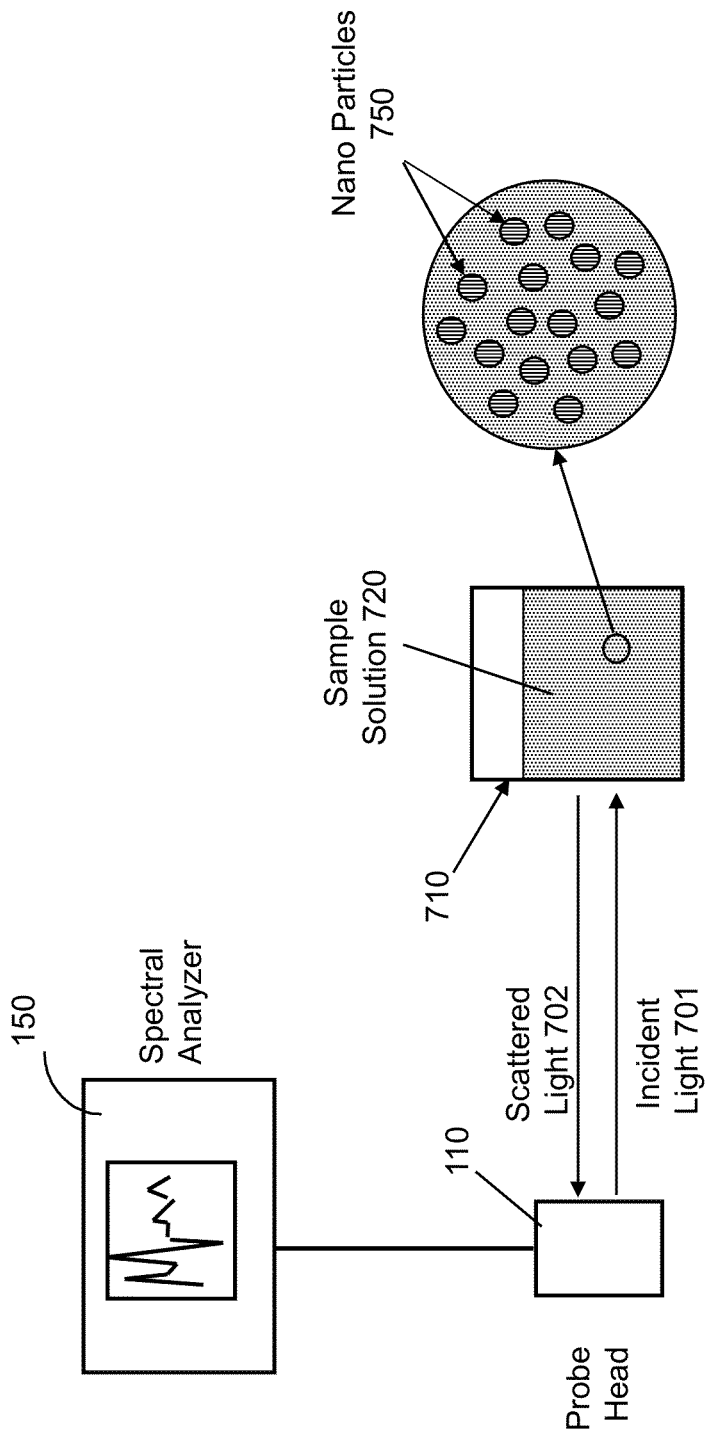
FIG. 7 is a schematic diagram showing the detection of trace chemical or biological substances using a solution containing nano particles and a light scattering probe in accordance to an embodiment of the present application.
Figure 8:
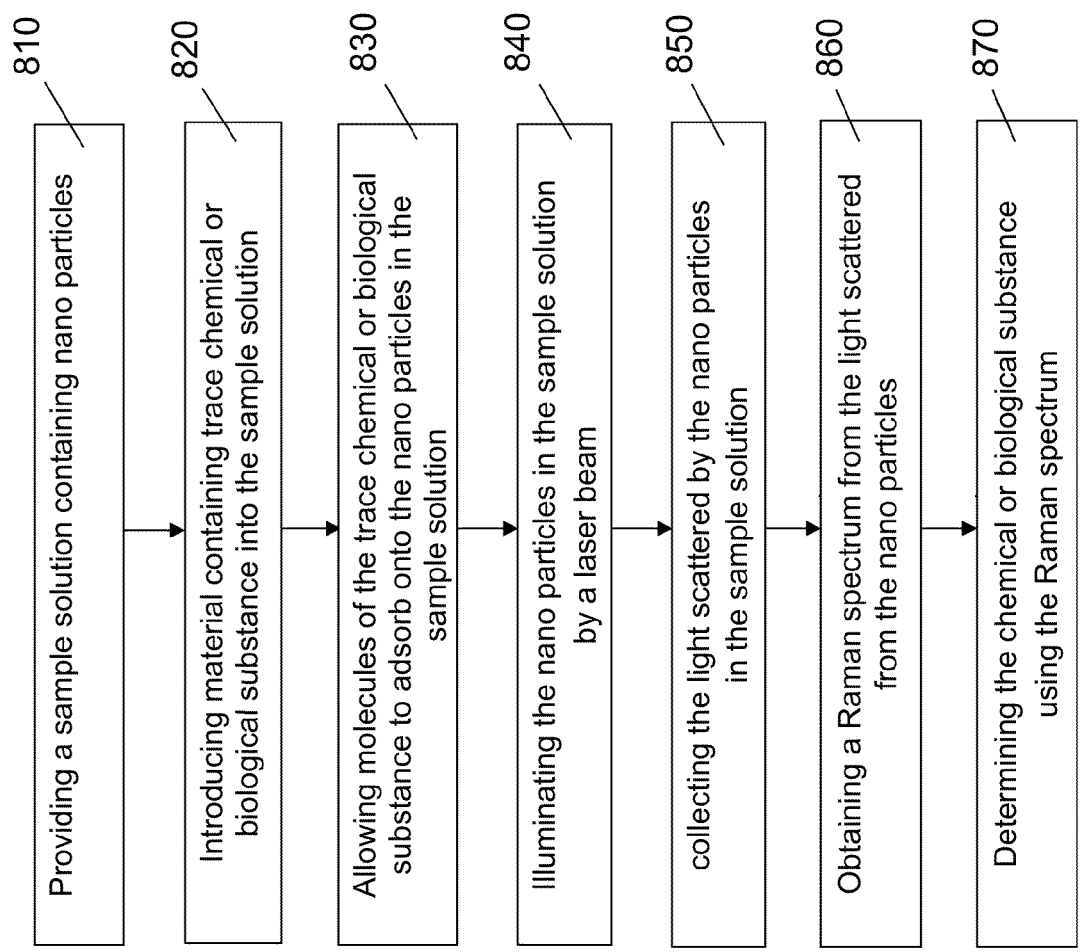
FIG. 8 is flow diagram for detecting trace chemical or biological substance using a solution containing nano particles and a light scattering probe.

In some embodiments, referring to FIGS. 7 and 8, a sample solution 720 is introduced into a container 710 such as an optical vial or a cuvette made by quartz, glass, or plastic materials (step 810). The container 710 can be an optical vial, a beaker, or a transparent test tube, etc. The sample solution 720 also contains nano particles 750. The nano particles 750 can exist in the form of a colloidal suspension in the sample solution 720. A reagent containing the chemical or biological substance is introduced into the sample solution 720 (step 820). The reagent can exist in a solid, a liquid, an aerosol, a sol gel, or a gas form. The reagent is dissolved in the sample solution 720 to allow molecules of the chemical or biological substance to be adsorbed on surfaces of the nano particles 750 (step 830). A probe head 110 (shown in FIG. 1A) emits an incident light 701 (such as a laser beam) to illuminate the nano particles 750 and the chemical or biological substance in the sample solution 720 (step 840). Scattered light 702 from the nano particles 750 and the chemical or biological substance is collected by the probe head 110 (shown in FIG. 1A) (step 850). The output signal from the probe assembly is analyzed by the spectral analyzer 150. As shown in more detail in the examples below, a Raman spectrum is obtained from the scattered light (step 860). Spectral signature(s) in the Raman spectrum can be used to determine the trace chemical or biological substance adsorbed to the nano particles (step 870).

In one aspect of the present disclosure, material compositions of the nano particles 750 in the sample solution 720 are prepared to enhance the intensity of the scattered light 702 and Raman spectral signal from the nano particles. For example, the nano particles 750 include metallic materials such as Al, Ag, Au, Cu, Fe, Co, Ni, Cr, Zn, Sn, Pd, Pt, and their alloys, oxide materials such as titanium oxide, silicon oxide, zinc oxide, etc, silicon, and polymeric materials. The nano particles 750 can be charged in the sample solution 720 to assist the separation between the nano particles and the formation of a colloidal suspension. The nano particles 750 can also include polymers tethered to the particle surfaces to help repel each other in the sample solution 720.

In some embodiments, the nano particles 750 can include a core made of a magnetic material such as $Fe_2O_3$, $Fe_3O_4$, CoMe, or Fe, Co, or Ni contained compound, and a shell of Au wrapped around the magnetic core. The core can have diameters in a range between 1 nm and 500 nm. After the Au shell is formed on the core, the diameter of the core/shell particles can be in a range from about 5 nm to about 50 µm. The magnetism in the cores of the nano particles allows more effective separation and collection of the particles using an external magnetic field. The Au shell can enhance the adsorption of the molecules of the substance to be detected. Furthermore, the magnetic field produced by the magnetic core can enhance resonance and increase signal strength in Raman scattering.

In some embodiments, the nano particles 750 can include a Ag or $SiO_2$ core and a Au shell. In some embodiments, the nano particles 750 can include a Ag or Au core, and $SiO_2$ shell.

In some embodiments, the nano particles 750 can include carbon nano tubes. The diameters of the carbon nano tubes are smaller than 1,000 nm. For example, the diameters of the carbon nano tubes can be from 0.3 nm to 100 nm. Their lengths can be from 5 nm to multiple millimeters. The length-to-diameter ratio of the carbon nano tubes can be as high as 50 million. The carbon nano tubes can have single-walls or multiple walls. The carbon nano tubes can be in the form of Fullerite, a torus, nanobuds, and nanoflowers.

In the presently disclosed systems and methods, when the carbon nano tubes can be placed into the sample solution 720 to form a suspension of nano particles in which the reagent is added. The carbon nano tubes can also be introduced on a substantially flat surface or a surface already formed with nano structures. A reagent is then introduced to such a surface containing the nano carbon tubes. In either case, a laser beam is directed to illuminate the nano carbon tubes and the reagent. Enhanced localized electro-magnetic field can assist charge transfer between molecules of the targeted chemical or biological substances, which results in enhanced Raman spectral signal.

In another aspect of the present disclosure, the nano particles 750 can be made of a magnetic or ferromagnetic material such as Iron (Fe), Cobalt (Co), and Nickel (Ni), or Fe, Co Ni containing compounds, such as alloy or oxide of Fe, Co, Ni, which can enhance the Raman spectral signal by applying an electrical field, a magnetic field, or an electro-magnetic field to the sample solution 720. The electrical field, the magnetic field, or the electro-magnetic field can be static or alternating.

In another aspect of the present disclosure, the sample solution 720 can include a mixture of nano particles of different material compositions. For example, the nano particles can include a mixture of silicon nano or micro-particles and metallic nano particles, or a mixture of silicon nano or micro-particles and polymeric nano particles, or a mixture of silicon nano or micro-particles, metallic nano particle, metallic oxide nano particles, and polymeric nano particles. Raman signal intensity can be enhanced by mixture compositions.

In another aspect of the present disclosure, the solvent in the sample solution 720 is also designed to enhance the light scattering intensity from the nano particles. It was found that ions and especially multi-valence ions can significantly enhance the signal intensity of the Raman signal. An ionic material can thus be added to the sample solution 720. Examples of ions that the ionic material carries to the sample solution 720 can include $Na^+$, $K^+$, $Li^+$, $Ca^{+2}$, $Ba^{+2}$, $Sr^{+2}$, $Mg^{+2}$, $Mn^{+2}$, $Al^{+3}$, $Zn^{+2}$, $Sn^{+2}$, $Sn^{+4}$, $F^-$, $Cl^-$, $Br^-$, and $I^-$, and so on. The ions can have mono charge or preferably double or high charges in the sample solution 720. The ions can have positive or negative charges. The sample solution 720 can have an ionic compound, including but not limited to LiF, NaF, LiCl, NaCl, KCl, KI, etc. The ionic concentration can be in a range from 10 µM to saturated level.

Figure 9A:
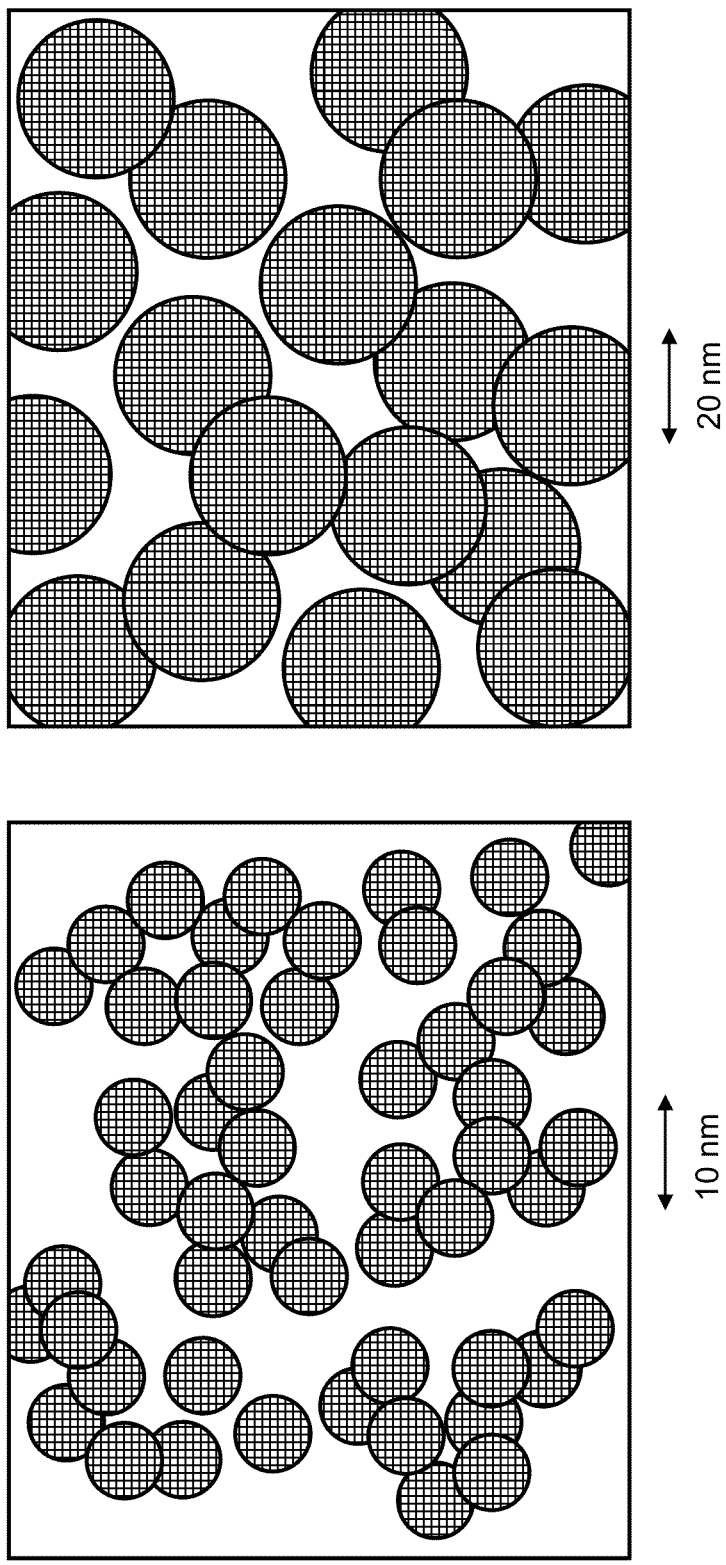
FIG. 9A illustrates exemplified nano particles as observed in micrographs obtained using a scanning electron microscope.
Figure 9B:
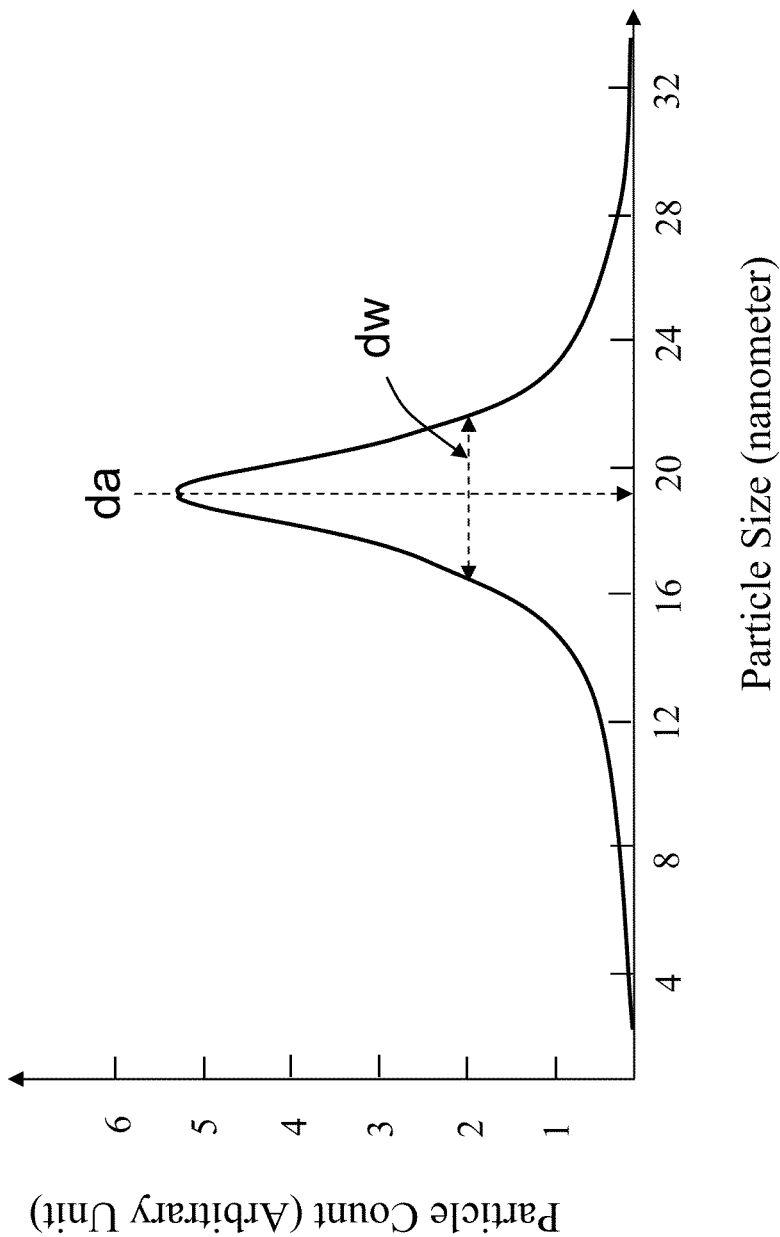
FIG. 9B is an exemplified size distribution of the nano particles in the solution shown in FIG. 7.
Figure 10:
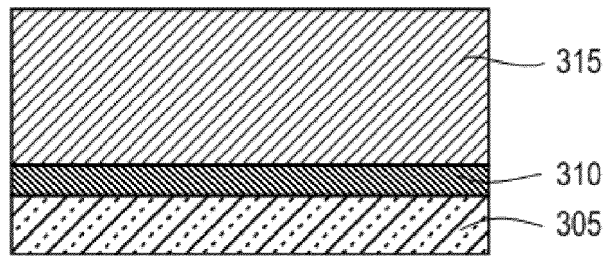
FIG. 10 is a cross-sectional view of a multi-layer layer structure to be used for fabricating a nano structure.
Figure 11B:
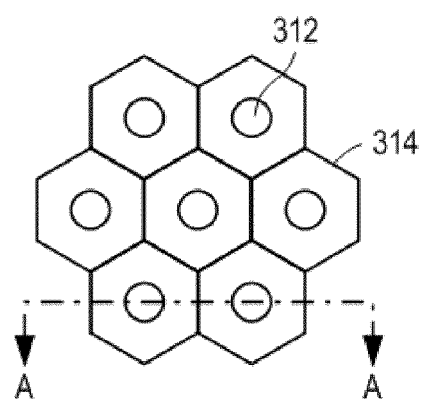
FIG. 11B is a top view of the multi-layer layer structure of FIG. 11A.
Figure 11A:
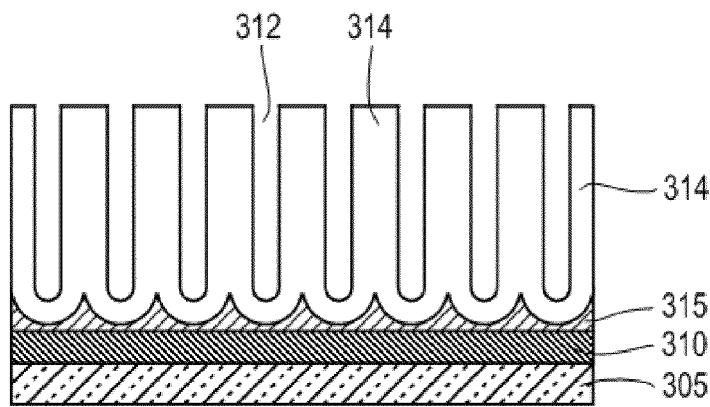
FIG. 11A is a cross-sectional view showing the formation of holes in the multi-layer layer structure of FIG. 10.
Figure 11C:
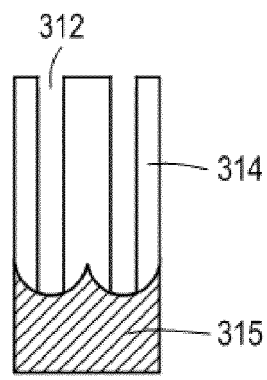
FIG. 11C is a cross-sectional view of the multi-layer layer structure along the line A-A in FIG. 11B.
Figure 12:
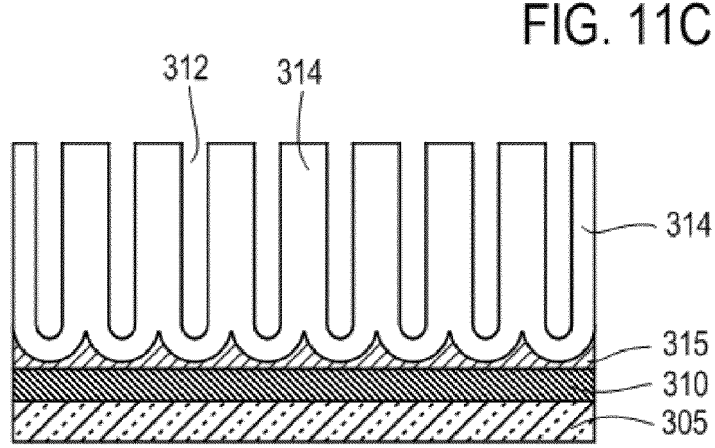
FIG. 12 is a cross-sectional view of the nano structure formed on the multi-layer layer structure after a wet chemical etch or chemical mechanical polishing.

The nano particles 750, as shown in FIG. 9A, can exist in round or irregular shapes. The nano particles can be individually separated and have also group in clusters in the sample solution 720. The nano particles 750 can have a size distribution, as shown in FIG. 9B, which is characterized by an average particle dimension $d_a$ and a particle-dimension distribution width $d_w$ for the particle size distribution. The average particle dimension $d_a$ can range from about 1 nm to about 10,000 nm, or from about 2 nm to about 500 nm. The ratio $d_w/d_a$ can range from about 0.01 to about 3, which defines a quite monodispersed distribution to a polydispersed particle distribution. The ratio $d_w/d_a$ can range from about 0.03 to about 1.

In some embodiments, a sample solution can include nano particles and micro-sliced tumor tissues as the reagent. The temperature of the sample solution can be controlled within a predetermined small range by a TE cooler and heater with temperature variation is smaller than 1° C. or 2° C. The temperature range can be from −20° C. to 60° C., or from 0° C. to 40° C. The sample solution is dried on a substrate surface leaving the nano particles and the reagent on the substrate surface. A laser beam is directed to illuminate on the nano particles and the reagent. The light scattered by the reagent containing the nano particles is collected. A Raman spectrum is obtained from the scattered light. Chemical or biological substance in the reagent can be identified using spectral signatures in the Raman spectrum.

Spectral Sensing Using Nano Surface Structures

In some embodiments, substance containing the trace chemical or biological substance can be introduced onto the surface of a chemical sensor, as shown in FIG. 1, from which an incident light can be scattered and a Raman spectrum can be obtained for material identification. FIGS. 10 to 15 show a series of processing steps for fabricating a nano-structured noble metal surface on the chemical sensor (or the sensor 105 in FIG. 1). A multi-layer structure 302 (FIG. 10) includes a substrate 305, a conductive layer 310, and an aluminum oxide layer 315. The substrate 305 can, for example, be n-type silicon flat wafer (3-8 $\Omega$-cm) or oxidized (30-50 nm $SiO_2$) p-type silicon (5-10 m$\Omega$-cm). The conductive layer 310 can include Ti or Ni and is deposited on the substrate 305 and can be electrically and thermally conductive. The thickness of the conductive layer 310 can be optimized to provide i) adhesion to a subsequently deposited noble metal film, such as Ag, Au, or Cu film, etc., ii) electrical conductive film to apply electrical bias to sensing surface in field application, iii) thermal conductive layer to apply lower temperature of sensing surface. The thickness of the conductive layer 310 can be generally controlled in the range of 10 Å-100,000 Å, typically in the range of 100 Å-1,000 Å.

A metal layer, for example, an aluminum layer 315, is deposited on the conductive layer 310. The aluminum layer 315 can have a purity of 99.99% and thickness in the range of 1.0-10.0 µm. The substrate 305, the conductive layer 310, and the aluminum oxide layer 315 are annealed at 400° C.-500° C. in a $N_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous $Al_2O_3$ layer and barrier layer. A second anodization is carried out to consume all Al metal so that the barrier layer and top porous $Al_2O_3$ layer are right above the conductive metal layer.

Figure 13:
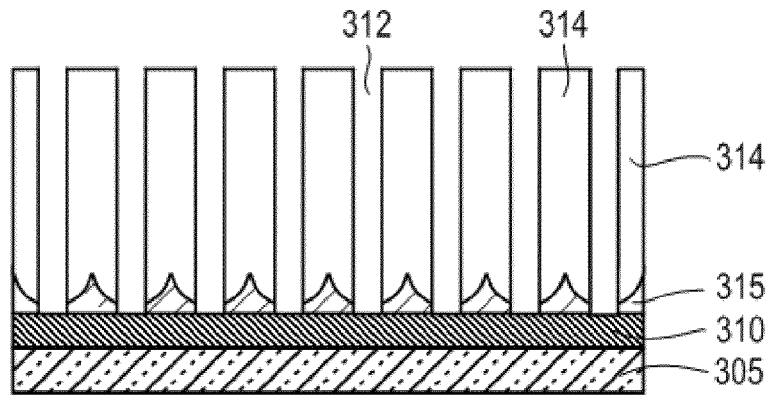
FIG. 13 is a cross-sectional view of the nano structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the inter-pore distance (D) can depend on applied anodization voltage (V), current density (i) and the properties of the electrolyte, and the subsequent pore widening wet etch process.

Figure 14A:
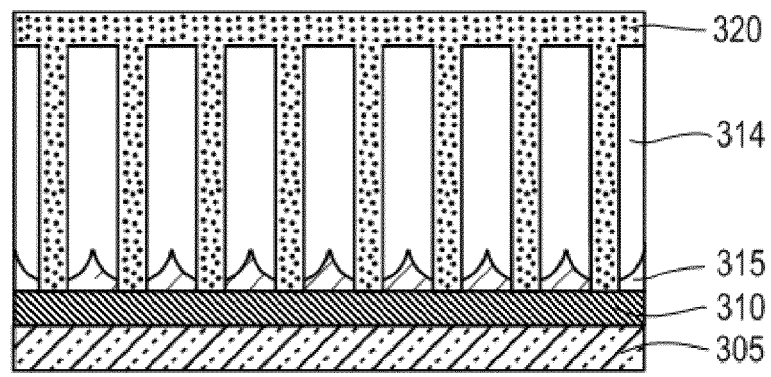
FIG. 14A is a cross-sectional view of the nano structure formed on the multi-layer layer structure after the deposition of a noble metal.
Figure 14B:
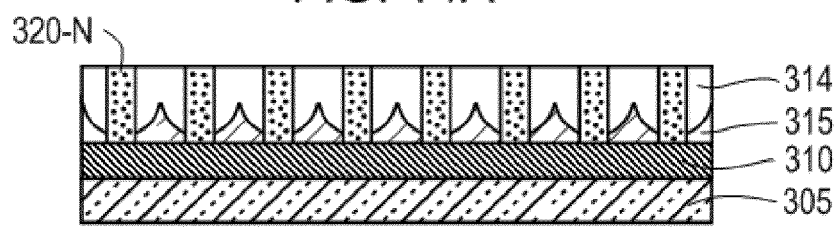
FIG. 14B is a cross-sectional view of the nano structure formed on the multi-layer layer structure after the removal of the noble metal on the top layer.
Figure 15:
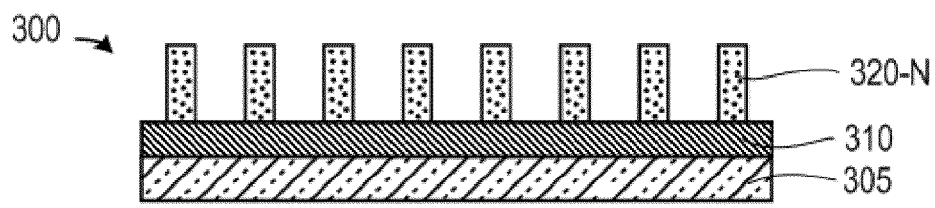
FIG. 15 is a cross-sectional view of the nano structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant or close to constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be an n-type silicon flat wafer (3-8 $\Omega$-cm), or oxidized (30-50 nm $SiO_2$) p-type silicon flat wafers (5-10 m$\Omega$-cm). The thickness of this conductive metal layer 335 can be controlled in the range of 100 Å-1,000 Å. An adhesion layer (which, for example, can be made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection, or higher temperature to clean the sensing surface.

Figure 16A:
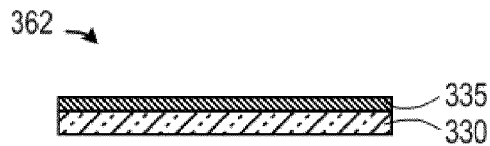
FIGS. 16A-16D, 16G, and 16H are cross-sectional views of the nano structure formed on the multi-layer layer structure after the fabrication process.
Figure 16D:
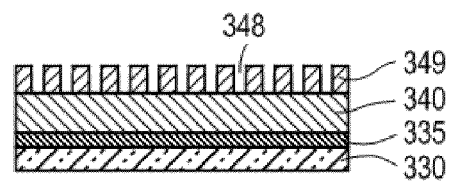
Figure 16B:
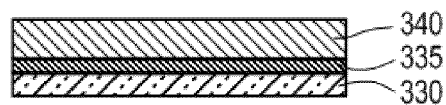

In FIG. 16B, a noble metal layer 340 is deposited on top of the conductive layer 335. The noble metal may be a silver layer, e.g., Ag layer having a thickness of 1 nm-200 nm. In FIG. 16C, a second metal layer 345 is deposited on top of the noble metal layer 340. The second metal layer 345 can include aluminum with a purity level of approximately 99.999% and a thickness in the range of 1.0-10.0 µm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340. Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-sized pores 348 surrounded by wall 349. Alternatively, the etching of the pores 348 can widen the pores 348 so much such they touch each other, which can produce a hexagonal array of quasi-triangle nano rods 349'.

Figure 16G:
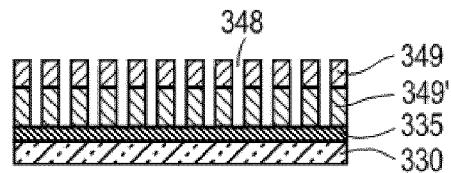
Figure 16C:
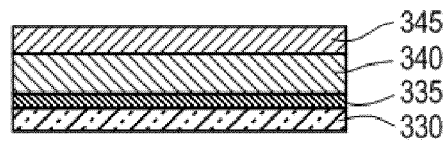
Figure 16H:
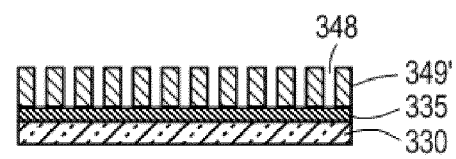
Figure 16F:
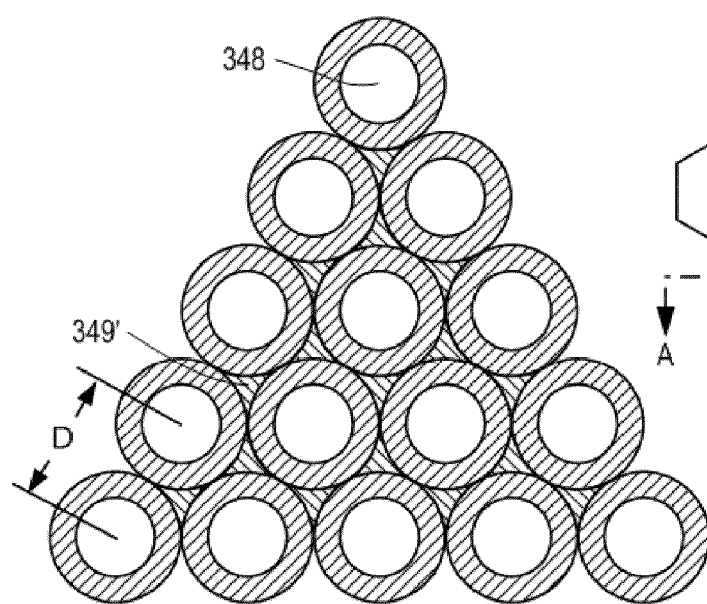
FIGS. 16E and 16F are top views of the nano structure formed on the multi-layer layer structure after the fabrication process.
Figure 16E:
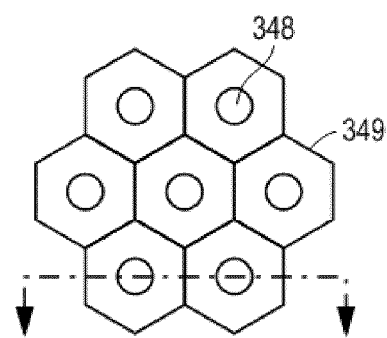

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

In some embodiments, a sensor compatible with FIGS. 1A and 1C can be prepared by introducing nano particles as described above on a structured or substantially unstructured (i.e. flat) substrate, or a sample solution. The trace chemical or biological substance can first be mixed with the nano particles in a solution to allow molecules of the trace chemical or biological substance to be adsorbed onto the nano particles. The sample solution containing the nano particles are then introduced onto the structured or unstructured surface of the chemical sensor. In other words, nano surface structures can be prepared by coating the surface of the sensor 105 by a solution containing a colloidal suspension of nano particles. The nano particles can be formed by a metallic materials (such as Al, Ag, Au, Cu, Fe, Co, Ni, Cr, Zn, Sn, Pd, Pt, and their alloys), oxide material (such as titanium oxide, silicon oxide, zinc oxide, etc), or a polymeric material. Oxide or polymeric particles can be doped with metal ions or coated with a conductive material. The colloidal suspension can include single nano particles or clusters of nano particles. A nano surface structure is formed after the solution applied to the sensor surface. The solution can evaporate, leaving the nano particles adsorbed with the target molecules on the sensor surface.

Healthcare Applications of Nano-Structure Based Spectral Sensing

In some embodiments, diseases can be identified by analyzing Raman spectra obtained from body fluids from a patient using the light scattering probe 100 as described above in relation to FIGS. 1A-2, 6B, 7-9B. A body fluid obtained from an individual person can be directly introduced onto a sensor (e.g., 105 in FIG. 1A) or mixed in a sample solution (e.g., 720 in FIG. 7) containing nano particles. Light scattering and Raman spectral analyses can be conducted as shown in FIGS. 1A-1C or in FIG. 7. Alternatively, the sample solution containing the nano particles can be introduced on a structured or unstructured surface of a sensor, as described above, which is used in subsequent light scattering and Raman spectral analysis.

Figure 17:
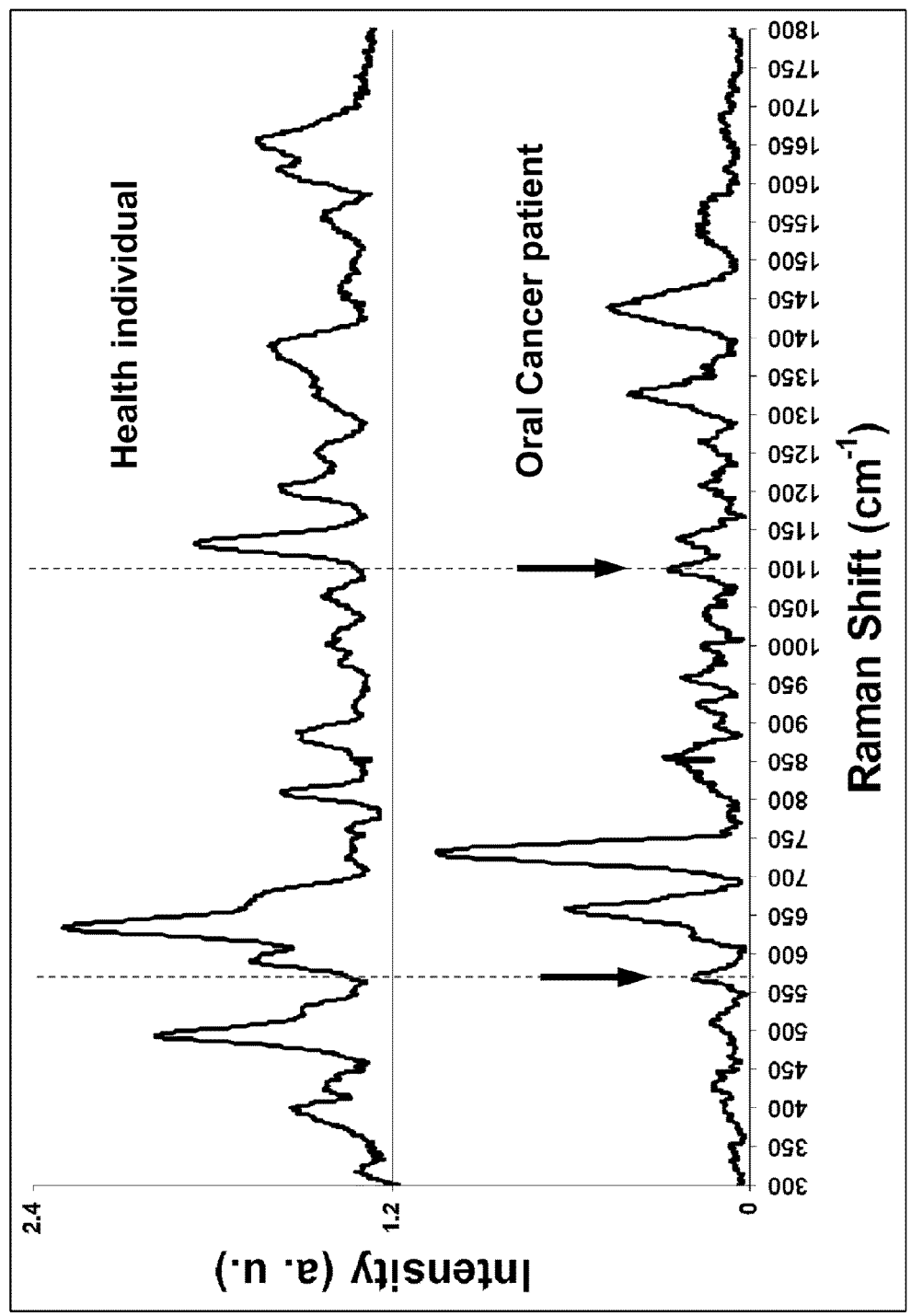
FIG. 17 illustrates an exemplified Raman spectral signature for oral cancer detected in the saliva of an oral cancer patient by the disclosed Raman scattering probe.

Referring to FIG. 17, the Raman spectrum obtained from a saliva sample from an oral cancer patient shows two signature spectral peaks respectively around, for example, 560 $cm^{-1}$ (in the region from 520 $cm^{-1}$ to 580 $cm^{-1}$) and 1100 $cm^{-1}$ (in the region from 1080 $cm^{-1}$ to 1110 $cm^{-1}$) which are absent in a healthy individual without the oral cancer. The signature spectral peaks around 560 $cm^{-1}$ and 1100 $cm^{-1}$ are associated with molecular vibrations for C—S, S—S, O—P—O($PO_2$), C—N, or C—C bonds in, for example, cysteine, ATP, ADP, DNA, RNA, proteins, and other phosphate containing biological compounds. The identification of these spectral signatures can include the steps: a spectral band is first selected at Raman peaks with Raman shift in unit of $cm^{-1}$ (wavenumber) of each spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak is positively identified. The identification of spectral signatures for detecting diseases and drug use can be assigned by statistical analysis and several computation algorithms such as dendrograph classification and Principal Component Analysis. A patient can be diagnosed with oral cancer or at an early stage of an oral cancer if spectral signatures around 560 $cm^{-1}$ and 1100 $cm^{-1}$ are both identified. Appropriate doctors and patients themselves may be alerted for further testing using the same or other types of diagnosis techniques.

Figure 18:
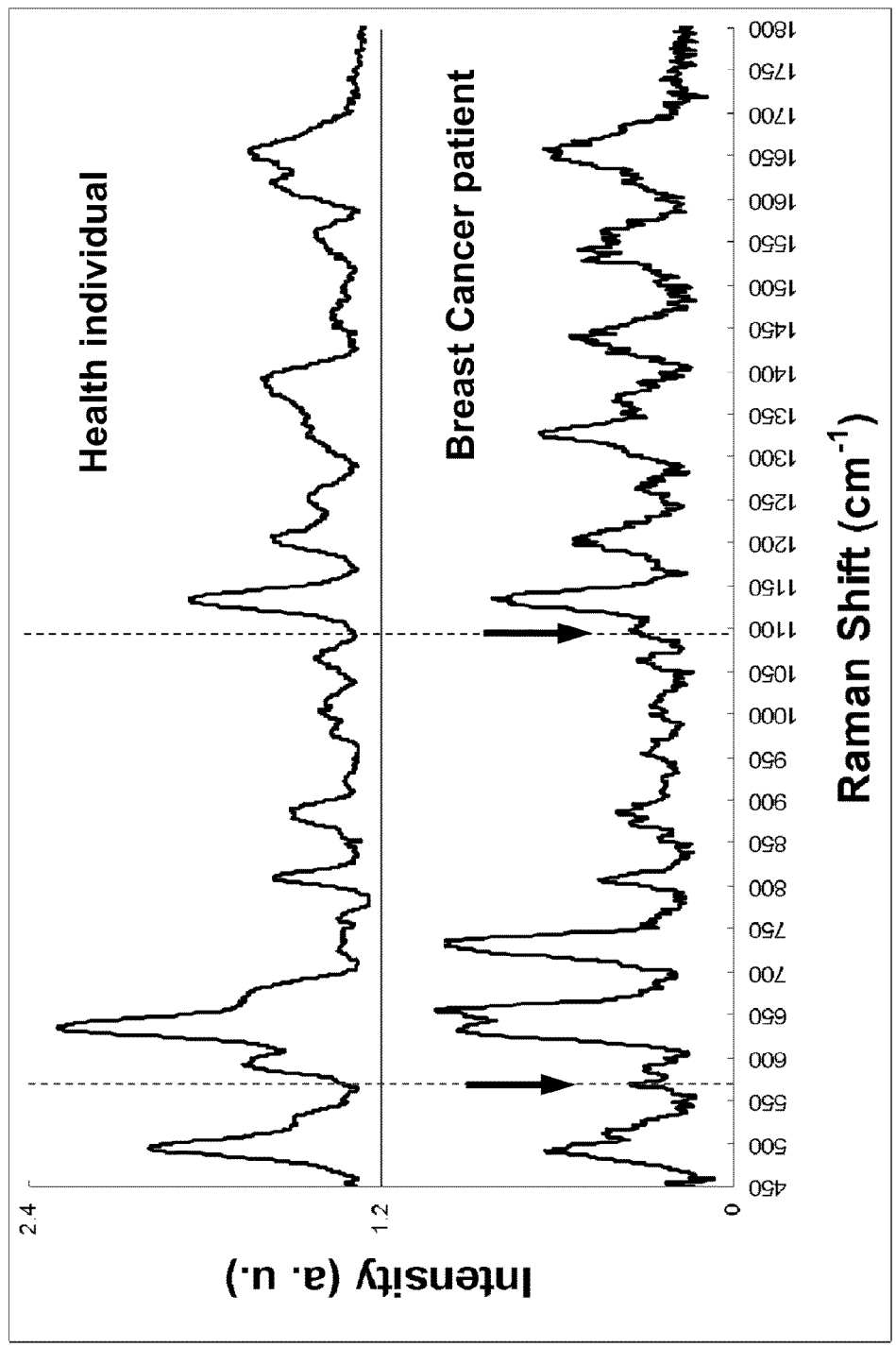
FIG. 18 illustrates an exemplified Raman spectral signature for breast cancer detected in the saliva of a breast cancer patient by the disclosed Raman scattering probe.
Figure 19A:
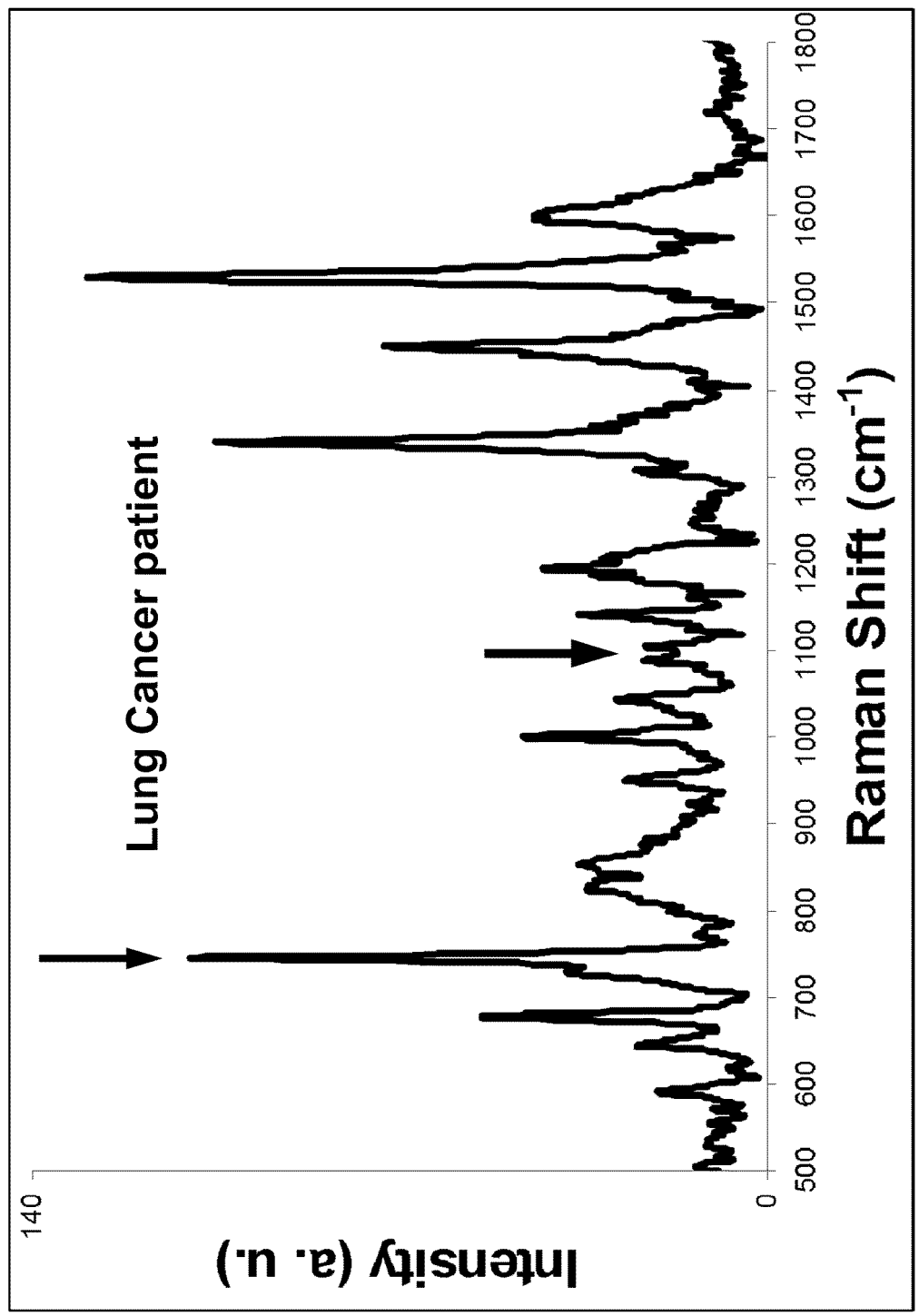
FIGS. 19A and 19B illustrate an exemplified Raman spectral signature for lung cancer detected in both the saliva and the serum of a lung cancer patient using the disclosed Raman scattering probe.
Figure 19B:
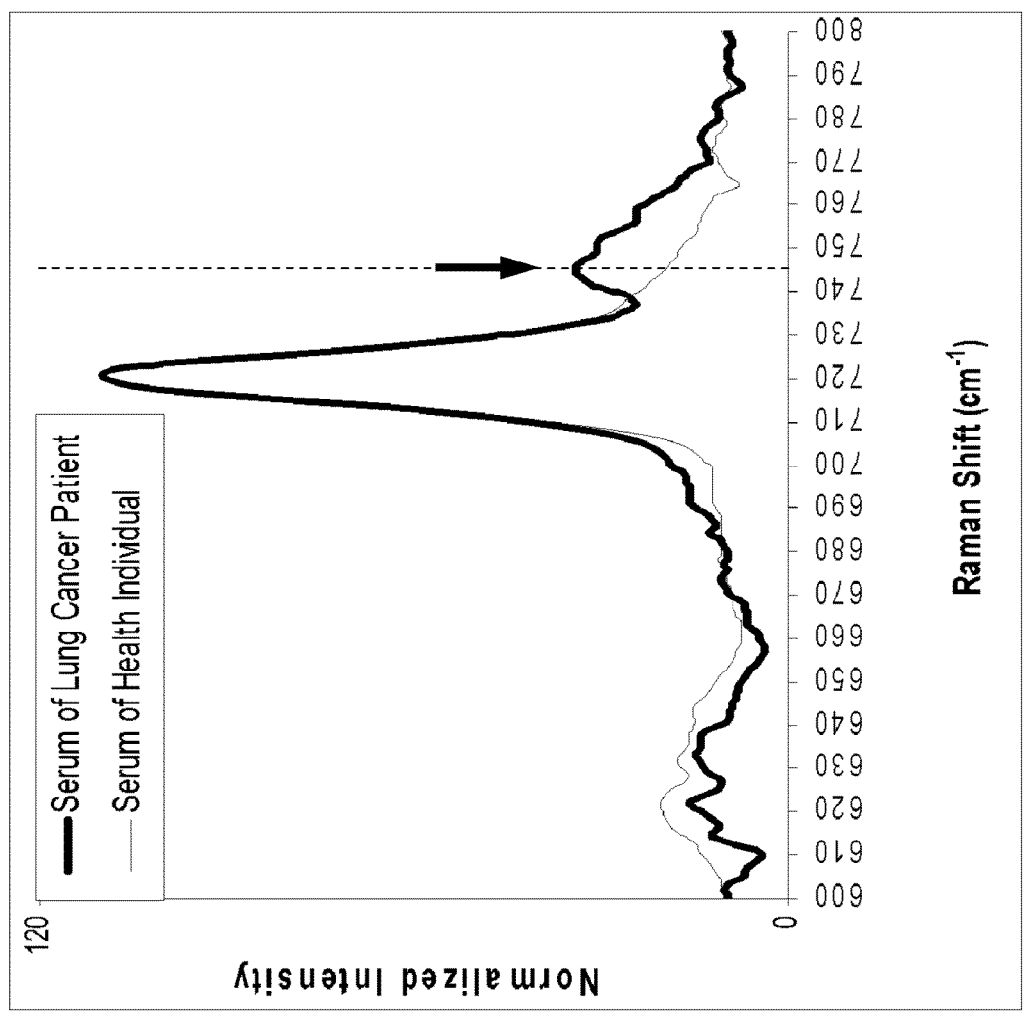
Figure 20:
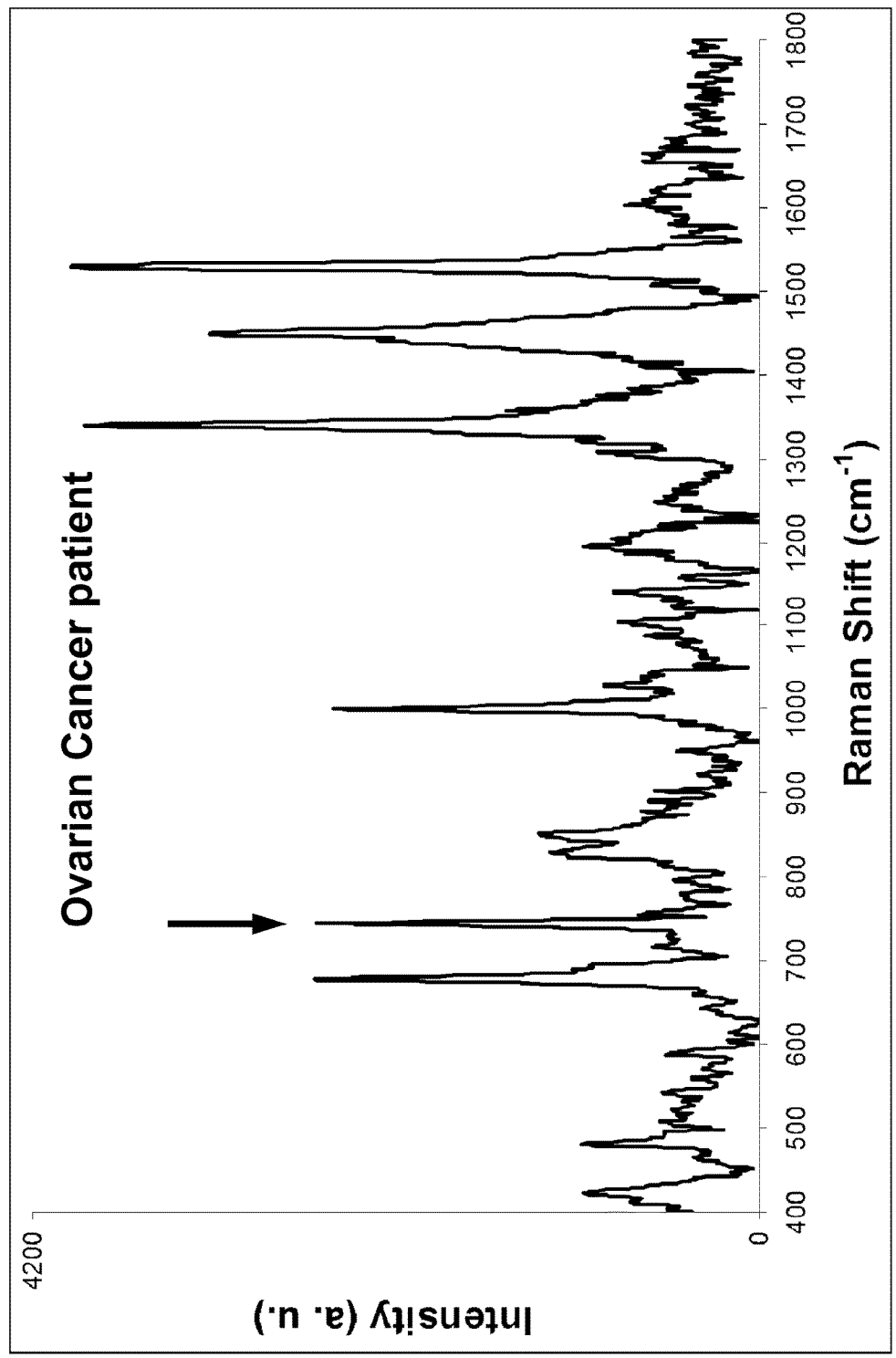
FIG. 20 illustrates an exemplified Raman spectral signature for ovarian cancer detected in the serum of an ovarian cancer patient by the disclosed Raman scattering probe.
Figure 21:
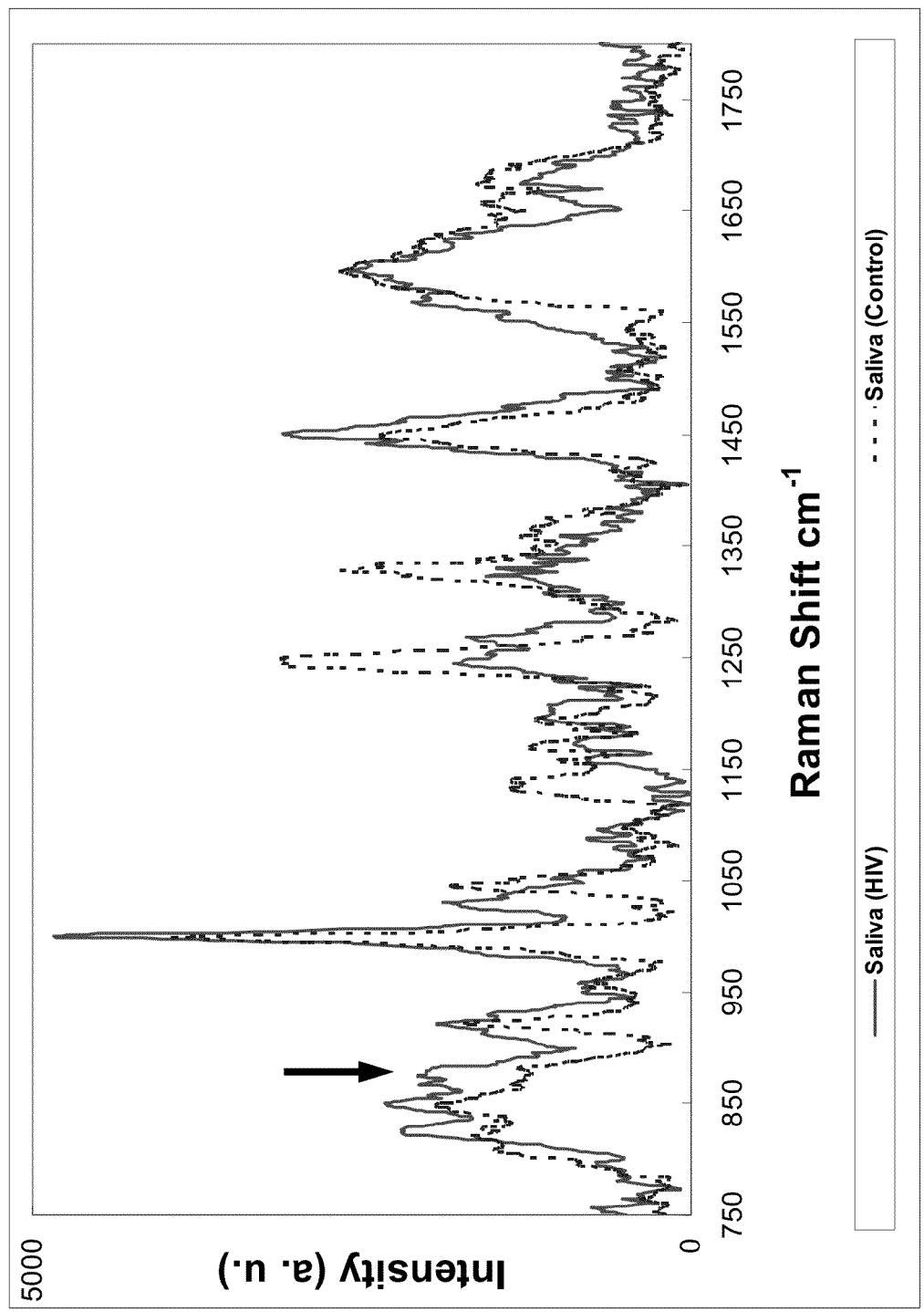
FIG. 21 illustrates an exemplified Raman spectral signature for HIV detected in the saliva of an HIV patient by the disclosed Raman scattering probe.
Figure 22:
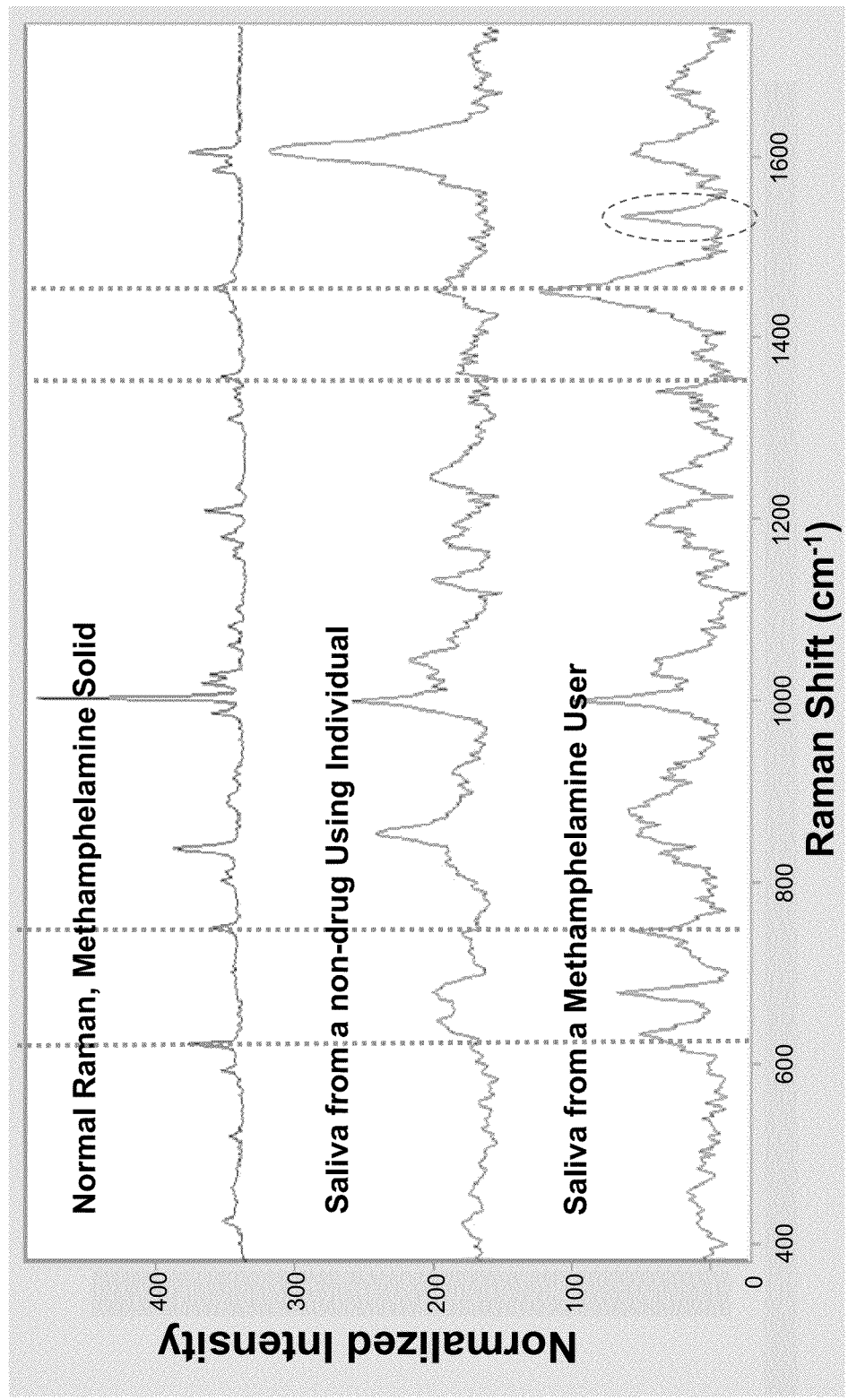
FIG. 22 illustrates an exemplified Raman spectral signature for illicit drug use detected in the saliva of an illicit drug user by the disclosed Raman scattering probe.

The disclosed systems and methods can also be used to estimate glucose level so that to evaluate diabetes status. A signature spectral peak in the region from 1115 $cm^{-1}$ to 1135 $cm^{-1}$, for example, around 1124 $cm^{-1}$, which is associated with molecular vibration of glucose, in a Raman spectrum obtained from a saliva sample from a diabetes patient can provide key evidence for diagnosing diabetes. The intensity, relative intensity or integrated area of this Raman peak, can be used to evaluate glucose concentration of a body fluid from a patient to score potential diabetes level. Similarly, referring to FIGS. 18-20, breast cancer can also show spectral signatures in Raman spectrum obtained from saliva around 560 $cm^{-1}$ and 1100 $cm^{-1}$ (FIG. 18). Saliva and serum samples obtained from lung cancer and ovarian cancer patients can have a Raman spectral signature at around 745 $cm^{-1}$ (in the range from about 740 $cm^{-1}$ to about 760 $cm^{-1}$) (FIGS. 19 and 20). The signature spectral peak around 745 $cm^{-1}$ is associated with molecular vibrations for C—S bonds in phosphate, O—P—O vibration in Z-DNA, T-DNA, or S, N or P contained atomic or molecular groups. HIV can have a spectral signature in Raman spectrum obtained from a serum sample in the region of 865 $cm^{-1}$-885 $cm^{-1}$, for example, around 870 $cm^{-1}$ (FIG. 21). The disclosed systems and methods can also be used to identify illicit drug such as heroin, methamphetamine cocaine, caffeine, morphine, codeine, amphetamine, ephedrine, papaverine, narcotine, acetyl codeine, methamphetamine HCl, ketamine HCl, codeine $H_3PO_4$, meperidine HCl (pethidine), triazolam, secobarbital, hypaconitine, MDMA, etc. FIG. 22 shows Raman spectra from a methamphetamine solid (a type of illicit drug), a saliva sample of a non-drug using individual, and a methamphetamine drug user. The Raman spectrum from a drug-user's saliva sample shows a characteristic peak at around 1030 $cm^{-1}$ and 1535 $cm^{-1}$, which can be used to indicate illicit drug use. The disclosed methods and systems can also be used to detect doping (e.g., hormone) in athletes during international sports competitions such as the Olympic Games.

Figure 23:
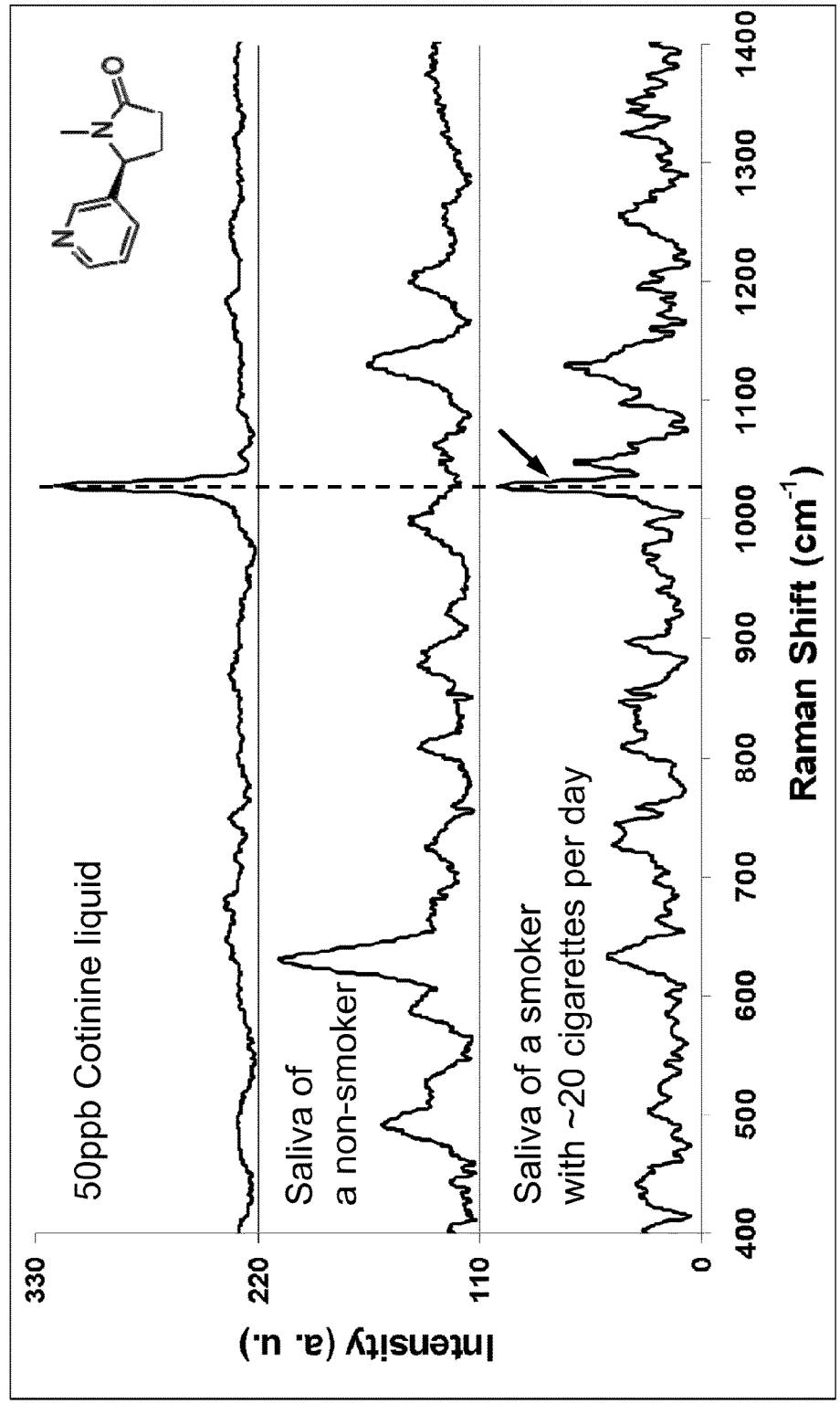
FIG. 23 illustrates an exemplified Raman spectral signature for the smoking status detected in the saliva of a smoker by the disclosed Raman scattering probe, with a comparison of a Raman spectral signature of the cotinine which is the metabolite of nicotine.

Similarly, referring to FIG. 23, smoking status or secondary smoking status can also show spectral signature at around 1029 $cm^{-1}$ in a Raman spectrum obtained from a saliva sample of a smoker, which is absent in a non-smoking healthy individual. The signature spectral peaks around 1029 $cm^{-1}$ is associated with molecular vibration mode of cotinine which is metabolite of nicotine.

Figure 24:
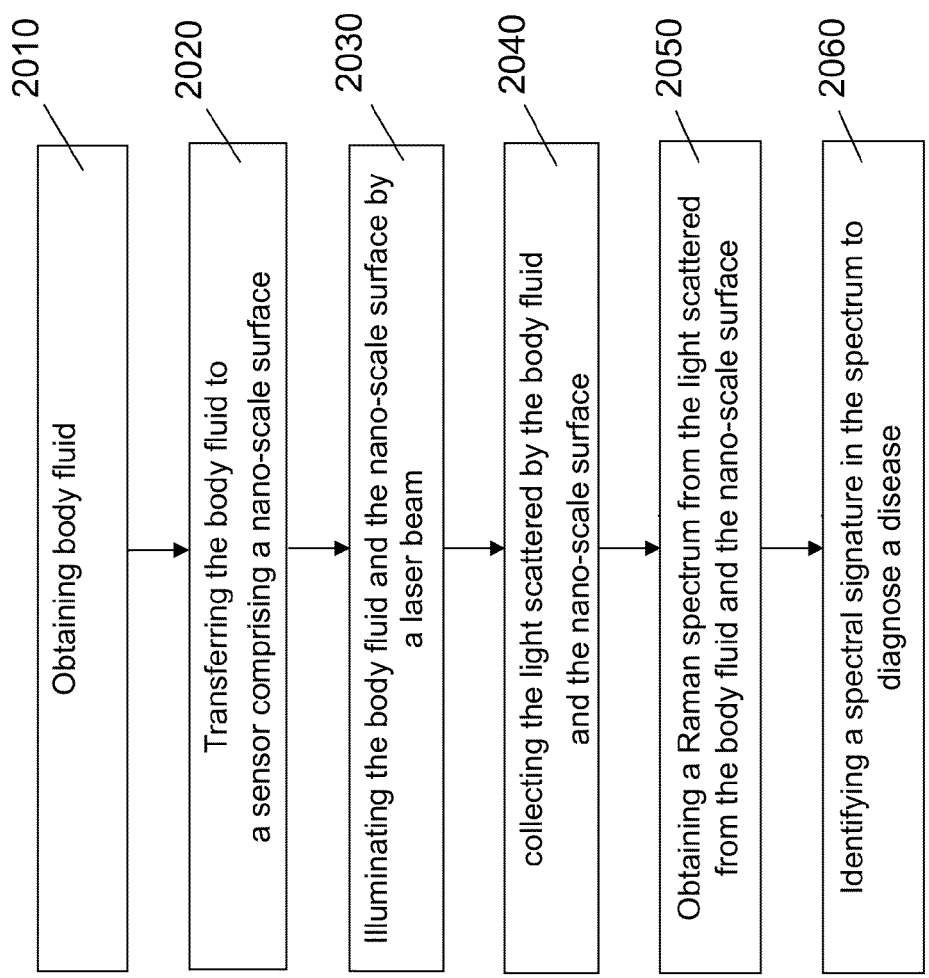
FIG. 24 is a flowchart for non-invasive disease diagnosis using the disclosed Raman scattering probe.

The non-invasive disease detection and diagnosis using the disclosed Raman scattering probe can include one of more of the following steps: referring to FIG. 24, a body fluid is first obtained from a patient or an illicit drug user (step 2010). Due to the high sensitivity of the disclosed Raman scattering sensors, the amount body fluid can be rather small. For example, the volume of the body fluid obtained from the patient can be in a range from about 100 pl to 4 ml. Examples of the body fluid can include blood, saliva, urine, serum, tear, sweat, stomach fluid, hydrothorax, ascites, CSF, sperm, and a secrete body fluid. After centrifuge, the body fluid is next introduced to a nano-scale surface (step 2020). For example, the nano-scale surface can include nano-scale structures on the surface of a sensor. The body fluid can be transferred to the nano-scale surface on the sensor. The body fluid can be left to dry up and remain a dried layer on the sensor surface. In another example, the nano-scale surfaces are provided by the surfaces of nano particles suspended in a solution. The body fluid can be introduced to the solution comprising the nano particles. Molecules in the body fluid are adsorbed to the nano-scale surface. A laser beam is applied to illuminate the nano-scale surface and the molecules adsorbed onto the nano-scale surface (step 2030). Light scattered by the nano-scale surface and the adsorbed molecules is collected (step 2040).

A Raman spectrum is obtained from the scattered light (step 2050). One or more spectral signatures are identified in the spectrum to diagnose a disease (step 2060). Examples of the diseases that can be detected include cancers including but not limited to lung cancer, breast cancer, stomach cancer, esophageal cancer, thyroid cancer, larynx cancer, ulcer cancer, ovarian cancer, liver cancer, head and neck cancers, uterus cancer, cervix cancer, oral cancer, leukemia, colon cancer, bladder cancer, prostate cancer, skin cancer, bronchus cancer, and liver cirrhosis, a failing kidney, HIV, and drug addiction. As previously described, the one or more spectral signatures are at predetermined Raman shift in the Raman spectrum. The Raman shifts and the characteristics of the spectral signatures are specific to the disease to be detected. For example, spectral signatures for oral and breast cancers in a saliva sample can be at around 560 $cm^{-1}$ or 1100 $cm^{-1}$. A spectral signature for lung cancer in a serum sample can be at around 745 $cm^{-1}$ in the Raman spectrum. A spectral signature can include a spectral peak. The spectral signature can be identified when the spectral peak is above certain threshold. For example, a signal-to-noise ratio of the spectral peak relative to the noise background can be above 3 for the spectral signature to be positively identified.

It should be noted that the steps illustrated in FIG. 24 is compatible with and can incorporate one or more steps shown in FIG. 8, which involves using a sample solution containing nano particles.

Detecting Unhealthy or Unsanitary Edible Oils

In some embodiments, the above described methods and systems can be applied to the detection of unhealthy or unsanitary edible oils used in food. These oils include waste edible oil, swill oil, oils refined from animal or bird (chicken, duck, etc.) skin (e.g. the skins of pig, cow, veal, chicken, duck, etc.), and oils refined from animal visceral, and repeatedly reused edible (cooking) oil. These oils are referred as "bad oil" in the present application. These unhealthy or unsanitary oils can be detected using the methods and systems as described in relation to FIGS. 1A-24 above. The unhealthy, unsanitary, or adulterated edible oils can be detected using the portable Raman analysis devices described above. The "bad oils" are purported edible oils that contain unhealthy or unsanitary components, and recycled waste cooking oils.

Fresh, unused, and uncooked edible oil or cooking oil is referred as "good oil" in the present application. The "good oils" are typically cold-press processed from portions of plant fruits, which include seeds of plants and vegetables which process temperature is usually not higher than 90° C., typically not higher than 70° C. Examples of "good oils" include coconut oil, corn oil, cotton seed oil, olive oil, grape seed oil, safflower oil, peanut oil, light vegetable seed oil, rapeseed oil, dark vegetable seed oil, sunflower oil, tea oil, palm oil, and soybean oil.

In the present application, the term "edible oil" and "cooking oil" are used synonymously, which include oils used in foods. The "edible oil" and "cooking oil" can be applied to food with or without heating (frying, stir frying, etc.).

A cooking oil sample is first obtained. The sample preparations can be directly analyzed using surface-enhanced Raman spectroscopy and normal Raman spectroscopy as describe in detail below.

The sample preparation can include adding solvents such as Petroleum ether, Ethyl acetate, and Acetonitrile to the cooking oil sample. NaCl, KCl, or KI can also be added. The sample is prepared using physical separation, centrifuge or ultrasonic technique, and chemical extraction method to allow the sample solution to be separated into different phases. A supernatant, clear phase sample solution, and different phase solution at middle or bottom part of the sample tube are used, respectively, for the Raman analyses.

Figure 25:
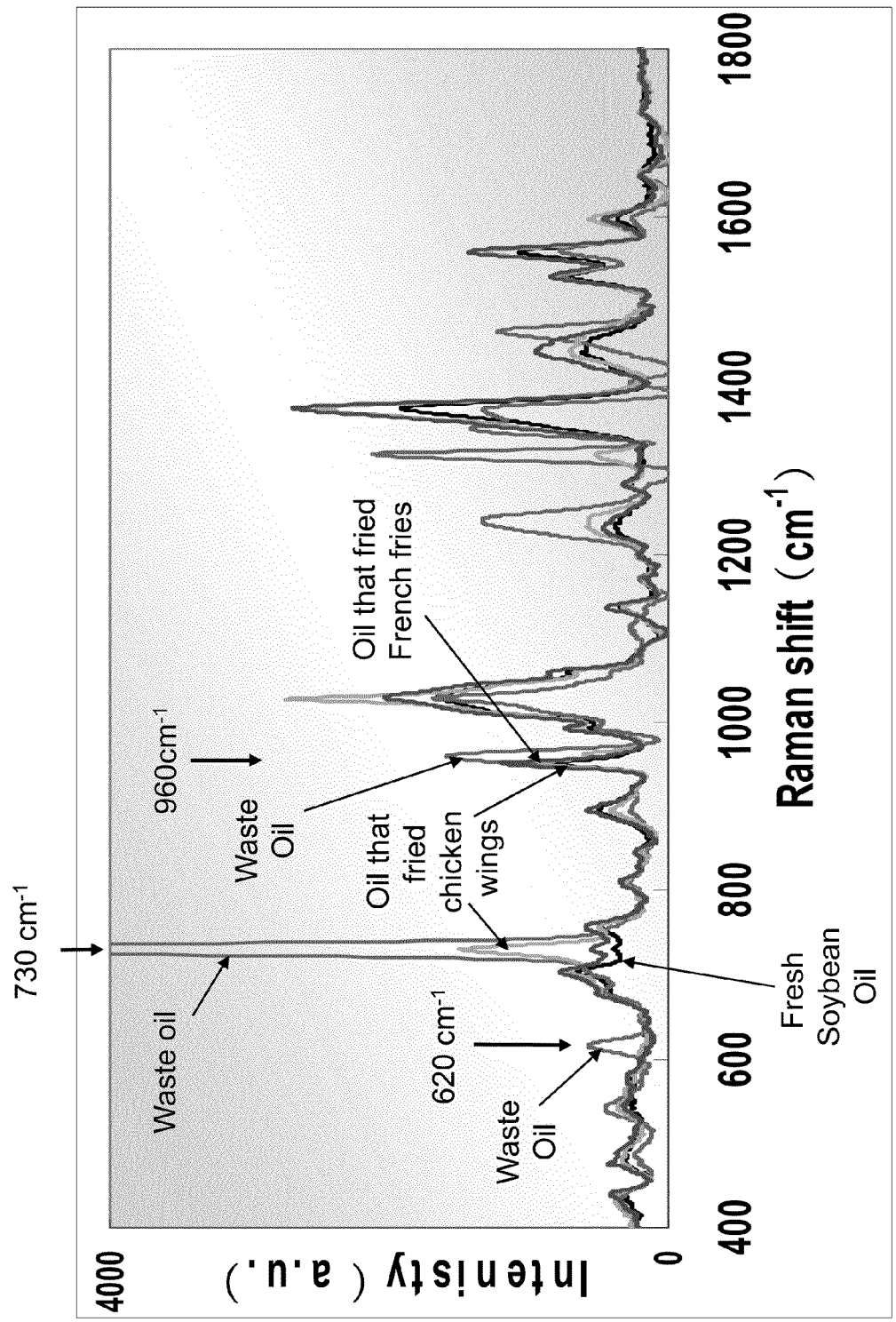
FIG. 25 shows exemplified surface-enhanced Raman spectra comprising spectral signatures for waste edible oil, oil that fried French fries, and oil that fried chicken wings in comparison to the SERS spectrum for a fresh soybean oil.

Specifically, the present inventors have conducted surface-enhanced Raman scattering analyses on different types of oils. Referring to FIG. 25, strong spectral signature (spectral peaks) are detected in these oils due to animal or water product fat about 620 $cm^{-1}$, 730 $cm^{-1}$, 960 $cm^{-1}$, etc. For example, waste edible oil shows strong spectral peaks at about 620 $cm^{-1}$, 730 $cm^{-1}$, or 960 $cm^{-1}$, all significantly stronger than their respective corresponding spectral peak intensities from a fresh soybean oil.

Surface-enhanced Raman scattering can be conducted by introducing the cooking oil sample to nano-scale surface structures to allow molecules of the cooking oil sample to be adsorbed to the nano-scale surface structures. The cooking oil sample and the nano-scale surface structures are illuminated by a laser beam. A surface-enhanced Raman spectrum is obtained from the light scattered by molecules of the cooking oil sample adsorbed to the nano-scale surface structures. Spectral signatures are identified at a predetermined Raman shift to identify the unhealthy, unsanitary, or unsafe content in the cooking oil sample. The nano-scale surface structures can for example be provided by nano particles suspended in a solution, nano particles on a substrate surface, or a nano structured surface. The cooking oil sample is introduced to the nano particles in a solution, or on the nano structured surface of a substrate such as a sensing chip. The nano particles can include a magnetic or ferromagnetic material such as iron, cobalt, and nickel. An electrical field, a magnetic field, or an electro-magnetic field can be applied to the sample solution, or a sensing chip, when the scattered light is collected.

Figure 26:
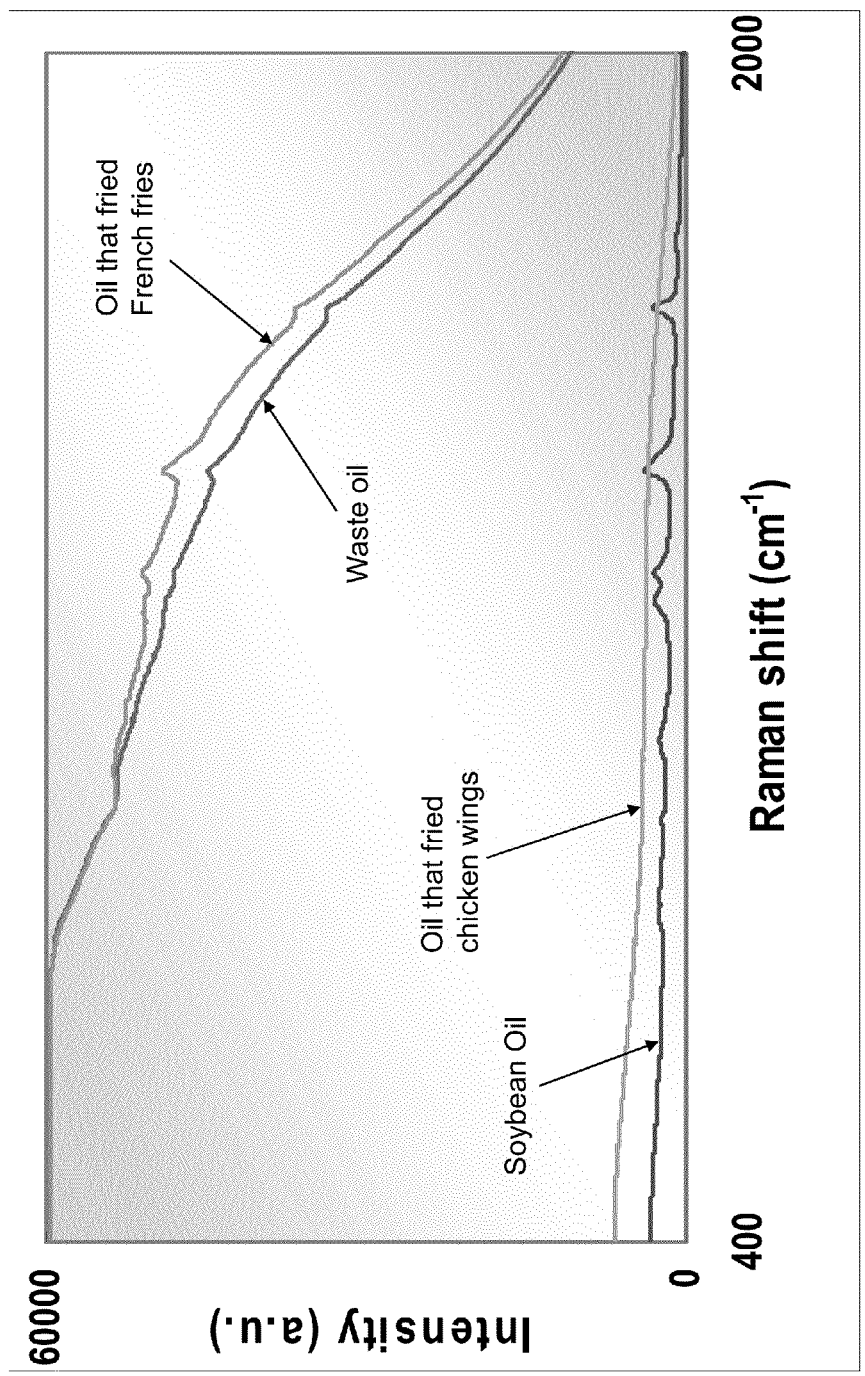
FIG. 26 shows Raman spectra obtained from oil samples including fresh soybean oil, an oil that repeatedly fried chicken wings, a waste oil, and an oil that repeatedly fried French fries.

Referring to FIG. 26, the Raman signal background in a normal Raman spectral region from 100-3300 $cm^{-1}$ is obtained using a 785 nm incident laser beam from different oil samples including fresh soybean oil, an oil that repeatedly deep fried chicken wings, a waste oil, and an oil that repeatedly fried French fries. It is observed that the waste oil and the oil that repeatedly fried French fries have significantly increased fluorescence (or photoluminescence) backgrounds from detected samples comparing to that of the fresh soybean oil, presumably caused by the repeated oxidations and an increase in the polarization in the oil molecules under high temperature condition, for example, near or above the smoking point of the oils. Table I below lists the smoke point of typically used edible oils.

TABLE I

Smoke points of common edible oils.

| Name of an Edible Oil | Smoke Point (° F./° C.) |
|---|---|
| Butter | 300° F./150° C. |
| Coconut Oil | 350° F./175° C. |
| Corn Oil | 450° F./230° C. |
| Cotton Seed Oil | 420° F./215° C. |
| Lard | 375° F./190° C. |
| Olive Oil | 375° F./190° C. |
| Grape Seed Oil | 478° F./248° C. |

TABLE I-continued

Smoke points of common edible oils.

| Name of an Edible Oil | Smoke Point (° F./° C.) |
| --- | --- |
| Peanut Oil | 440° F./225° C. |
| Safflower Oil | 510° F./265° C. |
| Rapeseed Oil | 446° F./230° C. |
| Sesame oil | 430° F./220° C. |
| Tea Oil | 410° F./210° C. |
| Palm Oil | 464° F./240° C. |
| Soybean Oil | 495° F./257° C. |
| Sunflower Oil | 440° F./225° C. |

As described in more detail below, the Raman spectral intensity can be referenced by the fluorescence background in the same spectral range as Raman spectrum to classify and identify "bad oils" and "good oils".

An olive oil is mixed with lard at different concentrations. Raman spectra from these oil mixtures and a fresh pure olive oil are compared in FIG. 27. A strong spectral signature is observed at around 730 cm$^{-1}$ with increased pork fat concentration corresponding to stronger spectral signatures. Thus the concentration of an unhealthy, unsanitary, or unsafe content can be determined in the edible oil sample using the intensity (or height or area, etc.) of the first spectral signatures in the Raman spectrum. Alternatively, one can carry out qualitative inspection to tell whether the inspected sample includes lard component, or not, based on above mentioned method.

Figure 28:
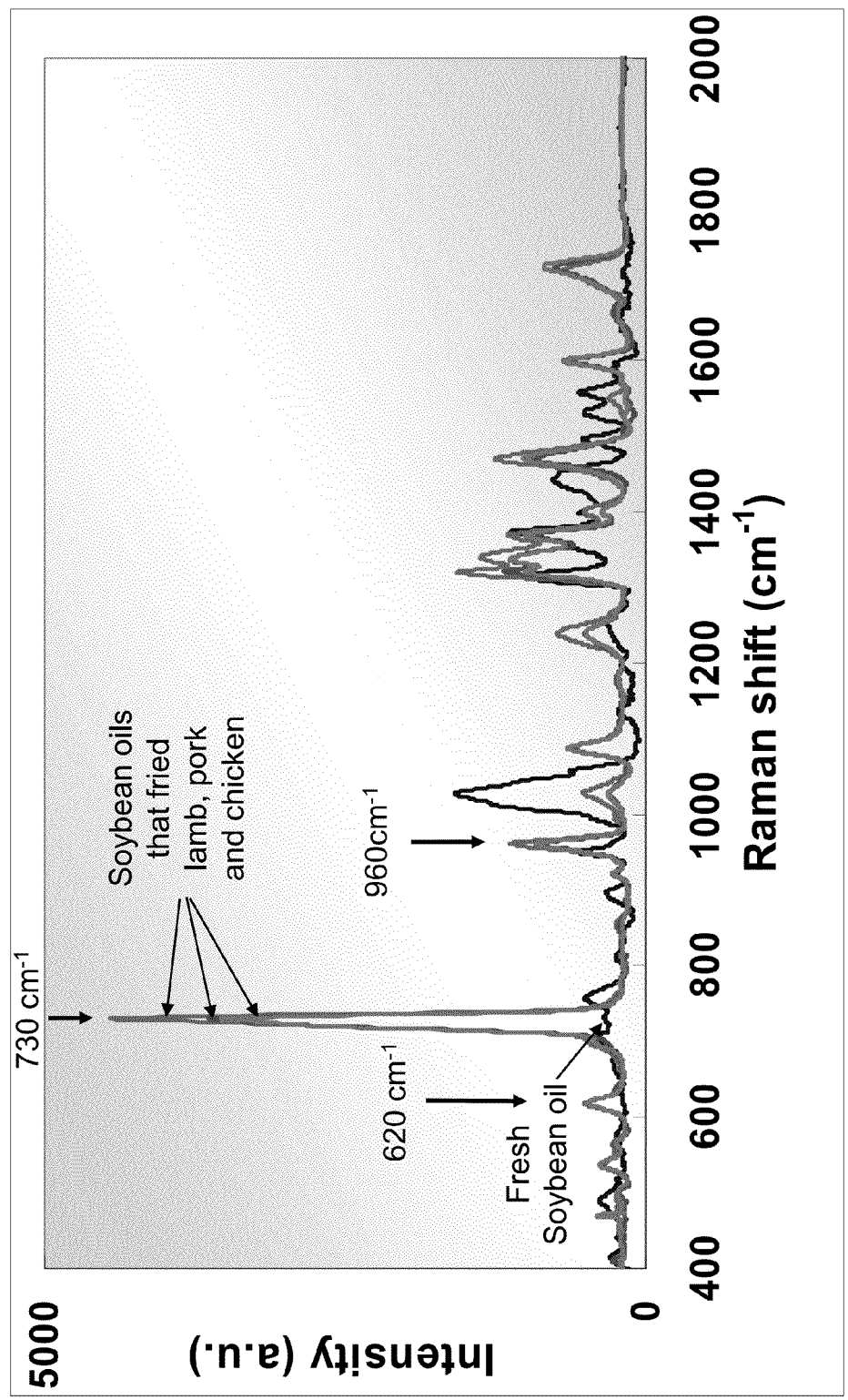
FIG. 28 shows Raman spectra obtained from fresh cooking oil, and cooking oils having repeatedly fried lamb, chicken, and pork.

FIG. 28 shows Raman spectra obtained from a fresh cooking oil made from a mixture of plant-related oils, and cooking oils having been used to repeatedly deep fry lamb, chicken, and pork. The cooking oil that have deeply fried lamb, pork and chicken all showed strong spectral peaks at about 620 cm$^{-1}$, 730 cm$^{-1}$, and 960 cm$^{-1}$, comparing to the Raman spectrum obtained from the fresh cooking oil.

Figure 29:
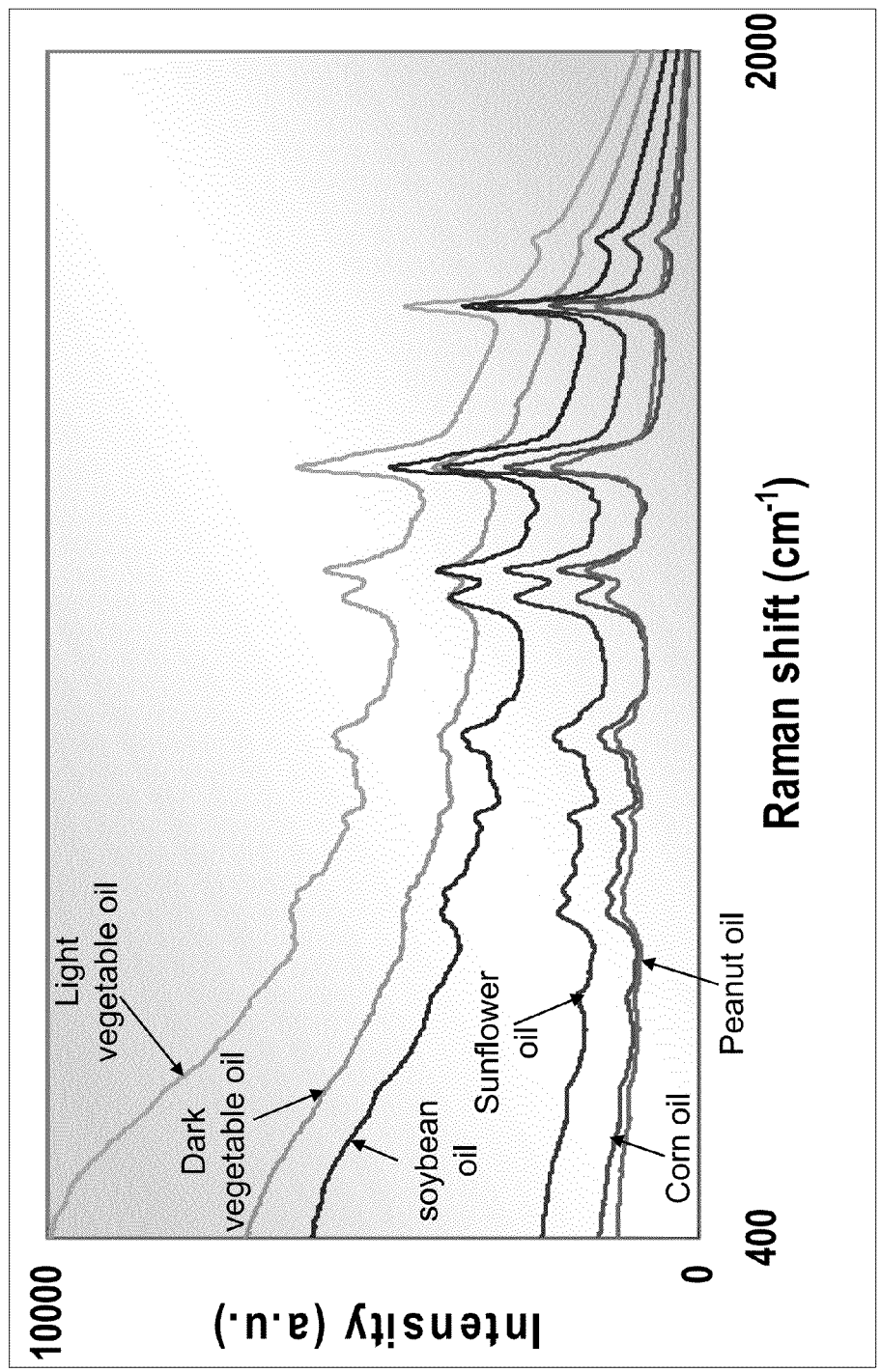
FIG. 29 shows Raman spectra obtained from common plant-related cooking oils.

FIG. 29 shows Raman spectra obtained from common cooking oils including corn oil, peanut oil, light vegetable seed oil, dark vegetable seed oil, sunflower oil, and soybean oil. All the fresh cooking oils show spectral signatures at similar spectral locations and with low fluorescence backgrounds below a threshold value. The threshold value can vary depending on the edible oils, for example, in a range between 2,000 and 30,000 in the spectral range from 250 cm$^{-1}$ to 600 cm$^{-1}$.

Figure 30:
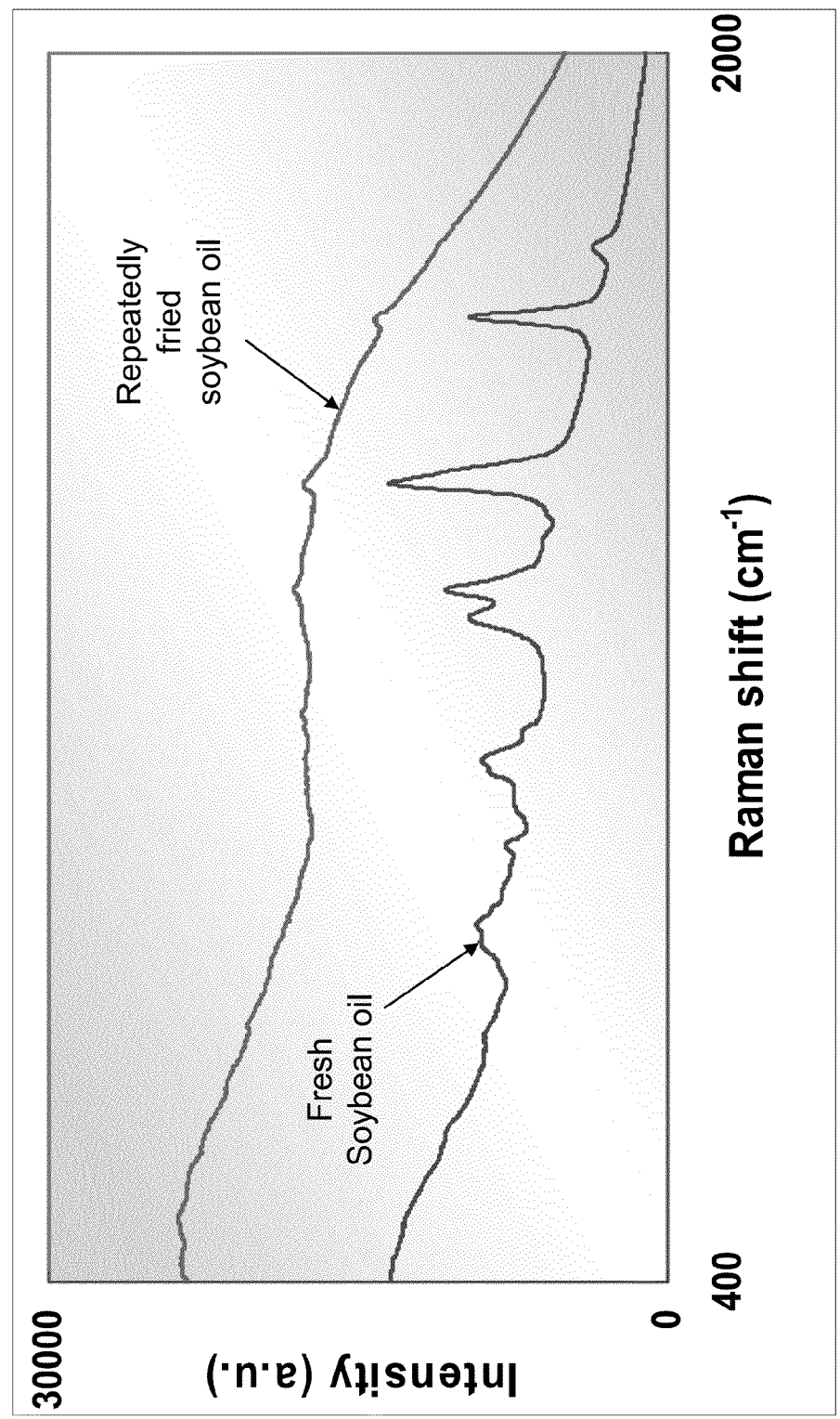
FIG. 30 shows the signal backgrounds of Raman spectra obtained from soybean oil and repeatedly fried soybean oil.

FIG. 30 shows the fluorescence backgrounds of Raman spectra obtained from soybean oil and soybean oil that has been used to repeatedly fry meat. The fresh soybean oil shows the spectral signatures as shown in FIG. 29 and a low fluorescence background below a threshold level. The fresh soybean oil often has a low fluorescence background in the range of 8,000-15,000 counts in the spectral range from 250 cm$^{-1}$ to 600 cm$^{-1}$. The Raman spectrum of the repeatedly fried soybean oil show much higher fluorescence background at the low wave-number range. The differences in the fluorescence backgrounds in Raman spectra can thus be used as a sensitive and effective tool to detect repeatedly fried waste cooking oils. Depending on the nature of the bad oil, the threshold value can vary, for example, in a range between 8,000 and 30,000 in the spectral range from 250 cm$^{-1}$ to 600 cm$^{-1}$. On the other hand, the Raman peaks of the repeatedly fried soybean oil show much weak intensity which some of Raman peaks are barely observed or even non-observable. His is another way to be used as a sensitive and effective tool to detect repeatedly fried waste cooking oils.

In some embodiments, the inspection of cooking oils can include a two-step process. First, the Raman fluorescence spectral backgrounds are used to identify cooking oil samples that may contain repeatedly fried oils. The observation of a low fluorescence background of Raman spectrum is not sufficient to qualify a cooking oil sample (e.g. see oil that deeply fried chicken wings in FIG. 26). Secondly, surface-enhanced Raman spectra of the sample cooking oils are obtained. The spectral signals, especially those at about 620 cm$^{-1}$, 730 cm$^{-1}$, 960 cm$^{-1}$, are used to identify possibly contain certain concentration of fat of an animal, a bird (for example, chicken, duck), fish, water product, and the type of frying history of the oil sample. Using the methods described above, unhealthy, unsanitary, and unsafe cooking oils can be distinguished apart from the fresh plant-related cooking oils. The spectral sensing and analyses can be conducted using systems and processes shown in FIGS. 1A-16.

The Raman signatures correspond to the attributes of the following molecules: Purines, Heterocyclic Aromatic Amines (HAAs), and Polycyclic Aromatic Hydrocarbons (PAHs). HAAs are compounds that from nature muscle meats when exposed to heat during cooking processes. Main chemicals are PhIP and MeIQx. PAHs means the chemical structure contented two or more fused aromatic rings. They mainly present in oil, coal, and tar. There is very low concentration (10-1,000 ppb level) in fried edible oils and animal fats.

It is known that the Purines content in common animal food product is higher than those in fruits and vegetables. For example, Purines content in beef, lamb, pork, and chicken are respectively 400, 270, 480, and 250-310 mg per kilogram. In contrast, Purines content in apple, onion, pumpkins, and tomato are respectively 9, 14, 28, and 42 mg per kilogram. Previous studies have shown that Purines has Raman signatures in the range from 722 to 740 cm$^{-1}$. Thus the spectral signatures observed at about 730 cm$^{-1}$ can be assigned as the bio marker for Purine content, which is carried by animal fat.

Figure 31:
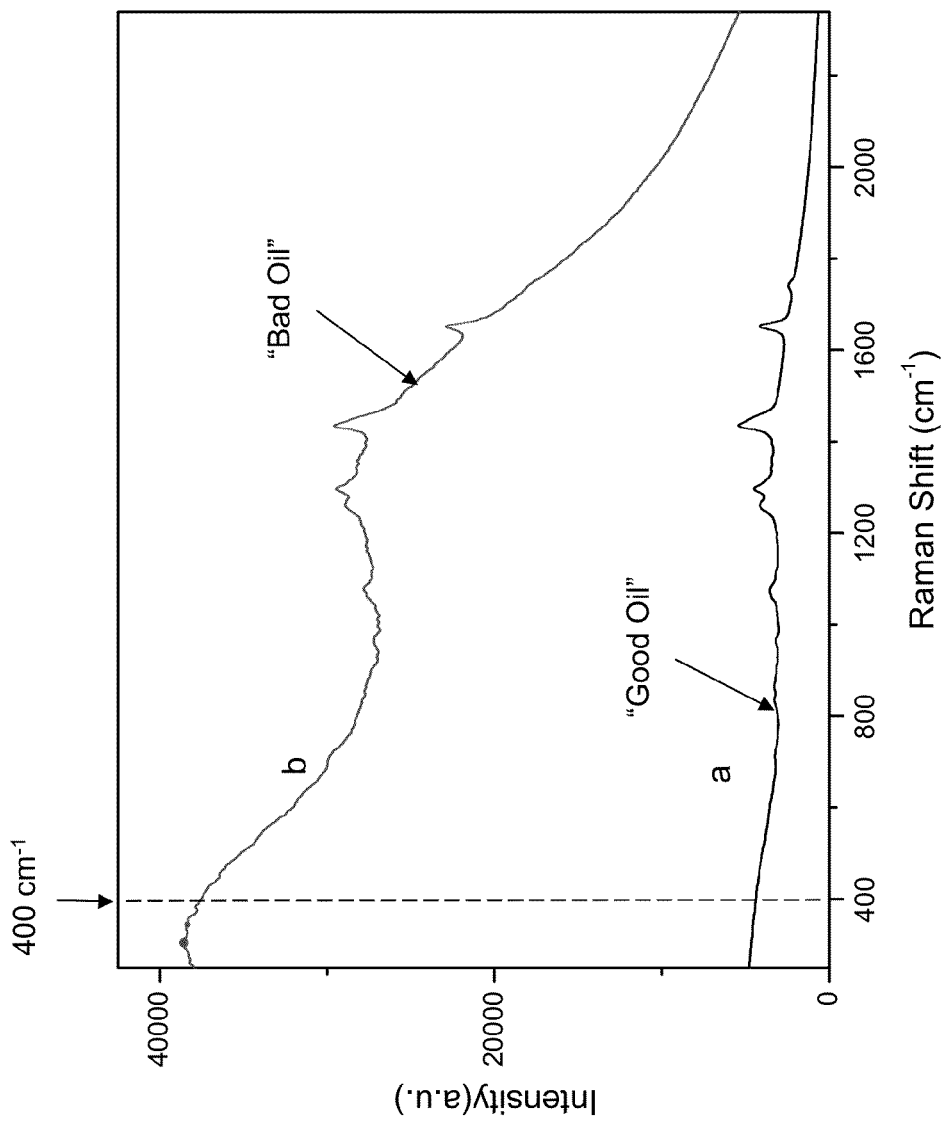
FIG. 31 shows normal Raman spectra obtained from a "good oil" and a "bad oil".

Details about the two steps are now described. FIG. 31 shows normal Raman spectra for a "good oil" and a "bad oil". The background fluorescence intensity in the spectral range from 250 cm$^{-1}$ to 600 cm$^{-1}$ such as at about 400 cm$^{-1}$ can be used to be as a qualitative criterion for determining the types of oil. Most of the "bad oils" have their background fluorescence intensity above 15,000, with exceptions for some recycled oils. Most of the "good oils" have their background fluorescence intensity below 15,000, with exceptions for fresh Class-4 vegetable seed oils (rapeseed oils) and fresh sesame oils.

Figure 32:
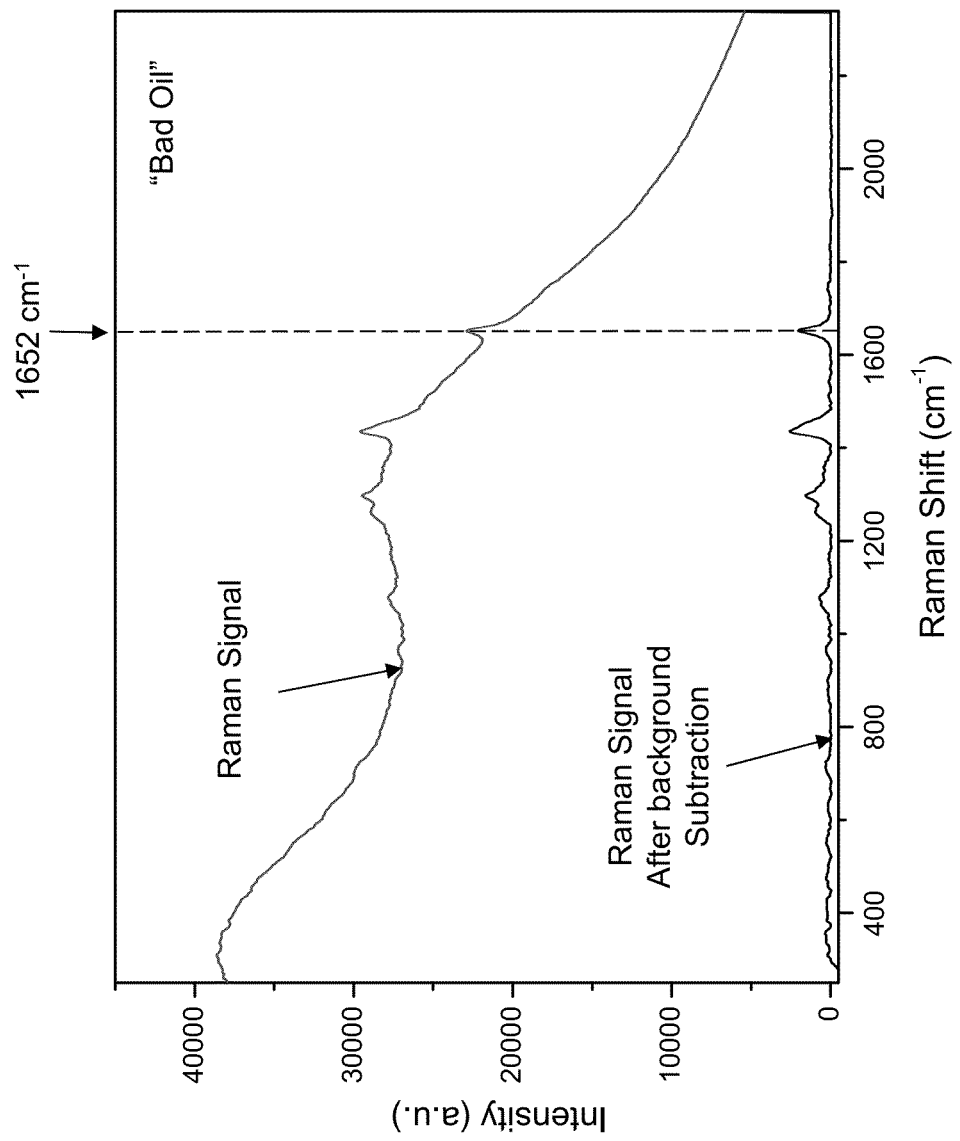
FIG. 32 shows normal Raman spectra with and without background subtraction for the "bad oil".
Figure 33:
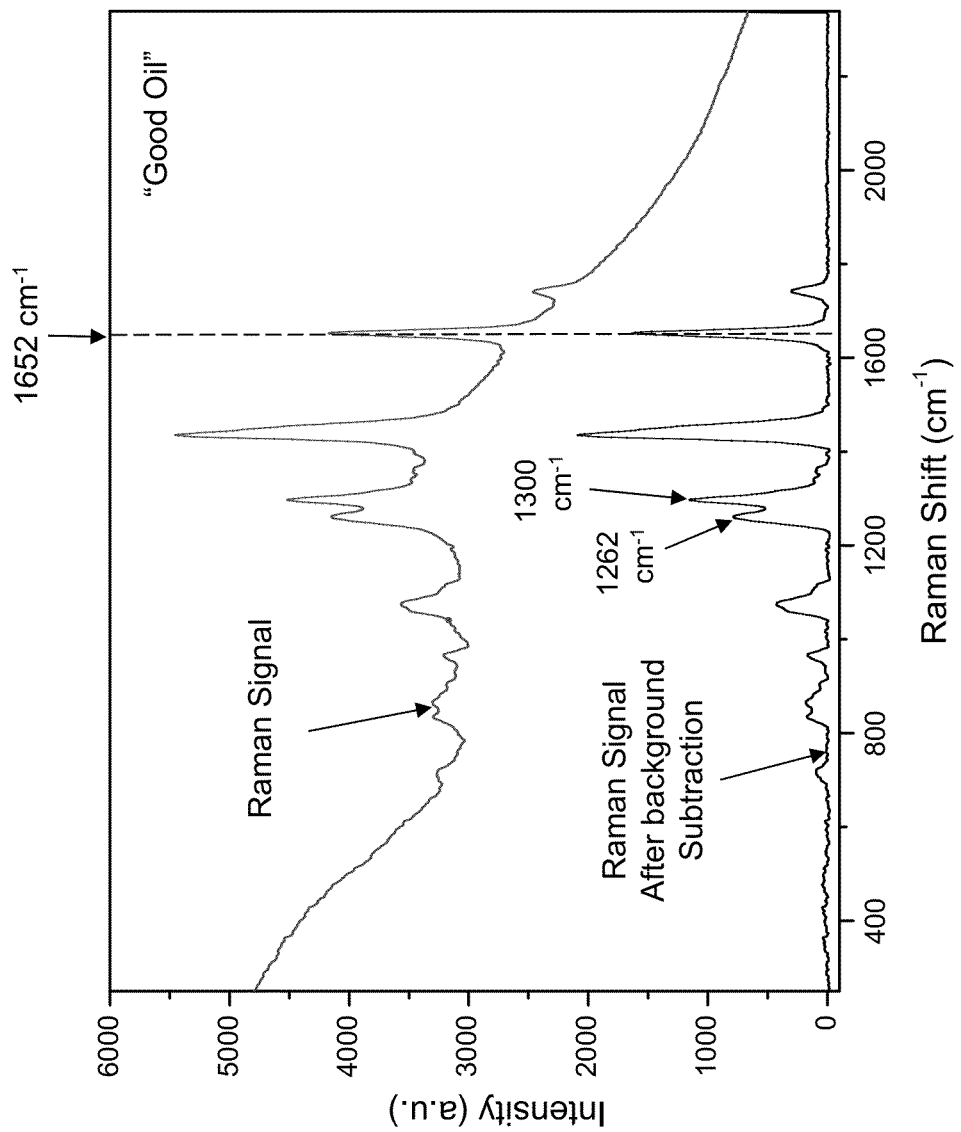
FIG. 33 shows normal Raman spectra with and without background subtraction for the "good oil".

"Good oils" and "bad oils" can be quantitatively determined by looking at the Raman spectral signatures at around 1652 cm$^{-1}$. Referring to FIG. 32, a Raman spectrum obtained from a "bad oil" sample is shown above. The Raman fluorescence background is subtracted from the Raman spectrum. The background-subtracted Raman spectrum is shown below. The same background subtract is also conducted on the Raman spectrum obtained from a "good oil" sample as shown in FIG. 33. It was observed that the spectral signature at about 1652 cm$^{-1}$ is decreased by a much larger magnitude for the "bad oil" than that for the "good oil".

The applicants have found that "good oils" and "bad oils" can be differentiated by a fluorescence-background ratio FBR at about 1652 cm$^{-1}$ defined as:

$$FBR = I_{1652}/(I_{1652} - I_{Background}) \quad (1)$$

Wherein $I_{1652}$ is the Raman spectral intensity and $I_{Background}$ is the Raman fluorescence background intensity. The applicants have found that "bad oils" have high FBRs and the "good oils" have low FBRs. "Bad oils" can be identified by oil samples having FBRs higher than a predetermined value such as 3, 4, or 5. "Good oils" can be identified by oil samples having FBRs lower than a predetermined value such as 3, 4, or 5.

The FBRs for typical plant-related cooking oils are shown in Table II, which are in the range between 0.5 and 4 except for palm oil that has a FBR of about 0.4. Thus FBRs can be used as an effective tool to differentiate "good oils" and "bad oils" which have FBR values much higher than 4. Exemplified Raman signatures include those located about 1262 cm$^{-1}$, 1300 cm$^{-1}$, and 1652 cm$^{-1}$.

Figure 34:
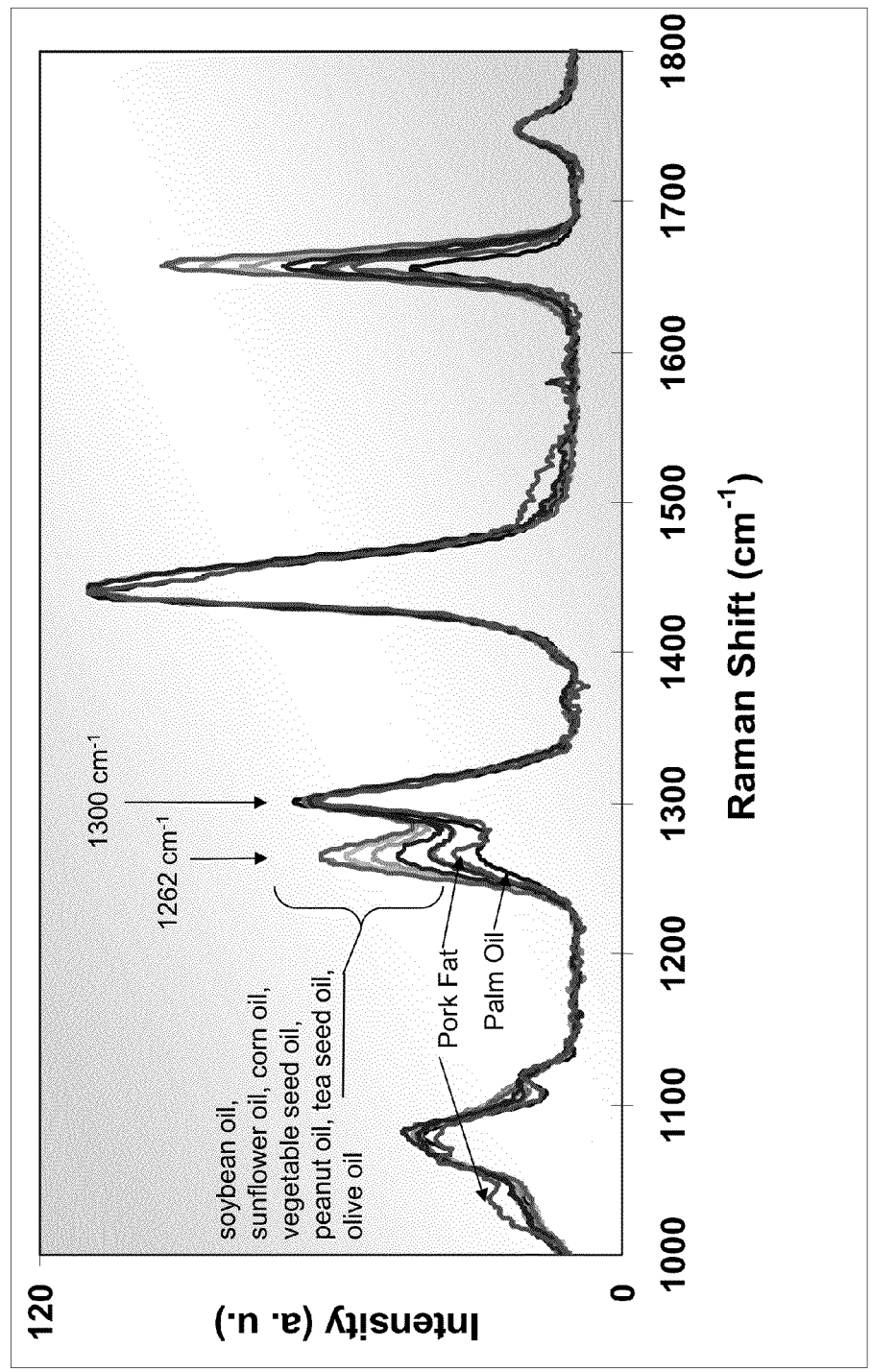
FIG. 34 shows normal Raman spectra of several edible oils.

In some embodiments, still referring to FIG. 34, the applicants have further discovered that the Raman peak intensity ratio (RIR) about 1262 cm$^{-1}$ and 1300 cm$^{-1}$ can be used to identify whether an edible oil is mixed with palm oil, or not.

In some embodiments, the "bad oil" can also include adulterated edible oils, which can also be detected using Raman spectroscopy in according to the present invention. Cooking oils that are labeled as soybean oil, corn oil, and vegetable seed oil, etc are sometimes illegally adulterated by mixing with low cost oils such as palm oil. In other words, the content of the oil is not consistent with the label on the oil container. To detect these adulterated oils, Raman spectrum is first obtained from the oil sample. Background is subtracted from the Raman spectrum. The inventors have found that the Raman peak intensity ratio (RIR) of background subtracted Raman peaks about 1262 cm$^{-1}$ to that 1300 cm$^{-1}$ is effective for identifying adulterated edible oils.

FIG. 34 shows Raman spectra of several common edible oils. The Raman spectra are normalized with reference to the Raman peak about 1440 cm$^{-1}$. It is noted that the normalized Raman spectra of the several common edible oils substantially overlap with each other in much of the spectral range, as shown in FIG. 34. The inventors observed that the normalized peak intensities (or peak areas) about 1262 cm$^{-1}$ and 1652 cm$^{-1}$ are different for different edible oil content. Based on this observed property, the inventors have developed a method to determine whether an expensive edible oil is adulterated by mixing with cheaper edible oil (or fat, lard) or not.

As shown in Table II below, common cooking oils have such ratios in a range between 0.3 and 1.1, while the ratio for palm oil is about 0.3. Therefore, an abnormally low intensity ratio of the background-subtracted Raman peaks at about 1262 cm$^{-1}$ and 1300 cm$^{-1}$ is a marker for adulterated edible oil. For example, if the product label of an oil container advertises the edible oil as a grape seed oil, but the above mentioned ratio is measured to be significantly lower (e.g. by 0.2 or more) than the ratio value of 0.9~1.0 for the grape seed oil, it is then determined that the edible oil has been adulterated. A low cost palm oil has likely been mixed with grape seed oil or even replaced grape seed oil completely in the oil container. On the other hand, if edible oil container label showing pure peanut oil, however, Raman detected an abnormally higher intensity ratio (for example, RIR to about 0.8 or higher) of the background-subtracted Raman peaks about 1262 cm$^{-1}$ and 1300 cm$^{-1}$, a low cost soybean oil has likely been mixed with labeled peanut oil, at least, one can conclude that labeled pure peanut oil is adulterated with mixing other cheaper oil(s).

TABLE II

The Raman peak intensity ratios (RIR) of background subtracted Raman peaks about 1262 cm$^{-1}$ and 1300 cm$^{-1}$ for common cooking oils

| Oil Name | RIR |
| --- | --- |
| Palm Oil | ~0.3 |
| Corn Oil | 0.8-0.9 |
| Sunflower Oil | ~0.9 |
| Sesame Oil | ~1.1 |
| Peanut Oil | 0.6-0.7 |
| Olive Oil | ~0.5 |
| Soybean Oil | ~0.9 |
| Vegetable Seed Oil | 0.7-0.8 |
| Grape Seed Oil | ~0.9 |
| Lard | ~0.4 |

FIG. 34 shows normal Raman spectra of several edible oils, a palm oil and pork fat. As discussed above (FIGS. 27 and 34, Table II), pork fat (or lard) and palm oil are typical animal fat and low cost oil that are mixed with or to replace high quality plant or vegetable oils to produce adulterated or "bad" oil. The high quality plant or vegetable oils include, as shown in FIG. 34, olive oil, sunflower oil, rapeseed oil, corn oil, dark vegetable seed oil, soybean oil, grapeseed oil, and peanut oil. The ratio of the background-subtracted Raman peaks at about 1262 cm$^{-1}$ and 1300 cm$^{-1}$ is a marker for adulterated edible oil (such as low cost palm oil mixed into other kind of high quality oil, olive oil or grapeseed oil mixed with lower pricing edible oil (such as soybean oil, peanut oil, rapeseed oil, etc., or soybean oil mixed into peanut oil) as well as for animal fat (such as pork). Both pork fat and palm oil have low ratios of the background-subtracted and normalized Raman peaks about 1262 cm$^{-1}$ to 1300 cm$^{-1}$, which can be readily distinguished from those ratios of the "good" vegetable or plant oils. In addition, pork fat shows a special characteristic low-peak and valley shape at about 1262 cm$^{-1}$, which can be easily recognized; pork fat also shows its special Raman spectral profile at about 1030 cm$^{-1}$. In summary, the marker such as the ratio of the background-subtracted and normalized Raman peaks at about 1262 cm$^{-1}$ and 1300 cm$^{-1}$ can be used as an effective tool to detect both animal fat and adulterated edible oils.

Figure 35:
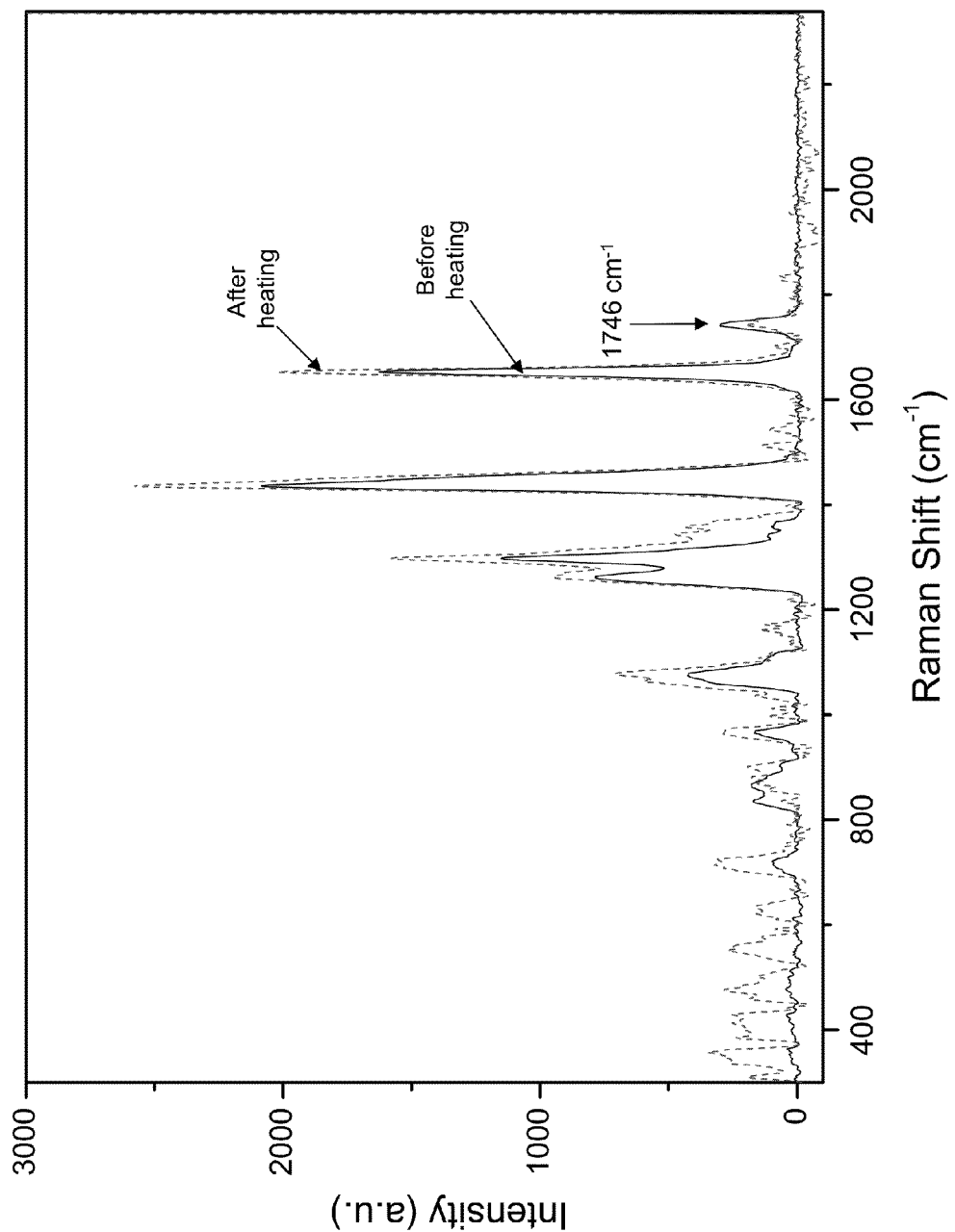
FIG. 35 shows background-adjusted normal Raman spectra obtained from a cooking oil before and after being heated at elevated temperatures.

Furthermore, it is observed that certain background-adjusted Raman signatures decrease after the oil has been heated at elevated temperatures. FIG. 35 shows background-adjusted Raman spectra obtained from a cooking oil before and after being heated at elevated temperatures. Applicants have found that the spectral intensity of the spectral signature at about 1746 cm$^{-1}$ has decreased in the background-adjusted Raman spectra. It is conceptualized that the decreased peak intensity at about 1746 cm$^{-1}$ is caused by the hydrolysis of the ester bonds C=O by heating. Thus the decrease in some spectral signatures in background-adjusted Raman spectra can be used as a criterion for identifying cooking oil that has been used in cooking.

Figure 27:
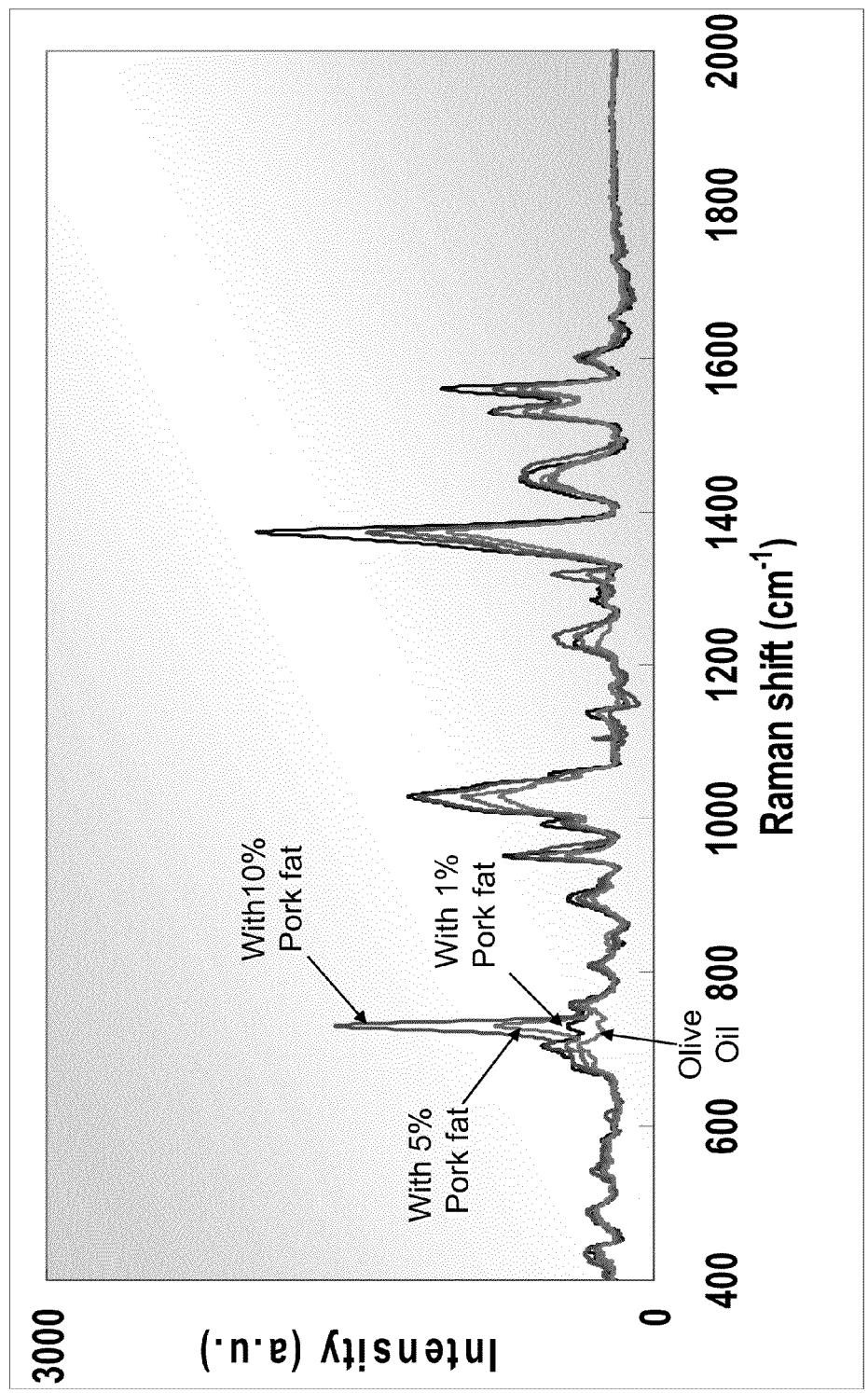
FIG. 27 shows Raman spectra obtained from different concentrations of pork fat oil mixed into an olive oil in comparison to a pure olive oil.
Figure 36:
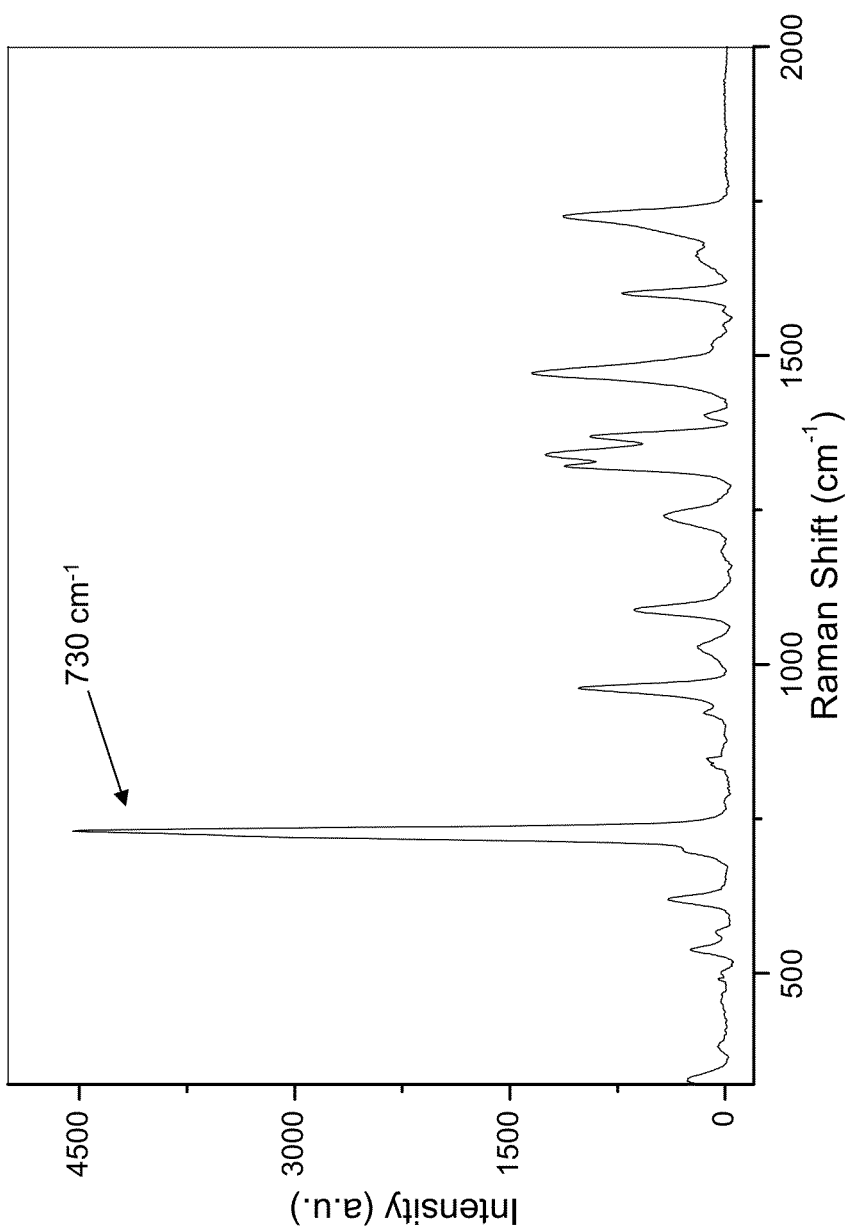
FIG. 36 shows a Raman spectrum obtained from an oil containing animal fat.

Moreover, related to findings shown in FIGS. 25, 27 and 28 above, it is found that edible oil samples that contain animal fat have a strong spectral signature at about 730 cm$^{-1}$ in a background-adjusted Raman spectrum, as shown in FIG. 36, which provides a spectral marker for "bad oils".

Figure 37:
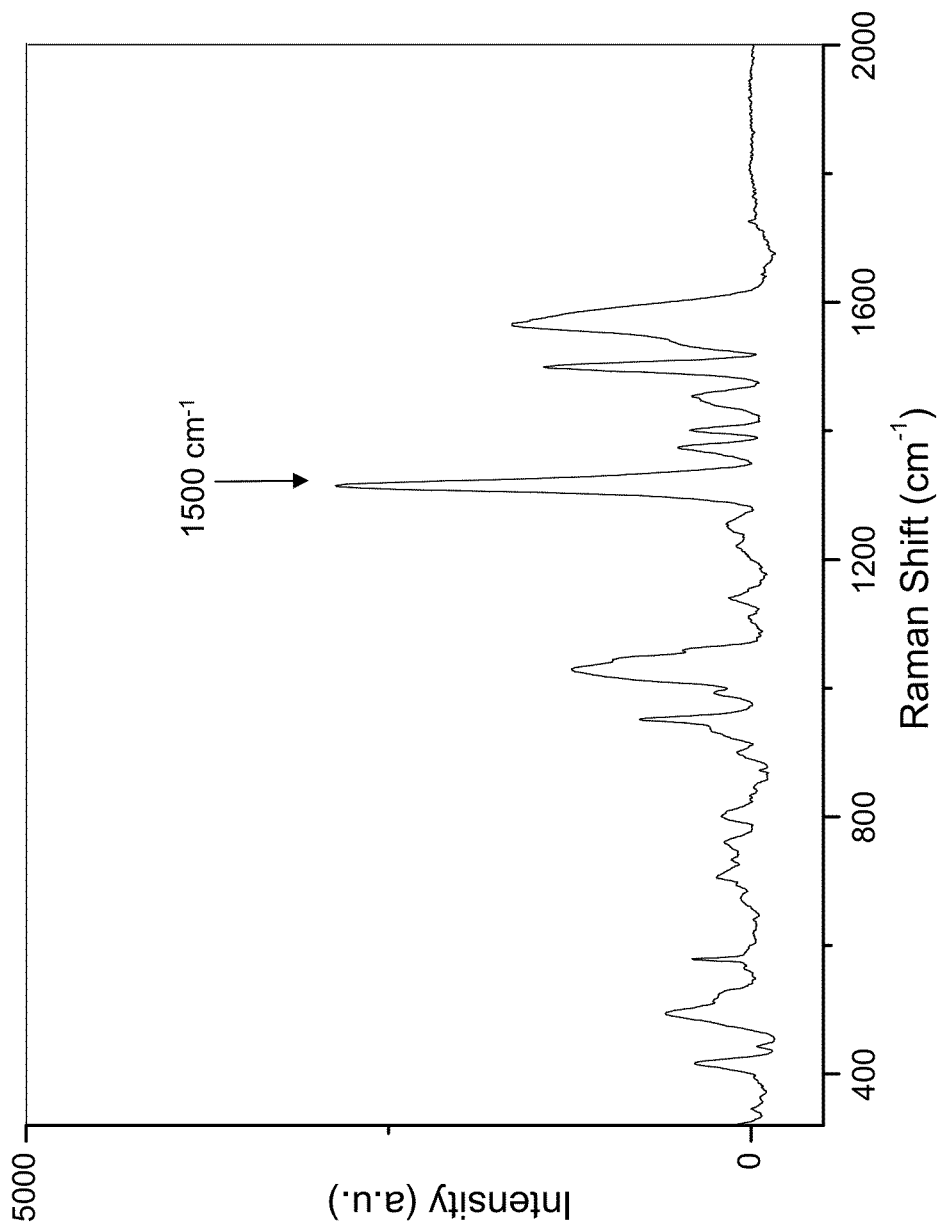
FIG. 37 shows a Raman spectrum obtained from a vegetable seed oil.

In another example, referring to FIG. 37, a Raman spectrum obtained from a vegetable seed oil (or rapeseed oil) shows a strong spectral signal at about 1500 cm$^{-1}$. It was found that a prominent spectral signature at about 1500 cm$^{-1}$ provides a marker for an edible oil which may be mixed with the rapeseed oil (which is cheaper than other typical edible oils and the label placed on the oil container may not show rapeseed oil contained). Similarly, peanut oil can be identified by the Raman peaks about 730 cm$^{-1}$ (weak) and 1162 cm$^{-1}$ (strong).

The identification of spectral signatures for detecting waste cooking oils (bad oils) can be assigned by statistical analysis and several computation algorithms such as dendrograph classification and Principal Component Analysis.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention. For example, the identification of "bad oils" and "good oil" can be made at Raman shift adjacent to or different from those spectral signatures described above.

What is claimed is:

1. A method for inspecting an edible oil, comprising:
   obtaining a first Raman spectrum from an edible oil sample;
   discovering presence of an unhealthy, unsanitary, unsafe, or adulterated content in the edible oil sample in part by the intensity level of a first fluorescence background in the first Raman spectrum;
   introducing the edible oil sample to nano-scale surface structures to allow molecules of the edible oil sample to be adsorbed to the nano-scale surface structures;
   illuminating the edible oil sample and the nano-scale surface structures by a laser beam;
   obtaining a second Raman spectrum from light scattered by molecules of the edible oil sample adsorbed to the nano-scale surface structures; and
   identifying the unhealthy, unsanitary, or unsafe content in the edible oil sample using one or more first spectral signatures in the second Raman spectrum.

2. The method of claim 1, wherein the step of discovering comprises:
   determining the existence of unhealthy, unsanitary, or unsafe content in the edible oil sample if the first fluorescence background in the first Raman spectrum is above a threshold level.

3. The method of claim 2, wherein the first fluorescence background in the first Raman spectrum is measured in the spectral range from 250 cm$^{-1}$ to 600 cm$^{-1}$.

4. The method of claim 2, wherein the threshold level is within a range between about 8,000 and about 30,000.

5. The method of claim 1, wherein the unhealthy, unsanitary, or unsafe content comprises one or more of a waste edible oil, swill oil, oils refined from animal skin of pigs, cows, veal, chickens, or oils refined from animal visceral, or repeatedly reused edible oil.

6. The method of claim 5, wherein the unhealthy, unsanitary, or unsafe content comprises one or more of an edible oil that fried French fries, an edible oil that fried lamb, pork, or chick, or edible oil that is mixed with pork fat.

7. The method of claim 1, wherein the adulterated content in the edible oil sample comprises palm oil.

8. The method of claim 1, further comprising:
   establishing a plurality of spectral signatures in surface enhanced Raman spectra for a plurality of edible oils; and
   identifying a specific unhealthy, unsanitary, or unsafe content in at least one of the plurality of edible oils using the plurality of spectral signatures.

9. The method of claim 8, wherein the plurality of spectral signatures are located at or around 620 cm$^{-1}$, 730 cm$^{-1}$, or 960 cm$^{-1}$.

10. The method of claim 1, further comprising:
    determining a concentration of the unhealthy, unsanitary, unsafe, or adulterated content in the edible oil sample using the one or more first spectral signatures.

11. The method of claim 1, further comprising:
    establishing a second spectral signature in surface enhanced Raman spectra for a fresh edible oil; and
    identifying the edible oil sample as the fresh edible oil using the second spectral signature in the first Raman spectrum.

12. The method of claim 11, wherein the fresh edible oil comprises corn oil, peanut oil, a light vegetable seed oil, rapeseed oil, dark vegetable seed oil, sunflower oil, palm oil, olive oil, grapeseed oil, safflower oil, cotton seed oil, coconut oil, sesame oil, tea oil, and soybean oil.

13. The method of claim 12, wherein the second spectral signature is located at or around 1,500 cm$^{-1}$, which corresponds to a light vegetable seed oil or rapeseed oil.

14. The method of claim 12, wherein the second spectral signature is located at or around 1,162 cm$^{-1}$, which corresponds to peanut oil.

15. The method of claim 1, wherein the step of identifying further comprises:
    subtracting a second fluorescence background from the second Raman spectrum to obtain a background-subtracted Raman spectrum; and
    identifying the unhealthy, unsanitary, unsafe, or adulterated content using the one or more first spectral signatures in the second Raman spectrum and in the background-subtracted Raman spectrum.

16. The method of claim 15, wherein the step of identifying further comprises:
    calculating a ratio of an intensity of one of the one or more first Raman signatures in the background-subtracted Raman spectrum to the second fluorescence background; and
    identifying the unhealthy, unsanitary, unsafe, or adulterated content in the edible oil sample if the ratio is above 3.

17. The method of claim 16, wherein unhealthy, unsanitary, unsafe, or adulterated content is identified in the edible oil sample if the ratio is above 4.

18. The method of claim 17, wherein unhealthy, unsanitary, unsafe, or adulterated content is identified in the edible oil sample if the ratio is above 5.

19. The method of claim 15, further comprising:
    qualifying the edible oil sample as a fresh edible oil if the ratio is below a threshold value.

20. The method of claim 1, further comprising:
    introducing the edible oil sample to the nano particles in a solution, or on a nano-structured surface, wherein the nano-scale surface structures are provide by nano particles.

21. The method of claim 20, wherein the nano particles comprise a magnetic or ferromagnetic material.

22. The method of claim 20, further comprising applying an electrical field, a magnetic field, or an electro-magnetic field to the sample solution during at least a portion of the step of collecting.

23. A method for inspecting an edible oil, comprising:
    obtaining a Raman spectrum from an edible oil sample;
    subtracting a background from the Raman spectrum to obtain a background-subtracted Raman spectrum;
    identifying a first Raman signature in the Raman spectrum;

identifying a second Raman signature in the Raman spectrum;

calculating a first ratio of the intensities of the first Raman signature and the second Raman signature in the background-subtracted Raman spectrum; and identifying an adulterated content in the edible oil sample using the first ratio.

24. The method of claim 23, wherein the first Raman signature is at around $1262\ cm^{-1}$, and wherein the second Raman signature is at around $1300\ cm^{-1}$.

25. The method of claim 23, further comprising:

obtaining an advertised content for the edible oil sample from a product label for the edible oil sample;

obtaining a second ratio of the intensities of the first Raman signature and the second Raman signature in a background-subtracted Raman spectrum for the advertised content; and identifying the adulterated content in the edible oil sample by comparing the first ratio and the second ratio.

26. The method of claim 25, wherein the second ratio is smaller than the first ratio.

27. The method of claim 25, wherein the adulterated content is identified in the edible oil sample if the first ratio differs from the second ratio by a predetermined value.

28. The method of claim 23, wherein the adulterated content includes palm oil or rapeseed oil in edible oils, or soybean oil in peanut oil or olive oil.

\* \* \* \* \*